United States Patent
Liu et al.

(10) Patent No.: US 11,278,567 B2
(45) Date of Patent: Mar. 22, 2022

(54) METHODS OF MODIFYING NEURONAL FUNCTION BY CHANGING INTRACELLULAR MAGNESIUM LEVELS

(71) Applicant: Neurocentria, Inc., Hayward, CA (US)

(72) Inventors: Guosong Liu, Oakland, CA (US); Hang Zhou, Hayward, CA (US)

(73) Assignee: Neurocentria, Inc., Hayward, CA (US)

( * ) Notice: Subject to any disclaimer, the term of this patent is extended or adjusted under 35 U.S.C. 154(b) by 0 days.

(21) Appl. No.: 16/803,633

(22) Filed: Feb. 27, 2020

(65) Prior Publication Data

US 2020/0297758 A1 Sep. 24, 2020

Related U.S. Application Data

(62) Division of application No. 15/210,715, filed on Jul. 14, 2016, now Pat. No. 10,617,713.

(60) Provisional application No. 62/305,346, filed on Mar. 8, 2016.

(51) Int. Cl.
*A61K 33/06* (2006.01)
*G01N 33/50* (2006.01)
*A61K 31/191* (2006.01)
*G01N 33/84* (2006.01)

(52) U.S. Cl.
CPC ............ *A61K 33/06* (2013.01); *A61K 31/191* (2013.01); *G01N 33/5058* (2013.01); *G01N 33/84* (2013.01); *G01N 2800/2814* (2013.01); *G01N 2800/52* (2013.01)

(58) Field of Classification Search
CPC .. A61K 33/06; A61K 31/191; G01N 33/5058; G01N 33/84; G01N 2800/2814; G01N 2800/52
USPC .......................................................... 514/557
See application file for complete search history.

(56) References Cited

U.S. PATENT DOCUMENTS

| | | | |
|---|---|---|---|
| 8,142,803 B2 | 3/2012 | Liu et al. | |
| 8,163,301 B2 | 4/2012 | Liu et al. | |
| 8,178,118 B2 | 5/2012 | Liu et al. | |
| 8,178,132 B2 | 5/2012 | Liu et al. | |
| 8,178,133 B2 | 5/2012 | Liu et al. | |
| 8,377,473 B2 | 2/2013 | Liu et al. | |
| 8,470,352 B2 | 6/2013 | Liu et al. | |
| 8,637,061 B2 | 1/2014 | Liu et al. | |
| 8,734,855 B2 | 5/2014 | Liu et al. | |
| 9,125,878 B2 | 9/2015 | Liu et al. | |
| 9,616,038 B2 | 4/2017 | Liu et al. | |
| 2008/0248100 A1 | 10/2008 | Liu et al. | |
| 2008/0249170 A1 | 10/2008 | Liu et al. | |

FOREIGN PATENT DOCUMENTS

| | | |
|---|---|---|
| JP | 2014019649 | 2/2014 |
| WO | WO 2008116226 | 9/2008 |

OTHER PUBLICATIONS

Duman And Aghajanian (2010) "Synaptic Dysfunction in Depression Potential Therapeutic Targets", Science 338: 68-72.
Harrison et al., (2009) "Vitamin C Function in the Brain: Vital Role of the Ascorbate Transporter SVCT2", Free Radical Biology and Medicine, 46(6): 719-730.
Li et al., (2014) "Elevation of Brain Magnesium Prevents Synaptic Loss and Reverses Cognitive Deficits in Alzheimers Disease Mouse Model", Molecular Brain, 65.
Liu et al., (2016) "Efficacy and Safety of MMFS-01, A Synapse Density Enhancer, for Treating Cognitive Impairment in Older Adults: A Randomized. Double-Blind. Placebo-Controlled Trail", Journal of Alzheimer's Disease 49 971-990.
Noraberg et al., (2005) "Organotypic Hippocampal Slice Cultures for Studies of Brain Damage, Neuroprotection and Neurorepair", Current Drug Targets—CNS & Neurological Disorders 4(4): 435-452.
Qifeng et al., (2016) "Regulation of Structural and Functional Synapse Density by L-threonate through Modulation of Intraneuronal Magnesium Concentration", 108: 426-439.
Slutsky (2010) "Enhancement of Learning and Memory by Elevating Brain Magnesium", Neuron 65: 165-177.
Zhou And Liu (2015) "Regulation of Density of Functional Presynaptic Terminals by Local Energy Supply", Molecular Brain 8:42: 1-21.

*Primary Examiner* — Kristin A Vajda
(74) *Attorney, Agent, or Firm* — Rudy J. Ng; Bozicevic, Field & Francis LLP

(57) ABSTRACT

Methods for modifying neuronal functional activity and/or treating a neurological disorder by using agents that raise neuronal intracellular concentration of magnesium are disclosed. Also provided herein are methods of determining the amenability of an individual to treatment for a neurological disorder, by measuring changes in intracellular magnesium concentration.

14 Claims, 31 Drawing Sheets

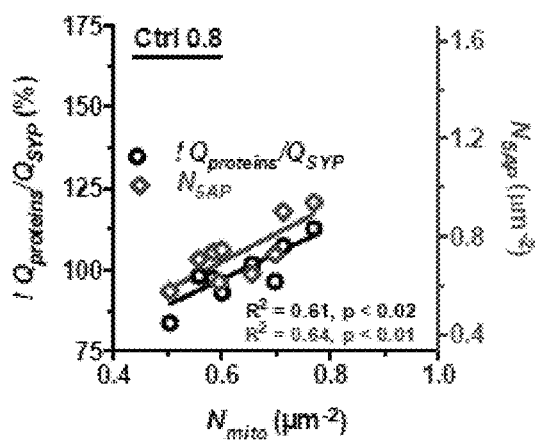
Figure 7B
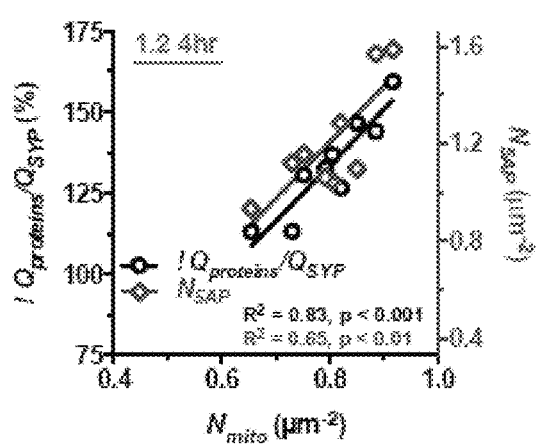
Figure 7C
Figure 8A
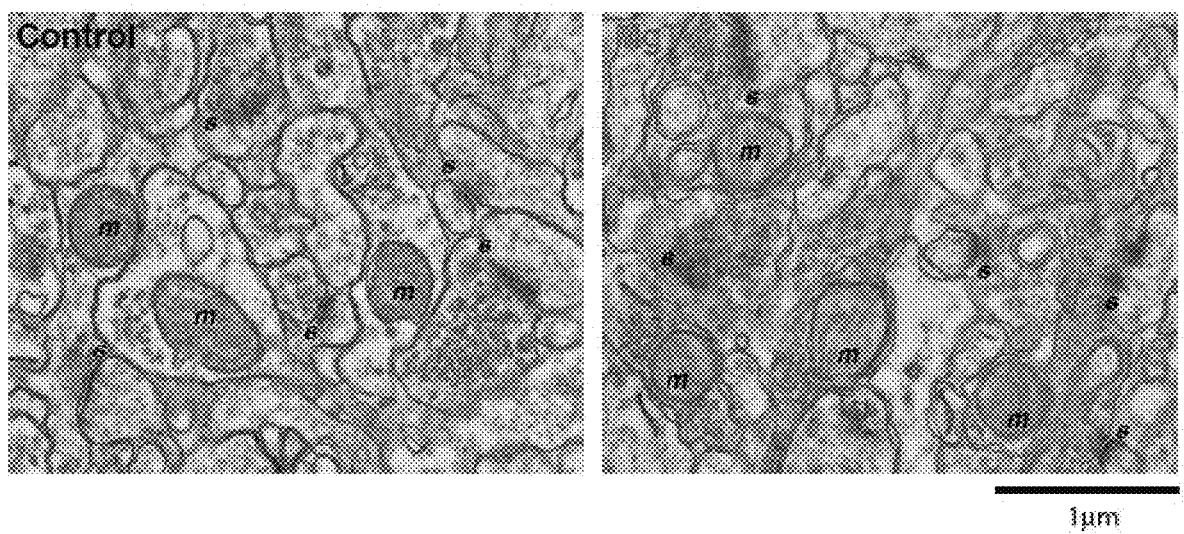
Figure 8B
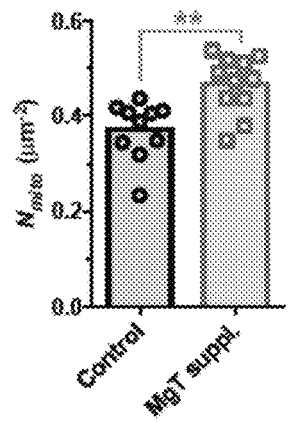

Figure 11

| Table 1. Baseline characteristics according to treatment group | | |
|---|---|---|
| Characteristic | Placebo (n=26) | MMFS-01 (n=25) |
| Age - yr ± SD | 57.6 ± 4.4 | 57.1 ± 6.0 |
| Sex - no. (%) | | |
|     Male | 8 (31%) | 7 (28%) |
|     Female | 18 (69%) | 18 (72%) |
| Ethicity - no. (%) | | |
|     Hispanic | 25 (96%) | 22 (88%) |
|     Non-Hispanic | 1 (4%) | 3 (12%) |
| Race - no (%) | | |
|     African-American | 3 (12%) | 2 (8%) |
|     Caucasian | 23 (88%) | 23 (92%) |
| Medical History - no. (%) | | |
|     Cardiovascular | 10 (%) | 9 (36%) |
|     Dermatological | 0 (0%) | 3 (12%) |
|     Ears/Nose/Throat/Mouth/Eyes | 6 (23%) | 6 (24%) |
|     Endocrine/Metabolic | 7 (27%) | 5 (20%) |
|     Gastrointestinal | 14 (54%) | 11 (44%) |
|     Musculoskeletal | 8 (31%) | 12 (48%) |
|     Neurological | 10 (38%) | 11 (44%) |
|     Renal/Genitourinary | 1 (4%) | 5 (20%) |
| CNS Medication - no. (%) | 0 (0%) | 0 (0%) |
| Height - cm ± SD | 159.7 ± 9.7 | 161.0 ± 9.1 |
| Weight - kg ± SD | 73.2 ± 12.9 | 73.1 ± 10.4 |
| MMSE Score ± SD | 28.2 ± 1.3 | 27.8 ± 1.6 |

Figure 12A

Table 2. Change from baseline in physiological measures

| Endpoint | Baseline Score (Mean±SEM) | Week 6 change from baseline | Week 6 p value (between groups) | Week 12 change from baseline | Week 12 p value (between groups) | Total Treatment p value |
|---|---|---|---|---|---|---|
| Physiological | | | | | | |
| Mg²⁺ Urine (mg/ml) | | | | | | |
| MMFS-01 | 0.061±0.003 | 0.026±0.007 | 0.140 | 0.035±0.007 | 0.046* | 0.027* |
| Placebo | 0.062±0.006 | 0.012±0.006 | | 0.005±0.007 | | |
| [Mg²⁺] Plasma (mg/dL) | | | | | | |
| MMFS-01 | 2.02±0.033 | 0.100±0.032 | 0.026* | 0.085±0.030 | 0.808 | 0.119 |
| Placebo | 2.06±0.041 | -0.002±0.043 | | 0.052±0.035 | | |
| [Mg²⁺] RBC (mg/10¹² cells) | | | | | | |
| MMFS-01 | 1.15±0.038 | 0.003±0.026 | 0.217 | 0.032±0.023 | 0.260 | 0.829 |
| Placebo | 1.19±0.035 | 0.049±0.026 | | -0.009±0.021 | | |

Mean±SEM
* significant p<0.05

Figure 12B

Table 3. Change from baseline in cognitive measures

| Endpoint | Baseline Score (Mean±SEM) | Week 6 change from baseline | Week 6 p value (between groups) | Effect size Cohen's d (95% C.I.) | Week 12 change from baseline | Week 12 p value (between groups) | Effect size Cohen's d (95% C.I.) | Total Treatment p value |
|---|---|---|---|---|---|---|---|---|
| Cognitive | | | | | | | | |
| TMT-B (ms⁻¹) | | | | | | | | |
| MMFS-01 | 10.6±1.0 | 2.6±0.8 | 0.066 | 0.58 (-0.08-1.17) | 2.1±0.8 | 0.116 | 0.51 (-0.10-1.10) | 0.047* |
| Placebo | 11.2±0.9 | 0.1±0.5 | | | 0.2±0.8 | | | |
| DigitSpan (Congruent) (s) | | | | | | | | |
| MMFS-01 | 11.52±0.59 | 1.61±0.48 | 0.023* | 0.61 (-0.01-1.20) | 1.43±0.55 | 0.225 | 0.30 (-0.31-0.88) | 0.064 |
| Placebo | 11.05±0.50 | 0.19±0.59 | | | 0.67±0.52 | | | |
| Flanker-Unconsgruens (Congruent) (s) | | | | | | | | |
| MMFS-01 | 0.04±0.03 | 0.04±0.03 | 0.565 | 0.27 (-0.33-0.85) | 0.05±0.03 | 0.443 | 0.15 (-0.76-0.47) | 0.660 |
| Placebo | 0.09±0.02 | 0.01±0.02 | | | 0.03±0.03 | | | |
| Face-Name (#) | | | | | | | | |
| MMFS-01 | 1.79±0.14 | 0.12±0.16 | 0.484 | 0.30 (-0.31-0.72) | 0.64±0.19 | 0.089 | 0.44 (-0.18-1.05) | 0.103 |
| Placebo | 1.57±0.13 | 0.34±0.18 | | | 0.35±0.19 | | | |
| Overall Cognitive Ability (r) | | | | | | | | |
| MMFS-01 | -0.025±0.11 | 0.41±0.12 | 0.037* | 0.74 (0.12-1.34) | 0.82±0.13 | 0.003** | 0.91 (0.27-1.53) | 0.001** |
| Placebo | -0.002±0.11 | 0.08±0.08 | | | 0.05±0.14 | | | |

Mean±SEM
* significant p<0.05
** significant p<0.01

Figure 13

Table 5. All adverse events observed in the study

| Adverse Event | # of Events | | # of Subjects | |
|---|---|---|---|---|
| | MMFS-01 (n=25) | Placebo (n=26) | MMFS-01 (n=25) | Placebo (n=26) |
| Gastrointestinal disorders | 5 | 6 | 5 | 4 |
| General disorders and administration site conditions | 0 | 2 | 0 | 2 |
| Infections and infestations | 4 | 7 | 4 | 6 |
| Injury, poisoning and procedural complications | 0 | 1 | 0 | 1 |
| Musculoskeletal and connective tissue disorders | 3 | 0 | 3 | 0 |
| Nervous system disorders | 1 | 7 | 1 | 5 |
| Psychiatric disorders | 1 | 3 | 1 | 3 |
| Respiratory, thoracic and mediastinal disorders | 2 | 2 | 2 | 1 |
| Skin and subcutaneous tissue disorders | 0 | 1 | 0 | 1 |
| Surgical and medical procedures | 0 | 1 | 0 | 1 |
| Vascular disorders | 1 | 0 | 1 | 0 |
| All Organ Systems | 17 | 30 | 13 | 13 |

METHODS OF MODIFYING NEURONAL FUNCTION BY CHANGING INTRACELLULAR MAGNESIUM LEVELS

CROSS-REFERENCE TO RELATED APPLICATIONS

This application is a divisional of U.S. application Ser. No. 15/210,715, filed Jul. 14, 2016, now U.S. Pat. No. 10,617,713, which claims the benefit pursuant to 35 U.S.C. § 119(e) of U.S. Provisional Patent Application No. 62/305,346, filed Mar. 8, 2016, which applications are incorporated herein by reference in their entirety.

INTRODUCTION

Cognitive function declines with aging, and cognitive impairment in elderly is a major problem that can affect activities of daily living (ADL) and quality of life. Cognitive decline is correlated with brain atrophy associated with synaptic loss. For instance, alteration of synaptic efficacy in the hippocampus is an initial event in cognitive disorders such as Alzheimer's disease (AD). Functional synapses are the elemental unit of synaptic computation in the neural network, and the density of functional synapses determines the capacity for information transmission. The structural and functional loss of synapses are associated with impaired cognition. Even under physiological conditions, a considerable number of synapses are nonfunctional (i.e. silent/dormant), and the ratio of functional/nonfunctional synapses fluctuates over time.

Neural activity in brain is the means for brain computation. Orderly neural activity is essential for normal brain functions. Excessive or sustained neuronal activity in brain disrupts brain computation, resulting in the reduction of cognitive ability and behavior abnormality.

SUMMARY

Methods for improving synaptic transmission among neurons and/or improving cognitive function by using agents that raise neuronal intracellular concentration of magnesium are disclosed. Also provided herein are methods of determining the amenability of an individual to treatment for neurological disorder, e.g., cognitive impairment, by measuring changes in intracellular magnesium concentration.

Embodiments of the present disclosure include a method of modifying a functional property of neurons, the method including contacting one or more neurons containing a presynaptic terminal, with a composition containing an effective amount of an intracellular magnesium concentration ($[Mg^{2+}]_i$)-elevating agent, to modify one or more functional properties of the neurons, wherein the functional property includes one or more of: a functional presynaptic terminal density; a mitochondrial function per unit dendritic area; a terminal abundance of one or more presynaptic $Ca^{2+}$ sensitivity-related proteins; and a probability of synaptic release in response to background activity, e.g., low frequency single action potential input. In certain embodiments, the contacting is effective to: increase the functional presynaptic terminal density; increase the mitochondrial function per unit dendritic area; increase the abundance of one or more presynaptic $Ca^{2+}$ sensitivity-related proteins; and/or reduce the probability of synaptic release in response to low frequency single action potential input.

In certain embodiments, the agent includes a magnesium-containing compound or an inhibitor of intracellular magnesium efflux or a magnesium influx promoter. In certain embodiments, the effective amount of the $[Mg^{2+}]_i$-elevating agent raises an intracellular concentration of magnesium in the one or more neurons by 1.1 fold or more. In certain embodiments, the effective amount of the $[Mg^{2+}]_i$-elevating agent provides for an average extracellular concentration of magnesium from 0.6 mM to 1.4 mM. In certain embodiments, the effective amount of the $[Mg^{2+}]_i$-elevating agent provides for an average extracellular concentration of magnesium from 0.6 mM to 1.2 mM.

In certain embodiments, the contacting includes administering an effective amount of the $[Mg^{2+}]_i$-elevating agent, or a precursor thereof, to an individual. In certain embodiments, the agent, or a precursor thereof, is administered orally.

In certain embodiments, the method is for treating a neurological disorder, or a symptom thereof, in the individual. In certain embodiments, the neurological disorder is associated with insufficient synaptic density, or is associated with sustained and/or elevated spontaneous activity of neurons in the individual. In certain embodiments, the neurological disorder is selected from Alzheimer's disease, mild cognitive impairment (MCI), Parkinson's disease, dementia, Huntington's disease, autism, schizophrenia, cognitive decline as secondary effect of disease or medical treatment such as chemotherapy-related cognitive impairment or cognitive dysfunction (chemo brain), depression, sleep disorder, anxiety, attention deficit hyperactivity disorder (ADHD), migraine, headache, stroke, neuropathy, epilepsy, cerebral palsy, chronic pain, involuntary muscular contractions and convulsive twitches, spasm, wrinkling, dystonia and tremor, anxiety and depression associated with sustained neural activity in prefrontal cortex (PFC) and amygdala, and insomnia.

Also provided herein is a method that includes: administering a $[Mg^{2+}]_i$-elevating agent to an individual having or suspected of having a neurological disorder; determining a first level of magnesium in blood cells of a first blood sample obtained from the individual before the administering; and evaluating a change in cognitive competency of the individual from before to after the administering. In certain embodiments, the method further includes measuring the level of magnesium in the blood cells, before the administering, to determine the first level of magnesium. In certain embodiments, the method further includes determining a second level of magnesium in blood cells of a second blood sample obtained from the individual after the administering. In certain embodiments, the method further includes measuring the level of magnesium in the blood cells, after the administering, to determine the second level of magnesium. In certain embodiments, the method further includes continuing administration of the $[Mg^{2+}]_i$-elevating agent to the individual when the second level of magnesium is greater than the first level of magnesium.

In certain embodiments, the cognitive competency includes executive function, working memory, attention and/or short-term episodic memory. In certain embodiments, the method further includes administering a cognitive test for evaluating the cognitive competency of the individual before and/or after administering the $[Mg^{2+}]_i$-elevating agent. In certain embodiments, the method further includes continuing administration of the $[Mg^{2+}]_i$-elevating agent to the individual when the cognitive competency is not improved or is substantially the same as from before compared to after administering the $[Mg^{2+}]_i$-elevating agent, and when the second level of magnesium is greater than the first level of magnesium.

In certain embodiments, the neurological disorder includes cognitive impairment and/or a magnesium deficiency-caused neurological disorder. In certain embodiments, the cognitive impairment includes age-related cognitive decline, mild cognitive impairment, Alzheimer's disease, or cognitive fluctuation.

In any embodiment, the blood cells may include red blood cells.

In any embodiment, the $[Mg^{2+}]_i$-elevating agent may include a magnesium-containing compound, e.g., magnesium threonate.

Also provided herein is a method of reducing a cognitive impairment in an individual, the method including: administering an effective amount of magnesium threonate to a human individual having or suspected of having a cognitive impairment, wherein the effective amount reduces a functional age of a brain of the human individual. In certain embodiments, the effective amount includes an amount from 20 mg/kg/day to 50 mg/kg/day. In certain embodiments, the amount is from 20 mg/kg/day to 30 mg/kg/day. In certain embodiments, the magnesium threonate is administered for 6 days or more. In certain embodiments, the cognitive impairment includes cognitive fluctuation, age-related cognitive decline, mild cognitive impairment and/or a magnesium deficiency-caused neurological disorder.

In any embodiment, the magnesium threonate may be administered orally.

In any embodiment, the human individual may have an age of from 45 years to 80 years.

Also provided herein is a method of identifying an active agent that modifies a functional property of a neuron, the method including: contacting a first population of neurons in vitro with a first medium containing a candidate agent, wherein the neurons comprise a magnesium indicator dye; and measuring a level of intracellular magnesium ($[Mg^{2+}]_i$) in one or more subcellular regions of the neurons after the contacting, wherein the candidate agent is determined to be an active agent that modifies a $[Mg^{2+}]_i$-dependent functional property of a neuron when the measured level is higher than a reference level of intracellular magnesium, and wherein the $[Mg^{2+}]_i$-dependent functional property includes one or more of: a functional presynaptic terminal density; a mitochondrial function per unit dendritic area; an abundance of one or more presynaptic $Ca^{2+}$ sensitivity-related proteins; and an average probability of synaptic release in response to background activity, e.g., low frequency single action potential input. In certain embodiments, the one or more subcellular regions includes neuronal branches, and wherein measuring the level of intracellular magnesium includes: measuring for each neuronal branch: an average fluorescence level from the magnesium indicator dye; and a diameter of the branch; and calculating the level of intracellular magnesium based on the diameter and the average fluorescence level in each branch.

BRIEF DESCRIPTION OF THE FIGURES

The skilled artisan will understand that the drawings, described below, are for illustration purposes only. The drawings are not intended to limit the scope of the present teachings in any way.

FIGS. 7A-7C are a collection of graphs showing linear correlations between local energy supply, $Ca^{2+}$-sensitivity-related proteins in terminals and functional terminal density, according to embodiments of the present disclosure.

FIGS. 8A-8E are collection of images and graphs showing the quantity of $Ca^{2+}$-sensitivity-related proteins versus density of mitochondria in intact animals, according to embodiments of the present disclosure.

FIG. 11 shows Table 1, showing the baseline characteristics of patient cohorts used in randomized, double-blind placebo-controlled trial to evaluate the efficacy and safety of a treatment regimen with oral intake of MMFS-01, a compound containing magnesium threonate (L-threonic acid magnesium salt, L-TAMS), according to embodiments of the present disclosure.

FIG. 12A shows Table 2, showing physiological measures in patient cohorts for the MMFS-01 clinical trial, according to embodiments of the present disclosure.

FIG. 12B shows Table 3, showing changes in cognitive measures in patient cohorts for the MMFS-01 clinical trial, according to embodiments of the present disclosure.

FIG. 13 shows Table 5, showing adverse events observed during the MMFS-01 clinical trial.

DEFINITIONS

Figure 1A:
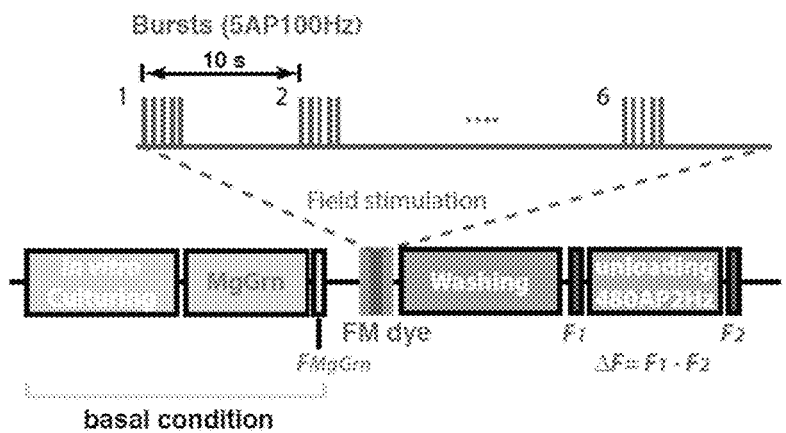
FIGS. 1A-1D are a collection of schematic diagrams, images and graphs showing the association of extracellular $Mg^{2+}$ concentration and functional terminal density in response to 5AP burst pattern of inputs, according to embodiments of the present disclosure.

The term "about" as used herein when referring to a measurable value such as an amount, a percentage, and the like, is meant to encompass variations of ±20%, such as ±10%, such as ±5%, ±1%, including ±0.1% from the specified value, as such variations are typical of measurements characterizing the disclosed subject matter, or are appropriate to perform the disclosed methods.

As used herein "substantially", may be applied to modify any quantitative representation that could permissibly vary without resulting in a change in the basic function to which it is related. For example, the amount of a precursor of a compound administered may be converted to an amount of the compound in the body that is somewhat different from an amount the compound being administered if the therapeutic or physiological effect of administering the precursor is not materially different from administering the compound.

An "individual" as used herein, may be any suitable animal amenable to the methods and techniques described herein, where in some cases, the individual may be a vertebrate animal, including a mammal, bird, reptile, amphibian, etc. The individual may be any suitable mammal, e.g., human, non-human primate, monkey, rodent, canine, feline, ungulate, etc. In some cases, the individual is a patient, e.g., an individual in need of treatment for a disease. In some cases, the individual is a human.

"Medium", as used herein, may refer to any aqueous solution that is physiologically compatible with a cell that contacts the solution. Where a cell is maintained in vitro, e.g., in culture or a tissue slice, the medium may be any suitable culture medium or buffer solution. Where a cell is in vivo, e.g., in an individual, the medium may be any extracellular fluid (e.g., interstitial fluids, blood plasma or serum, cerebrospinal fluid, etc.), that surrounds or contacts the cell in a tissue.

Generally, the term "cognition" may refer to a process of obtaining, organizing, understanding, processing, and/or using information or knowledge, performed using an individual's mental faculties. Generally, enhancing cognitive function refers to enhancing any aspect of such a process, such as learning, the performance of mental operations, the storage, retrieval, and/or use of information and/or thoughts, memory, and/or preventing a decline of a subjects cognitive state, for example. Various standardized tests may be used to evaluate cognition, cognitive function, and/or cognitive state and may be used to identify a subject who might be conducive to, benefit from, and/or need, maintenance and/or enhancement of same and/or to monitor an effect of treatment relating to same. Examples of suitable tests include the Mini-Mental Status Exam (Folstein, 1975), components of the PROSPER neuropsychological test battery (Houx, 2002), and/or the like. Family history, age, and/or other factors may also be used to identify a subject who might be conducive to, benefit from, and/or need, maintenance and/or enhancement of cognition, cognitive function, and/or cognitive state.

As used herein, the terms "treat," "treatment," "treating," and the like, refer to obtaining a desired pharmacologic and/or physiologic effect. The effect may be prophylactic in terms of completely or partially preventing a health condition, disease or symptoms thereof and/or may be therapeutic in terms of a partial or complete cure for a health condition, disease and/or adverse effect attributable to the health condition or disease. "Treatment," as used herein, covers any treatment of a health condition or disease in a mammal, particularly in a human, and includes: (a) preventing the health condition or disease from occurring in a subject which may be predisposed to the health condition or disease but has not yet been diagnosed as having it; (b) inhibiting the health condition or disease, i.e., arresting its development; and (c) relieving the health condition or disease, e.g., causing regression of the disease, e.g., to completely or partially remove symptoms of the health condition or disease.

A "therapeutically effective amount" or "efficacious amount" means the amount of an active agent that, when administered to a cell, a tissue, a mammal or other individual for obtaining a desired change in a physiological parameter, e.g., for treating a disease, is sufficient to effect such desired change, e.g., treatment for the disease or condition. The "therapeutically effective amount" will vary depending on the agent, the disease or condition and its severity and the age, weight, etc., of the subject to be treated.

By "pharmaceutically acceptable" is meant a material that is not biologically or otherwise undesirable, i.e., the material may be incorporated into a pharmaceutical composition administered to an individual without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Magnesium" as used herein is meant to generally refer an ionized form (i.e., a molecular or ionic form that is not bound to a protein; e.g., $Mg^{2+}$) that is present in a cell or in the extracellular environment, unless otherwise indicated.

"Level" as used in reference to a level of magnesium, e.g., ionized magnesium, may refer to an experimentally determined concentration, or an estimate of the concentration, of magnesium in a given volume or cellular compartments (e.g., in cells of a specific cell type). In some cases, the estimate of the concentration is proportional to the actual concentration within the range of the measurement.

"Presynaptic terminal" as used herein, refers to a generally dendritic region of a neuron that may be defined by localization of synaptic vesicles, or of proteins involved in synaptic vesicle turnover, and/or by having a postsynaptic partner configured to detect neurotransmitter release upon synaptic vesicle release.

A "neuronal branch" as used herein, may refer to a segment of a neurite defined by two points along the neurite where the neurite splits (e.g., bifurcates) into segments having a narrower diameter, and where the segment of the neurite may have substantially the same diameter along the segment.

"Arbor" as used herein, may refer to a contiguous system of neuronal branches that arise from a single branch connected to the neuronal cell body.

"Associate" as used in reference to a relationship between a disease and a physiological process, is meant to include the physiological process being a cause of the disease, or the physiological process being a symptom of the disease.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

DETAILED DESCRIPTION

As summarized above, methods for modifying neuronal and/or cognitive functions by using agents that raise neuronal intracellular concentration of magnesium are disclosed. The inventors of the present disclosure have found ways to modify functional properties (e.g., the functional presynaptic terminal density, the probability of synaptic release) of neurons by manipulating the neuronal environment, according to methods of the present disclosure, such that the intracellular concentration of ionized magnesium ($[Mg^{2+}]_i$) of the neurons is increased. In particular, contacting neurons with a $[Mg^{2+}]_i$-elevating agent, according to methods of the present disclosure, may increase their functional presynaptic terminal density, may increase the mitochondrial function per unit dendritic area, may increase the abundance of one or more presynaptic $Ca^{2+}$ sensitivity-related proteins and/or may selectively reduce probability of synaptic release in response to background activity, e.g., low frequency single action potential input. Such changes in the functional properties induced by methods of the present disclosure are changes that generally depend on the increase in the level of $[Mg^{2+}]_i$ of the neuron in which the changes are observed.

Aspects of the present disclosure include, administering a $[Mg^{2+}]_i$-elevating agent, such as magnesium threonate, to an individual to treat a cognitive impairment. In certain embodiments, $[Mg^{2+}]_i$ serves as a blood-based biomarker for assessing an individual's responsiveness to a treatment for cognitive impairment, such as that involving administration of magnesium threonate.

Further aspects of the present disclosure are now described.

Methods for Enhancing Neuronal Functional Properties

Provided herein is a method of modifying a function and/or functional property of a neuron mediated by $[Mg^{2+}]_i$. The method may include contacting one or more neurons (e.g., neurons that are synaptically connected among each other) with an agent that raises $[Mg^{2+}]_i$ of the neuron (i.e., a $[Mg^{2+}]_i$-elevating agent), where the increase in $[Mg^{2+}]_i$ induced by the agent may be sufficient to modify a functional property of the neurons. Thus, a "$[Mg^{2+}]_i$-elevating agent" as used herein, refers specifically to agents that can increase the intracellular concentration of ionized magnesium in neurons. The functional properties that are modified by the present methods include one or more (e.g., two or more, three or more, or all four) of a functional presynaptic terminal density, a mitochondrial function per unit dendritic area, an abundance of one or more presynaptic $Ca^{2+}$ sensitivity-related proteins, and probability of synaptic release in response to background activity, e.g., low frequency single action potential input.

The present methods may modify the functional property in a neuron across any suitable region of the neuron. In some embodiments, the modification of the functional property is induced across substantially the entire neuron (i.e., across substantially all pre-synaptic sites in the neuron). In certain embodiments, the modification of the functional property is induced in one or more spatially localized regions of the neuron. In certain embodiments, the modification of the functional property is localized to one or more (e.g., two or more, 3 or more, 5 or more, or 10 or more) dendritic arbors of the neuron. In certain embodiments, the modification of the functional property is localized to one or more (e.g., two or more, 3 or more, 5 or more, 10 or more, 15 or more or 20 or more) pre-synaptic boutons of the neuron. In some embodiments, the modification of the functional property is localized to neuronal regions (e.g., branches, boutons, etc.) that exhibit the increase in $[Mg^{2+}]_i$.

The modification of a functional property of the neurons induced by the present methods may be represented by a change in an experimentally determined measurement of the functional property after the contacting, compared to a reference value for the functional property. In some cases, the reference value is an experimentally determined measurement of the functional property before the contacting. In certain embodiments, the reference value is an experimentally determined measurement of the functional property in a suitable control population of neurons, such as neurons that are not contacted with the agent, but were otherwise exposed to a comparable environment as the neurons contacted with the $[Mg^{2+}]_i$-elevating agent.

The functional presynaptic terminal density may refer to the number of presynaptic terminals per unit area of dendritic arbor of a neuron that are capable of synaptic vesicle release after stimulation of the neuron with a physiologically relevant pattern of depolarizing. Releasable synaptic vesicles may be estimated by synaptic vesicle turnover, e.g., by monitoring releasable uptake of a suitable dye (e.g., an FM dyes, such as FM1-43 or FM4-64) due to the depolarizing stimulation. In some embodiments, the physiologically relevant pattern of depolarizing stimulation may include 6 bursts action potentials, where each burst includes 5 action potentials at 100 Hz, and the bursts may have a 10-second inter-burst interval.

Methods of the present disclosure may increase the functional presynaptic terminal density of the neurons by about 1.1 fold or more, e.g., about 1.2 fold or more, about 1.3 fold or more, about 1.5 fold or more, about 1.6 fold or more, about 1.7 fold or more, about 1.8 fold or more, about 2 fold or more, about 2.5 fold or more, including about 3 fold or more, relative to the functional presynaptic terminal density before the contacting. In some embodiments, the functional presynaptic terminal density may be increased by from about 1.1 fold to about 4 fold, e.g., from about 1.2 fold to about 3.5 fold, from about 1.3 fold to about 3.5 fold, from about 1.5 fold to about 3 fold, from about 1.6 fold to about 2.5 fold, from about 1.6 fold to about 2 fold, including from about 1.8 fold to about 2 fold, relative to the functional presynaptic terminal density before the contacting.

Modification of a functional property by methods of the present disclosure may include increasing the abundance of one or more $Ca^{2+}$ sensitivity-related proteins at presynaptic terminals of the neuron. Presynaptic $Ca^{2+}$ sensitivity-related proteins may include, e.g., synaptotagmin, Rab3, RIM1, Munc13-1, ELKS, and Syntaxin1. The abundance of $Ca^{2+}$ sensitivity-related proteins at presynaptic terminals of the neuron may be measured by, e.g., immunofluorescence staining.

In some embodiments, the abundance of a $Ca^{2+}$ sensitivity-related protein is increased in neuronal terminals by the present methods by about 20% or more, e.g., about 30% or more, about 40% or more, including about 50% or more, as measured by immunofluorescence staining, compared to control neurons that were not contacted with the agent. In some embodiments, the abundance of a $Ca^{2+}$ sensitivity-related protein is increased in presynaptic terminals by the present methods by from about 20% to about 60%, e.g., about 30% to about 55%, including about 40% to about 50%, compared to control neurons that were not contacted with the agent. The increase in abundance of the $Ca^{2+}$ sensitivity-related protein in presynaptic terminals may be due to enhanced transport of the $Ca^{2+}$ sensitivity-related protein to the dendritic presynaptic terminals.

Modification of a functional property by methods of the present disclosure may include increasing mitochondrial function per unit area of dendritic branches of the neurons. "Mitochondrial function per unit area" as used herein may refer to the density of mitochondria, the mitochondria membrane potential ($\Delta\Psi$), and/or the product of the density of mitochondria and $\Delta\Psi$. Mitochondrial function per unit area may be measured using, e.g., the $\Delta\Psi$-sensitive fluorescent dye JC-1.

In some embodiments, the mitochondrial function per unit area is increased by the present methods by from about 20% to about 80%, e.g., about 25% to about 75%, including about 30% to about 70%, compared to control neurons that were not contacted with the agent.

Modification of a functional property by methods of the present disclosure may include reducing the probability of synaptic release (Pr) in response to background activity of the neuron. "Background activity", or "background spontaneous activity" are used interchangeably, and refer to the frequency and/or pattern of action potential (AP) firing in a neuron that approximates the frequency and/or pattern of AP firing in response to excitatory synaptic input from presynaptic partners in the absence of a physiologically relevant level of input to the system (i.e., the system of synaptically interconnected neurons of which the neuron of interest is a part). Thus a lack of physiologically relevant level of input to the neuron may be represented by a low frequency single action potential input to the neuron. The AP frequency for the background activity may be 0.5 Hz or less (e.g., 0.4 Hz or less, 0.3 Hz or less, including 0.1 Hz or less). The AP frequency that approximates a response to a physiological relevant level of input to the system may be a burst of 2 or more, 3 or more, (e.g., 4 or more, 5 or more, or 6 or more)

AP being fired at a higher frequency than the background activity, e.g., low frequency single action potential input, where each burst may include APs being fired at a frequency of 100 Hz, and bursts of AP firing may occur at 10-second intervals.

Thus, the reduction in the Pr by the present methods may be input pattern-dependent, i.e., selective for response to background activity, e.g., low frequency single action potential input, and the Pr in response to a more physiologically relevant pattern of AP firing (e.g., burst pattern of AP firing) may not be reduced by the present methods. In some embodiments the Pr in response to a more physiologically relevant pattern of AP firing (e.g., burst pattern of AP firing) is increased (e.g., increased by 10% or more, 20% or more, 30% or more, 50% or more, or 70% or more) compared to before the contacting.

The Pr may be determined at the level of individual pre-synaptic boutons, and may be represented by an average rate over multiple boutons in one or more neuronal dendritic arbors or branches. Determining the Pr may include measuring FM dye (e.g., FM4-64, or FM1-43) uptake due to vesicle turnover from a bouton in response to sequential depolarization of the neuron (e.g., single AP or bursting AP firing). The FM dye uptake is correlated with the Pr.

In certain embodiments, the probability of synaptic release in response to background activity, e.g, low frequency single action potential input, of the neuron is reduced by the present method by about 10% or more, e.g., about 15% or more, about 20% or more, about 30% or more, about 40% or more, about 50% or more, about 60% or more, about 70% or more, about 80% or more, about 90% or more, including about 95% or more. In certain embodiments, the probability of synaptic release in response to background activity, e.g., low frequency single action potential input, of the neuron is reduced by the present method by from about 10% to about 96%, e.g., about 20% to about 95%, about 30% to about 95%, including about 40% to about 90%.

The change in the functional property (e.g., the functional presynaptic terminal density, as described herein) of the neurons may not be accompanied by any substantial increase in synaptogenesis at the synaptic terminals. Synaptogenesis may be measured by, e.g., monitoring the localization of presynaptic proteins, such as synaptophysin, vesicular glutamate transporter (VGLUT), vesicular gamma-aminobutyric acid transporter (VGAT), or Bassoon, by e.g., immunofluorescence staining.

The $[Mg^{2+}]_i$-elevating agent may be any suitable chemical compound that raises $[Mg^{2+}]_i$ of neurons. The $[Mg^{2+}]_i$-elevating agent may increase the level of $[Mg^{2+}]_i$ sufficiently in the neurons to modify one or more functional property of the neurons, as described above. Contacting the agent with the neurons may increase $[Mg^{2+}]_i$ by about 1.1 fold or more, e.g., about 1.2 fold or more, about 1.3 fold or more, 1.4 fold or more, about 1.5 fold or more, about 1.6 fold or more, about 1.7 fold or more, about 1.8 fold or more, about 2 fold or more, about 2.5 fold or more, including about 3 fold or more, relative to the level of $[Mg^{2+}]_i$ before the contacting. In some embodiments, the increase in the level of $[Mg^{2+}]_i$ may be from about 1.1 fold to about 4 fold, e.g., from about 1.2 fold to about 3.5 fold, from about 1.3 fold to about 3.5 fold, from about 1.4 fold to about 3.5 fold, from about 1.5 fold to about 3 fold, from about 1.6 fold to about 2.5 fold, from about 1.6 fold to about 2 fold, including from about 1.8 fold to about 2 fold, relative to the level of $[Mg^{2+}]_i$ before the contacting. The changes in $[Mg^{2+}]_i$ may be measured for in vitro cultured neurons using, e.g., a magnesium-sensitive indicator dye, such as Magnesium Green™-AM.

In some embodiments, the $[Mg^{2+}]_i$-elevating agent provides magnesium (i.e., ionized magnesium) to the extracellular environment of the neuron. In some cases, the agent provides an average extracellular concentration of magnesium of about 0.6 mM or more, e.g., about 0.7 mM or more, about 0.8 mM or more, about 0.9 mM or more, about 1 mM or more, about 1.1 mM or more, including about 1.2 mM or more. In some embodiments, the agent provides an average extracellular concentration of magnesium of from about 0.6 mM to about 1.4 mM, e.g., from about 0.6 mM to about 1.2 mM, from about 0.6 mM to about 1.1 mM, from about 0.6 mM to about 1 mM, including from about 0.6 mM to about 0.9 mM.

In some cases, the $[Mg^{2+}]_i$-elevating agent is a magnesium-containing compound. A magnesium-containing compound of the present disclosure may be any suitable compound for raising $[Mg^{2+}]_i$ of neurons. Suitable magnesium-containing compounds include various magnesium salts, such as, without limitation, magnesium chloride, magnesium sulfate, magnesium oxide. The magnesium-containing compound may be any suitable organic acid magnesium salt, such as a magnesium salt of a non-toxic $C_2$-$C_{12}$ carboxylic acid or a magnesium salt of a non-toxic $C_2$-$C_{12}$ sulfonic acid, for example. Merely by way of example, the magnesium-containing compound may be a magnesium salt of an amino acid (such as magnesium diglycinate), magnesium acetate, magnesium ascorbate, magnesium citrate, magnesium gluconate, magnesium lactate, magnesium malate, magnesium pyrrolidone carboxylate (magnesium pidolate), magnesium taurate, and/or magnesium threonate. Suitable magnesium-containing compounds are described in, e.g., U.S. Application Publication No. 2008/0249170, which is incorporated herein by reference. In some embodiments, the magnesium-containing compound is magnesium threonate (L-TAMS).

In some embodiments, the $[Mg^{2+}]_i$-elevating agent is a compound that targets (e.g., inhibits or activates) a magnesium transport mechanism of the neuron. The magnesium transport mechanism targeted by the agent may be a magnesium transporter, or a magnesium channel. In some embodiments, the agent promotes magnesium influx, from the extracellular space across the plasma membrane, entering the neuron. Suitable magnesium influx promotors include, without limitation, neurotrophic factors such as BDNF, IGFII; and hormones such as growth hormone, estrogen, and insulin. In some embodiments, the agent inhibits magnesium efflux, from the cytosol to the extracellular space across the plasma membrane, of the neuron. Any suitable agent may be used to inhibit magnesium efflux from the neuron. Suitable magnesium efflux inhibitors include, without limitation, imipramine, quinidine and amiloride. In some cases, the agent inhibits a sodium/magnesium antiport activity in the plasma membrane of the neuron.

The $[Mg^{2+}]_i$-elevating agent may be provided in a suitable composition, e.g., a suitable medium, for contacting with the neurons. Where the neurons are cultured in vitro, the composition may be a suitable culture medium or a suitable buffered medium for maintaining the neurons. Thus, in some embodiments, the composition may include a buffered medium, such as, but not limited to, phosphate buffered saline (PBS), Tyrode's buffer, etc. In certain embodiments, the composition may include a culture medium, such as, without limitation, RPMI1640, Minimal essential media (MEM), Eagle's Media, F12, etc., and variants thereof. The composition may further include any suitable supplements, such as, without limitation, serum (e.g., fetal bovine serum (FBS)), amino acids (e.g., L-glutamine), bovine serum albumin (BSA), etc.

Where the neurons are in vivo neurons (e.g., neurons in a brain of an individual), the medium may be an extracellular fluid surrounding the neuron, and the $[Mg^{2+}]_i$-elevating agent may be introduced into the extracellular fluid of the neuron when the agent, or a precursor thereof, is administered to the individual. The extracellular fluid may include, without limitation, interstitial fluid, cerebrospinal fluid, etc.

The amount of the agent that targets a magnesium transport mechanism and provided to the medium in which the neuron resides may vary depending on the specific agent used. In some cases, the agent is provided in the medium at about 0.001 µM or more, e.g., about 0.005 µM or more, about 0.01 µM or more, about 0.05 µM or more, about 0.1 µM or more, about 0.5 µM or more, about 1 µM or more, about 5 µM or more, including about 10 µM or more, and in some cases, is provided in the medium at about 100 µM or less, e.g., about 10 µM or less, about 5 µM or less, about 1 µM or less, about 0.5 µM or less, about 0.1 µM or less, about 0.05 µM or less, about 0.01 µM or less, including about 0.005 µM or less. In some embodiments, the agent is provided in the medium at from about 0.001 µM to about 0.005 µM, from about 0.005 µM to about 0.01 µM, from about 0.01 µM to about 0.05 µM, from about 0.05 µM to about 0.1 µM, from about 0.1 µM to about 0.5 µM, from about 0.5 µM to about 1 µM, from about 1 µM to about 10 µM, or from about 10 µM to about 100 µM.

The neurons may be any suitable type of neurons. In some embodiments the neuron is in, or is derived from, the hippocampus, cortex, thalamus (including the central thalamus), sensory cortex, ventral tegmental area (VTA), prefontal cortex (PFC), nucleus accumbens (NAc), amygdala, substantia nigra, ventral pallidum, globus pallidus, dorsal striatum, ventral striatum, subthalamic nucleus, dentate gyrus, cingulate gyrus, entorhinal cortex, olfactory cortex, primary motor cortex, and/or cerebellum. In some embodiments the neuron is in, or is derived from, the CA1, CA3 and/or dentate gyrus region of the hippocampus.

In some cases, the neurons are cells cultured in vitro, and the contacting includes adding the agent to a culture medium in which the neurons are grown. In some embodiments, the neurons are primary neurons obtained from a brain tissue. In some cases, the primary neurons are dissected from the brain, and dissociated and plated on a suitable support (e.g., a microscope slide, coverslip, bottom of a well of a multi-well plate, etc.). The dissociated neurons may be cultured in vitro for any suitable number of days, e.g., to grow neurites and establish synaptic terminals, e.g., dendritic presynaptic terminals. In certain embodiments, the neurons are cultured in vitro under conditions sufficient for at least some of the neurons to establish synaptic connections to other neurons (i.e., at least some of the neurons are post-synaptically connected).

In some embodiments, the neurons are part of a tissue slice from a brain (e.g., part of an organotypic slice). The brain tissue or brain may be from any suitable model organism, such as, without limitation, a mouse or a rat.

In some embodiments, the neurons are derived from neuronal progenitor cells, i.e., neural stem cells, in which the neural stem cells are differentiated in culture in vitro into neurons and then further cultured for a suitable number of days, e.g., to grow neurites and establish synaptic terminals, e.g., dendritic presynaptic terminals. The source of the neural stem cells can be, but is not limited to, embryonic stem cells (ESCs) derived from the inner cell mass of a blastocyst or umbilical cord, embryonic or post-natal brain, and/or neuronal stem cell lines.

Where the neurons are cultured in vitro, the length of time the neurons are contacted with the medium, as described above, may include a sum of the lengths of time the neurons are contacted over successive exchanges of media having the substantially same amount of the agent, while the neurons are maintaining in culture. The neuron may be contacted with the medium containing the agent in culture for any suitable length of time to modify the functional property of the neurons, e.g., via an increase in the level of $[Mg^{2+}]_i$. In some cases, the neuron is contacted (e.g., contacted substantially continuously) with the medium containing the agent for 1 hour (hr) or more, e.g., 2 hr or more, 3 hr or more, 4 hr or more, 6 hr or more, 9 hr or more, 12 hr or more, 24 hr or more, including 2 days or more, and in some cases, for 1 week or less, e.g., 5 days or less, 3 days or less, 1 day or less, 12 hr or less, 10 hr less, 8 hr or less, 6 hr or less, including 4 hr or less. In some embodiments, the neuron is contacted with the culture medium containing the agent for from 1 hr to 4 hr, from 4 hr to 6, from 6 hr to 8 hr, from 6 hr to 10 hr, from 9 hr to 12 hr, from 12 hr to 1 day, from 24 hr to 3 days, from 2 days to 5 days, or from 2 days to 1 week. Culturing the neuron in the culture medium containing the $[Mg^{2+}]_i$-elevating agent may in some cases include exchanging the culture medium to which the neuron has been exposed for an amount of time (e.g., 1 day or more, 2 days or more, 3 days or more, 5 days or more, or 1 week or more) with a fresh culture medium that includes the $[Mg^{2+}]_i$-elevating agent.

The increase in the level of $[Mg^{2+}]_i$, and/or the modification of the functional property of the neurons, may occur, and/or may substantially be sustained, during the length of time the neurons are contacted with the agent (i.e., in the composition, e.g., medium, containing the agent). In some embodiments, the level of $[Mg^{2+}]_i$ continues to increase (or is maintained at an elevated level), and/or the functional property continues to change (or is maintained at an elevated level), over the time during which the neurons are contacted with the composition, e.g., medium, containing the agent. In some embodiments, the level of $[Mg^{2+}]_i$ continues to increase (or is maintained at an elevated level), and/or the functional property continues to change (or is maintained at an elevated level), for about 2 hr or more, e.g., about 4 hr or more, about 6 hr or more, about 12 hr or more, about 24 or more, about 30 hr or more, about 36 hr of more, including about 48 hr or more while the neurons are contacted with the composition, e.g., medium, containing the agent. In some embodiments, the level of $[Mg^{2+}]_i$ continues to increase (or is maintained at an elevated level), and/or the functional property continues to change (or is maintained at an elevated level) for from about 2 hr to about 48 hr, e.g., from about 4 hr to about 48 hr, including from about 12 hr to about 48 hr while the neurons are contacted with the composition, e.g., medium, containing the agent.

In some cases, the neurons are cells in vivo, e.g., in a brain of an individual, and the contacting involves administering an effective amount of the agent to the individual to provide the extracellular medium of neurons in the brain with an amount of the agent sufficient to modify a functional property of the neurons. The in vivo amount of the agent sufficient to modify the functional property of the neurons may be estimated based on an amount of the agent that is sufficient to modify the functional property of the neurons in culture in vitro.

In some cases, a suitable precursor of the agent (e.g., an inactive precursor, or a precursor with favorable absorption and/or pharmacokinetic profiles) is administered to an individual such that the agent can be delivered to the target site of interest (i.e., the site of the target neurons) in an effective amount. Thus, in some embodiments, the precursor is converted to the active form of the agent in the body when the precursor is administered to an individual.

The administering may be done using any suitable method, and may depend on the $[Mg^{2+}]_i$-elevating agent used. The agent may be administered, e.g., orally, intravenously, intrathecally, etc. The $[Mg^{2+}]_i$-elevating agent may be formulated in any suitable dosage form for administering to the individual. A suitable dosage form for use in the present methods includes an oral dosage form. Suitable oral dosage forms include, without limitation, a liquid form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form, a food form, a chewable form, a non-chewable form, a slow- or sustained-release form, a non-slow- or non-sustained-release from (e.g., immediate release form), and/or the like, may be employed.

The $[Mg^{2+}]_i$-elevating agent may be formulated into any suitable dosage forms for parenteral administration, such as, without limitation, in a pharmaceutically acceptable composition or in a liquid injectable form. A pharmaceutically acceptable composition may include any suitable components, such as, without limitation, pharmaceutically acceptable carriers (e.g., saline), and excipients. The pharmaceutical composition may optionally include other additives (e.g., buffers, stabilizers, preservatives, and the like). Of particular interest in some embodiments are formulations that are suitable for administration to a mammal, particularly those that are suitable for administration to a human.

In some cases, an effective amount of the $[Mg^{2+}]_i$-elevating agent is sufficient to increase the concentration of magnesium in the cerebral spinal fluid of the individual. In some embodiments, the method includes administering (e.g., orally administering) an effective amount of magnesium threonate to the individual to increase mitochondrial density and/or to increase the abundance of one or more $Ca^{2+}$ sensitivity-related proteins in neurons in a region of the brain, compared to a control cohort to which that the magnesium threonate was not administered.

The $[Mg^{2+}]_i$-elevating agent may be administered to the individual at any suitable dose to increase $[Mg^{2+}]_i$ in target neurons of interest of the human individual. In some embodiments, the the $[Mg^{2+}]_i$-elevating agent is administered at about 1 mg/kg/day or more, e.g., at about 10 mg/kg/day or more, at about 20 mg/kg/day or more at about 50 mg/kg/day or more, including at about 100 mg/kg/day or more, and in some embodiments, is administered at about 1,000 mg/kg/day or less, e.g., at about 500 mg/kg/day or less, at about 200 mg/kg/day or less, at about 100 mg/kg/day or less, at about 75 mg/kg/day or less, at about 50 mg/kg/day or less, including at about 30 mg/kg/day. In some embodiments, the $[Mg^{2+}]_i$-elevating agent is administered at from about 1 mg/kg/day to about 30 mg/kg/day, from about 10 mg/kg/day to about 30 mg/kg/day, from about 20 mg/kg/day to about 30 mg/kg/day, from about 20 mg/kg/day to about 50 mg/kg/day, from about 20 mg/kg/day to about 75 mg/kg/day, from about 50 mg/kg/day to about 75 mg/kg/day, from about 50 mg/kg/day to about 100 mg/kg/day, from about 50 mg/kg/day to about 200 mg/kg/day, or from about 100 mg/kg/day to about 1,000 mg/kg/day.

Where the neurons are in a brain, the length of time the neuron is contacted with the composition, e.g., extracellular medium, may refer to the length of the time the $[Mg^{2+}]_i$-elevating agent is administered to the individual, to provide the agent in the composition, e.g., extracellular medium of the neuron. The neuron may be contacted with the composition, e.g., extracellular medium, containing the agent in vivo for any suitable length of time to modify the functional property of the neurons. In some cases, the $[Mg^{2+}]_i$-elevating agent is administered daily, weekly, or monthly. In some cases, the $[Mg^{2+}]_i$-elevating agent is administered for 2 days or more, e.g., 1 week or more, 2 weeks or more, 4 weeks or more, 1 month or more, 2 months or more, 4 months or more, including 6 months or more, and in some cases, for 24 months or less, e.g., 12 months or less, 9 months or less, 6 months or less, 3 months or less, including 1 month or less. In some embodiments, the $[Mg^{2+}]_i$-elevating agent is administered for from 2 days to 1 month, from 1 week to 1 month, from 1 month to 3 months, from 2 months to 6 months, from 4 months to 9 months, from 6 months to 12 months, or from 6 months to 24 months.

The present methods of modifying a function and/or functional property of a neuron mediated by $[Mg^{2+}]_i$ levels, may find use where it is desirable to bring about an increase in functional presynaptic terminal density, an increase in mitochondrial function per unit dendritic area, an increase in abundance of one or more presynaptic $Ca^{2+}$ sensitivity-related proteins and/or a selective reduction in probability of synaptic release in response to background activity, e.g., low frequency single action potential input. Where the neuron is a neuron in vivo, the present methods may find use in treating various neurological disorders, or a symptom thereof, in an individual. The neurological disorder treated by the present methods may be any suitable neurological disorder associated with functional and/or functional synaptic loss, and/or a sustained and/or elevated spontaneous activity of neurons.

Neurological disorders, or symptoms thereof, associated with sustained and/or elevated spontaneous activity of neurons and that may be treated by the present methods include, without limitation, seizure, epilepsy, Alzheimer's disease, cerebral palsy, chronic pain, involuntary muscular contractions and convulsive twitches, spasm, wrinkling, dystonia and tremor, anxiety and depression associated with sustained neural activity in prefrontal cortex (PFC) and amygdala, and insomnia.

In some embodiments, the neurological disorder, or a symptom thereof, is associated with insufficient synaptic density in one or more brain regions of an individual. In some embodiments, the neurological disorder, or symptom thereof, includes Alzheimer's disease, mild cognitive impairment (MCI), dementia, Huntington's disease, autism, schizophrenia, cognitive decline as secondary effect of disease or medical treatment, depression, sleep disorder, anxiety, attention deficit hyperactivity disorder (ADHD), migraine, headache, stroke, and neuropathy.

Screening Methods

The present disclosure includes screening methods for identifying agents, i.e., active agents, that modify a functional property of neurons, as described above, e.g., by screening for a $[Mg^{2+}]_i$-elevating agent. Thus, provided herein is a method of identifying an active agent that modifies a functional property of a neuron, the method including contacting a population of neurons in vitro with a candidate agent, and measuring the level of intracellular magnesium in one or more subcellular regions of the neurons after the contacting. An agent that raises $[Mg^{2+}]_i$ above a reference level may be a candidate for an active agent for modifying a functional property of neurons, where the change in the functional property that is induced by the active agent is dependent on the increase in $[Mg^{2+}]_i$ of the neuron in which $[Mg^{2+}]_i$ is increased. The functional property which the candidate agent is determined to be an active agent for modifying may be any suitable functional property, as described above (e.g., a functional presynaptic terminal density, a mitochondrial function per unit dendritic area, an abundance of one or more presynaptic $Ca^{2+}$ sensitivity-related proteins, and/or probability of synaptic release in response to background activity, e.g., low frequency single action potential input). In general, an active agent suitable for modify a functional property of neurons, as described herein, may be non-toxic to the neurons when used at the effective dose.

The intracellular magnesium level may be measured using a magnesium indicator dye (i.e., a chemical compound that has measurable optical properties that changes based on the local concentration of ionized magnesium). The magnesium indicator dye may be any suitable dye whose optical properties are altered by the local concentration of ionized magnesium in the cell. Suitable magnesium indicator dyes include, without limitation, Magnesium Green™, Mag-Fura-2, Fluo-2 Mg, Magnesium Red™, and Indo-1 Mg.

The neurons of the population may be any suitable neurons cultured in vitro, such as primary neurons, as described above, or neurons in tissue (i.e., in vivo). In some embodiments, the neurons of the population may be derived from (i.e., differentiated from) neuronal progenitor cells, e.g., stem cells, neuronal cell lines, etc. In certain embodiments, the neurons are cultured in vitro under conditions sufficient for at least some of the neurons to establish dendritic presynaptic terminals and/or synaptic connections to other neurons (i.e., at least some of the neurons are post-synaptically connected).

Generally, the measuring may include using fluorescence microscopy. In some embodiments, the measuring may include illuminating the neuron, or the subcellular region thereof, with a light stimulus in a manner sufficient to excite the magnesium indicator dye at its excitation wavelength, and detecting a magnesium concentration-dependent fluorescence emitted by the magnesium indicator dye with a light detector (e.g., an image detector, or a photodetector).

The subcellular regions in which the level of intracellular magnesium measured may be any suitable subcellular region for estimating the level of intracellular magnesium in the neurons. In some cases, the subcellular region is a neuronal branch (e.g., a branch of a neurite, such as a dendrite or an axon). Where the subcellular region is a neuronal branch, the measuring may include measuring from each branch, an average level of fluorescence emitted by the magnesium indicator dye when the subcellular region is illuminated by a suitable light, the diameter of the branch, and calculating the level of intracellular magnesium based on the diameter and the average fluorescence level in each branch. In some cases, the calculating includes calculating a mean intensity of fluorescence per pixel of the branch, and dividing the mean intensity with the diameter of the branch. The calculated level of intracellular magnesium maybe proportional to the intracellular magnesium concentration.

Each subcellular region in which the intracellular magnesium concentration is measured may have a length scale that is suitable for estimating the average intracellular magnesium concentration across the subcellular region. In certain embodiments, the subcellular region has a length of about 1 μm or more, e.g., about 2 μm or more, about 3 μm or more, about 5 μm or more, about 10 μm or more, about 20 μm or more, about 30 μm or more, about 50 μm or more, including about 100 μm or more, and in some embodiments, may have a length of about 1,000 μm or less, e.g., about 500 μm or less, about 200 μm or less, about 100 μm or less, about 50 μm or less, about 20 μm or less, about including about 10 μm or less. In some embodiments, the subcellular region has a length of from about 1 μm to about 1,000 μm, e.g., from about 2 μm to about 500 μm, from about 3 μm to about 200 μm, from about 5 μm to about 100 μm, including from about 10 μm to about 50 μm.

The number of subcellular regions, e.g., neuronal branches, measured may be any suitable number for estimating the average intracellular magnesium concentration of the neurons. In some embodiments, the number of subcellular regions measured is 10 or more, e.g., 20 or more, 30 or more, 40 or more, 50 or more, 100 or more, 150 or more, 200 or more, 300 or more, 400 or more, 500 or more, including 1,000 or more, and in some cases, is 100,000 or less, e.g., 50,000 or less, 10,000 or less, 5,000 or less, 1,000 or less, including 500 or less. In some embodiments, the number of subcellular regions measured is in the range of 10 to 10,000, e.g., 20 to 50,000, 30 to 10,000, 40 to 5,000, 50 to 1,000, 100 to 1,000, including 100 to 500.

The reference level may be any suitable level for identifying an active agent for modifying a functional property of neurons. In some cases, the reference level is derived from the baseline level of intracellular magnesium obtained from the same subcellular region before the contacting. In some cases, the reference level is 10% or more, e.g., 30% or more, 50% or more, 70% or more, including 100% or more above the baseline level. In some embodiments, the reference level is above the baseline level by from 10% to 100%, e.g., from 30% to 100%, from 50% to 100%, including from 70% to 100%. In certain embodiments, the reference level is based on a standard deviation of the measurements of the baseline level of intracellular magnesium. In some embodiments, the reference level is 1 times or more, e.g., 1.2 times or more, 1.5 times or more, 2 times or more, including 3 times the standard deviation of the measurements of the baseline level of intracellular magnesium. In some embodiments, the reference level is from 1 times to 3 times, e.g., from 1.2 times to 3 times, including from 1.5 times to 2 times the standard deviation of the measurements of the baseline level of intracellular magnesium.

In certain embodiments, the reference level is derived from a control level of intracellular magnesium in a negative control neuron that has not been contacted with the agent (e.g., contacted with a composition, e.g., medium, that has no agent).

The candidate agents of the present screening methods may be any suitable chemical compound for determining its ability to raise $[Mg^{2+}]_i$ and modify a functional property of neurons. The candidate agent may be among a library of chemical compounds in a screening library. The candidate agent may be chemical derivatives of a parent compound (e.g., a lead compound) whose ability to modify a functional property of neurons may or may not be known. The candidate agent may be an activator, or an inhibitor of activity of a cellular target in the neuron (e.g., a target protein, enzyme, ion channel, plasma membrane transporter, signaling molecule, transcription factor, etc.) In some cases, the candidate agent modulates the activity of an ion channel. In some cases, the candidate agent modulates the activity of a plasma membrane transporter (e.g., a magnesium transporter, including a uniporter, a cotransporter, an antiporter, etc.)

The present method may further include measuring changes to one or more (e.g., two or more, three or more, or all four) functional properties of the neurons before and after contacting with the candidate agent. In some cases, the candidate agent is determined to be an active agent for modifying a functional property of neurons if there is a change in the one or more functional properties of the neurons after the contacting compared to before the contacting. Measuring changes to one or more functional properties of the neurons may be performed on a second population of neurons that are similar in origin to the population of neurons that were tested for the agent's ability to raise $[Mg^{2+}]_i$, as described above.

The functional properties measured in the present methods may be any suitable functional property, as described above. In some cases, the functional property is functional presynaptic terminal density. In some cases, the functional property is mitochondrial function per unit dendritic area. In some cases, the functional property is probability of synaptic release in response to background activity, e.g., low frequency single action potential input.

Methods for Reducing a Cognitive Impairment

Also provided herein is a method of reducing a cognitive impairment in a human individual. The present method may include administering an effective amount of magnesium threonate to a human individual having or suspected of having cognitive impairment, where the effective amount is sufficient to reduce a functional age of the brain of the human individual. The functional age of the brain may be determined based on the individual's performance on an appropriate cognitive test, such as the Trail Making Test—Part B (TMT-B) (Arbuthnott et al., (2000) *J Clin Exp Neuropsychol* 22, 518-528). The individual's performance on the cognitive test may be compared to a standard curve of performance against age in a cohort of individuals with clinically normal cognitive function, where the functional age of the individual's brain is the age on the standard curve that corresponds to the performance level of the individual.

The human individual may be an individual having or suspected of having cognitive impairment. In some embodiments, cognitive impairment in an individual may be determined subjectively, based on, e.g., subjective memory complaints, sleep disorder and/or anxiety. In some embodiments, an individual having or suspected of having cognitive impairment may have an objective cognitive deficit, but not have dementia, e.g., as determined by a Mini-Mental State Examination score equal to or greater than 24. In some embodiments, an individual having or suspected of having cognitive impairment may have a sleep disorder, such as difficulty in sleeping, e.g., as determined by a Pittsburgh Sleep Quality Index greater than 5. In some embodiments, an individual having or suspected of having cognitive impairment may have mild-to-moderate anxiety, e.g., as determined by a Hamilton Anxiety Questionnaire sub-score A of from 12 or greater to 28 or less.

In some embodiments, cognitive impairment in an human individual may be determined objectively using one or more cognitive tests, such as a test for executive function (e.g., TMT-B); working memory (e.g., DigitSpan Test); working memory (e.g., Eriksen Flanker Congruent/Incongruent Test); and hippocampal-dependent episodic memory (e.g. the Face-Name Association Test). In some cases, the cognitive ability of the human individual is assessed by a composite z score of performance in multiple cognitive tests (such two, three or all four of the cognitive tests described above).

In some cases, a human individual having cognitive impairment has a functional brain age, as determined using the TMT-B test, about 5 years or more older, e.g., about 6 years or more older, about 7 years or more older, about 8 years or more older, about 9 years or more older, about 10 years or more older, including about 11 years or more older than the average functional brain age of cognitively normal individuals of the same age. In some embodiments, an human individual having cognitive impairment has a functional brain age, as determined using the TMT-B test, from about 5 years to about 20 years older, e.g., from about 6 years to about 15 years older, from about 7 years to about 14 years older, from about 8 years to about 13 years older, including from about 9 years to about 12 years older than the average functional brain age of cognitively normal individuals of the same age.

In some embodiments, the cognitive impairment includes a fluctuation in cognitive ability, e.g., as measured by one or more of the cognitive tests as described above. The cognitive fluctuation may be assessed by calculating the variance over time in one or more cognitive scores using the cognitive tests as described above. In some cases, the cognitive fluctuation is assessed by calculating the variance over time in a composite z score of performance in multiple cognitive tests.

In some embodiments, the human individual is diagnosed with a neurological disorder, such as, but not limited to, mild cognitive impairment (MCI), age-related cognitive decline or Alzheimer's disease. In some cases the cognitive impairment is a magnesium deficiency-caused neurological disorder (such as, without limitation, attention deficit hyperactivity disorder (ADHD)).

The human individual may be any suitable age. In some cases, the individual is about 45 years old or older, e.g., about 47 years old or older, about 50 years old or older, about 52 old years or older, including about 55 old years or older, and in some cases, may be about 80 years old or younger, e.g., about 77 years old or younger, about 75 years old or younger, about 72 years old or younger, about 70 years old or younger, including about 65 years old or younger. In some embodiments, the individual is from about 45 years old to about 80 years old, e.g., from about 47 years old to about 77 years old, from about 50 years old to about 75 years old, from about 50 years old to about 72 years old, including from about 50 years old to about 70 years old.

"Magnesium theronate" as used herein, may refer to a chemical compound represented by formula (I):

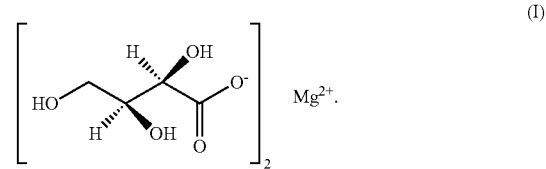

In some embodiments, the magnesium threonate may be provided as a precursor molecule. A magnesium threonate precursor may include a molecule or a combination of molecules that can be readily converted to magnesium threonate, as a result of ionization, oxidation, reduction, or hydrolysis, etc., with or without the aid of an enzyme, when the composition is dissolved in an aqueous medium or administered to an individual. A magnesium threonate precursor may include a theronate precursot. A suitable threonate precursor may include, without limitation, threonic acid, an ester derivative of threonic acid or threonate (e.g., where one or more hydroxyl groups and/or the carboxylic acid group forms an ester), a lactonized threonic acid (e.g., threonic acid-1,4-lactone), ascorbic acid or a salt thereof, or a derivative thereof, etc.

The magnesium threonate may be formulated in a suitable dosage form for administering to the individual. A suitable dosage form for use in the present methods includes an oral dosage form. Suitable oral dosage forms include, without limitation, a liquid form, a gel form, a semi-liquid (for example, a liquid, such as a viscous liquid, containing some solid) form, a semi-solid (a solid containing some liquid) form, and/or a solid form, for example. Merely by way of example, a tablet form, a capsule form, a food form, a chewable form, a non-chewable form, a slow- or sustained-release form, a non-slow- or non-sustained-release from (e.g., immediate release form), and/or the like, may be employed. Gradual-release tablets are known in the art. Examples of such tablets are set forth in U.S. Pat. No. 3,456,049, which is incorporated herein by reference. The dosage form may take the form of a food form, e.g., a food bar, a cereal product, a bakery product, a dairy product, and/or the like. The dosage form may take the form of a bakery form, e.g., a bread-type product, such as a bagel or bread itself, for example, a donut, a muffin, and/or the like.

The magnesium threonate, when provided in a liquid form may be used in any suitable manner. In some embodiments, the magnesium threonate dosage form may be used as a beverage, such as a milk-based beverage, a sports drink, a fruit juice drink, an alcoholic beverage, and/or the like. In still other embodiments, the magnesium threonate dosage form in a liquid form may include water, and magnesium threonate, and optionally, at least one agent, sufficient to confer a suitable property to the product. In still another embodiment, a magnesium threonate dosage form in a liquid form may be formulated from a dry mix, such as a dry beverage mix or a magnesium-fortified, milk-comprising powder. A dry mix may be suitable in terms of transportation, storage, and/or shelf life. The composition may be formulated from the dry mix in any suitable manner, such as by adding a suitable liquid (e.g., water, milk, fruit juice, alcohol, etc.).

The magnesium threonate may be administered to the human individual at any suitable dose to reduce a functional age of the brain of the human individual. In some embodiments, the magnesium threonate is administered at from about 20 mg/kg/day to about 50 mg/kg/day, e.g., from about 20 mg/kg/day to about 45 mg/kg/day, from about 20 mg/kg/day to about 40 mg/kg/day, from about 20 mg/kg/day to about 35 mg/kg/day, from about 20 mg/kg/day to about 34 mg/kg/day, from about 20 mg/kg/day to about 33 mg/kg/day, from about 20 mg/kg/day to about 32 mg/kg/day, from about 20 mg/kg/day to about 31 mg/kg/day, including from about 20 mg/kg/day to about 30 mg/kg/day. In some embodiments, the magnesium threonate is administered at about 25±5 mg/kg/day.

The present method may include administering the magnesium threonate for any length of time sufficient to reduce a functional age of a brain of the human individual. In some embodiments, the magnesium threonate is administered for 6 days or more, e.g., 1 week or more, 1.5 weeks or more, 2 weeks or more, 3 weeks or more, 6 weeks or more, 9 weeks or more, 12 weeks or more, 6 months or more, 12 months or more, 18 months or more, including 24 months or more, and in some cases, is administered for 10 year or less, e.g., 5 years or less, 2 years or less, 1 year or less, 9 months or less, 6 months or less, including 12 weeks or less. In some embodiments, the magnesium threonate is administered from 6 days to 10 years, e.g., from 1 week to 5 years, from 2 weeks to 2 years, from 3 weeks to 1 year, from 6 weeks to 6 months, including from 6 weeks to 12 weeks.

The present methods of treating an individual for cognitive impairment by administering magnesium threonate may have a beneficial effect on the cognitive function of the individual. In particular, the present methods may reduce deficit in the functional age of the brain, e.g., as assessed by TMT-B described above, of the individual. In some cases, the functional age is reduced by about 5 years or more, e.g., about 7 years or more, about 10 years or more, about 15 years or more, about 20 years or more, including about 30 years or more, compared to the functional age of the brain of the individual before the administering. In certain embodiments, the functional age is reduced by from about 5 years to about 50 years, e.g., from about 5 years to about 45 years, from about 5 years to about 40 years, including from about 5 years to about 35 years.

Methods for Evaluating a Response to Treatment for a Neurological Disorder

Further aspects of the present disclosure include a method for evaluating a response to treatment for a neurological disorder (e.g., cognitive impairment), such as response to treatment with magnesium threonate, as described above. In general terms, the present method may include administering a $[Mg^{2+}]_i$-elevating agent, e.g., a magnesium-containing compound, to an individual having or suspected of having a neurological disorder (e.g., cognitive impairment); and determining a level of magnesium in blood cells (i.e., ionized or total intracellular magnesium) of a first blood sample obtained from the individual before the administering. The method may further include evaluating a change in cognitive competency of the individual before and after the administering. In some embodiments, a level of magnesium in blood cells of a second blood sample may be obtained from the individual after the administering.

A comparison of the level of magnesium in the blood cells from before the administering to the level after the administering may provide an indication as to how well the individual will respond, or is responding to a treatment of the neurological disorder (e.g., cognitive impairment) by administering a $[Mg^{2+}]_i$-elevating agent. Without being bound to theory, it is believed that the level of magnesium in the blood cells is correlated with intracellular ionized magnesium concentration in brain neurons and/or the concentration of ionized magnesium in cerebral spinal fluid of the individual, and the intracellular ionized magnesium concentration in brain neurons and the concentration of ionized magnesium in cerebral spinal fluid further affect functional properties of brain neurons. In other words, the change in the level of magnesium in the blood cells during the course of treatment of the neurological disorder (e.g., cognitive impairment) by administering a $[Mg^{2+}]_i$-elevating agent, such as magnesium threonate, may serve as a biomarker for assessing responsiveness of brain neurons of an individual to the treatment. Thus, the change in the level of magnesium in the blood cells, e.g., red blood cells, may be a marker for identifying which patient responds or will respond to the treatment for neurological disorder by administering a $[Mg^{2+}]_i$-elevating agent, that may inform the decision to continue or discontinue the treatment. In some cases, the decision to continue or discontinue the treatment may be made in the absence of an improvement in cognitive competency of the individual.

Figure 27:
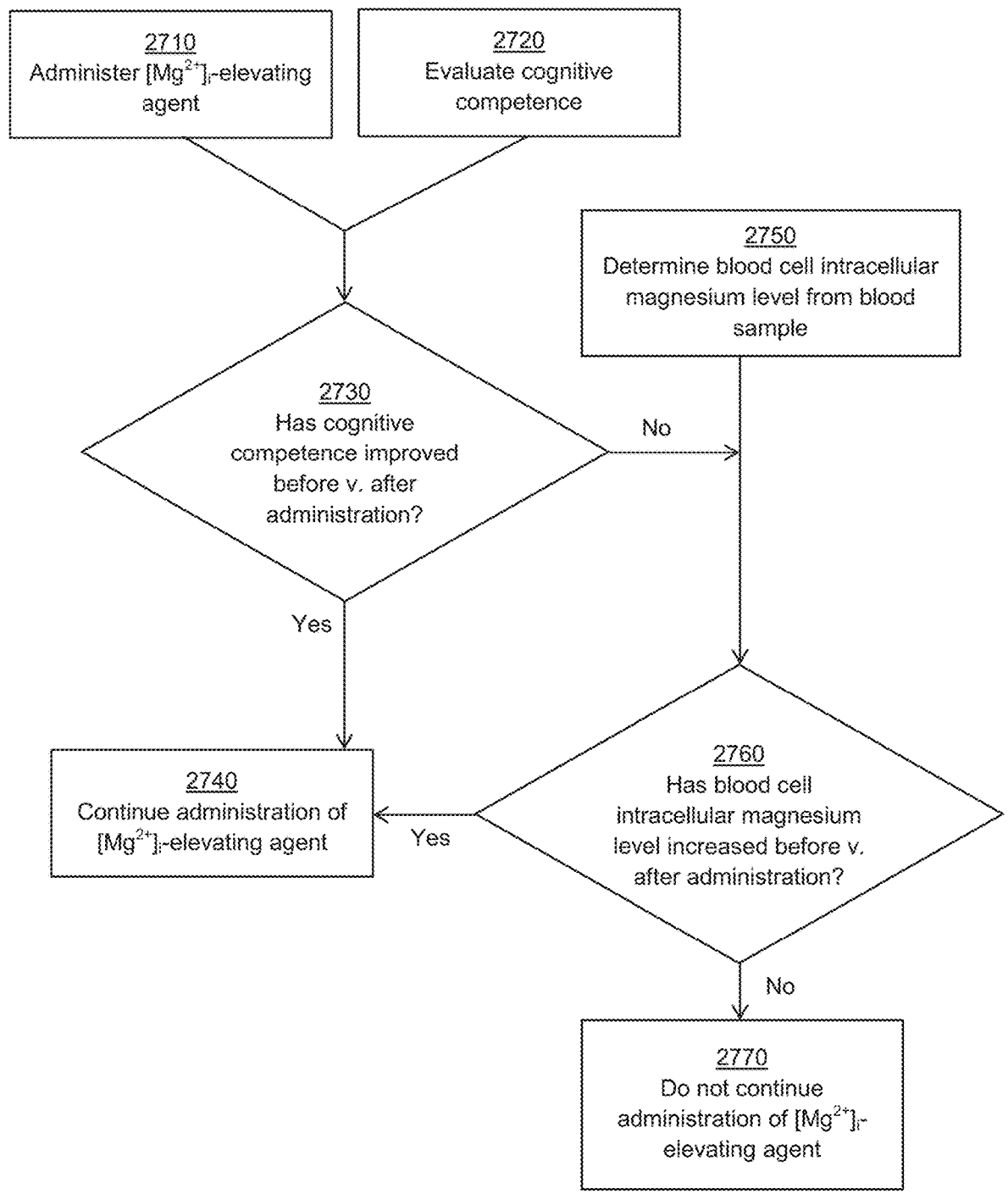
FIG. 27 is a schematic diagram showing a flow chart for a method of determining the amenability of an individual for treatment of a neurological disorder with a $[Mg^{2+}]_i$-elevating agent, according to embodiments of the present disclosure.

An embodiment of the present method may be further described with reference to FIG. 27. As described above, the method may include administering 2710 to an individual having, or suspected of having, a neurological disorder, e.g., cognitive impairment, a $[Mg^{2+}]_i$-elevating agent, e.g., magnesium-containing compound, and evaluating 2720 a cognitive competence of the individual, e.g., by administering a cognitive test to the individual, in a manner sufficient to determine 2730 whether the administration of the $[Mg^{2+}]_i$-elevating agent has improved the individual's cognitive competence. In some embodiments, if the individual's cognitive ability based on the cognitive test increases after the initial administration (e.g., administration for 6 weeks or more, for 12 weeks or more, etc.) of the $[Mg^{2+}]_i$-elevating agent, the treatment with the $[Mg^{2+}]_i$-elevating agent may be continued 2740. In some embodiments, the method includes determining 2750 the intracellular level of magnesium in blood cells of a blood sample in a manner sufficient to determine 2760 whether the administration of the $[Mg^{2+}]_i$-elevating agent has increased the intracellular level of magnesium in the blood cells in the individual. Thus, even if the individual's cognitive ability does not significantly increase after the initial administration of the $[Mg^{2+}]_i$-elevating agent the treatment with the $[Mg^{2+}]_i$-elevating agent may be continued 2740 when there is an increase in the individual's magnesium level in the blood cells over a comparable time period of administering the $[Mg^{2+}]_i$-elevating agent. In some embodiments, if the individual's cognitive ability based on the cognitive test does not increase after the initial administration of the $[Mg^{2+}]_i$-elevating agent and there is no significant increase in the individual's magnesium level in the blood cells over a comparable time period, the treatment with the $[Mg^{2+}]_i$-elevating agent may not be continued 2770.

In some embodiments, if the individual's cognitive ability based on the cognitive test increases after the initial administration (e.g., administration for 6 weeks or more, for 12 weeks or more, etc.) of the $[Mg^{2+}]_i$-elevating agent, e.g., magnesium-containing compound, but there is no significant increase in the individual's magnesium level in the blood cells over a comparable time period, the treatment with the $[Mg^{2+}]_i$-elevating agent may be continued.

The present method may employ any suitable combination of the level of magnesium in blood cells of the individual, and the cognitive competency of the individual to inform subsequence treatment options for the individual. In certain embodiments, the method includes obtaining a second blood sample from the individual after the administering. In certain embodiments, the method includes obtaining a second blood sample from the individual after the administering only when there is no improvement in cognitive competency of the individual from before to after the administering.

In some embodiments, the present method further includes continuing treatment of the individual with the $[Mg^{2+}]_i$-elevating agent, e.g., magnesium-containing compound, for the neurological disorder (e.g., cognitive impairment) if the intracellular magnesium concentration of the blood cells increases after the initial administration (e.g., for 6 weeks or more, 12 weeks or more, etc., as described below) compared to the intracellular magnesium concentration before the initial administration. The increase in the intracellular magnesium concentration of the blood cells after the initial administration of the $[Mg^{2+}]_i$-elevating agent may vary depending on the individual, and the intracellular magnesium concentration after the initial administration may be greater by about 5% or more, e.g., by about 7% or more, by about 10% or more, including by about 15% or more compared to the intracellular magnesium concentration before the initial administration. In some embodiments, the intracellular magnesium concentration after the initial administration may be greater by from about 5% to about 20%, e.g., from about 7% to about 20%, including from about 10% to about 20%, compared to the intracellular magnesium concentration before the initial administration.

Continuing treatment of the individual with the $[Mg^{2+}]_i$-elevating agent, e.g., magnesium-containing compound, for the neurological disorder (e.g., cognitive impairment) after the initial treatment may also depend on whether the individual shows improvement in cognitive function, whether or not an increase in the individual's magnesium level in the blood cells was concurrently detected. Thus, in some embodiments, the present method includes administering a cognitive test before and/or after administering the $[Mg^{2+}]_i$-elevating agent to evaluate the cognitive competency of the individual. If the individual's cognitive ability based on the cognitive test increases after administration of the $[Mg^{2+}]_i$-elevating agent, the treatment with the $[Mg^{2+}]_i$-elevating agent may be continued.

In some embodiments, the improvement in cognitive competency may be about 10% or more, e.g., 15% or more, 20% or more, 25% or more, 30% or more, 45% or more, 50% or more, including 60% or more above the baseline cognitive competency of the individual established before administering the $[Mg^{2+}]_i$-elevating agent, e.g., magnesium-containing compound. In some embodiments, the improvement in cognitive competency may be from about 10% to about 100%, e.g., from about 10% to about 75%, from about 10% to about 60%, including from about 10% to about 50% above the baseline cognitive competency of the individual established before administering the $[Mg^{2+}]_i$-elevating agent.

The level of magnesium in blood cells of a blood sample from the individual may be determined using any suitable method. In some embodiments the level of magnesium in blood cells of a blood sample is determined by measuring the magnesium level in blood cells from a sample obtained from the individual. The level of magnesium is obtained from a blood sample that is obtained from the individual within a suitable time frame relative to the administration. In certain embodiments, the blood sample is obtained from the individual before the administration, when the individual has, or is suspected of having, the neurological disorder for which treatment is sought. In some embodiments, the blood sample may be obtained at the time of the administration of the $[Mg^{2+}]_i$-elevating agent, e.g., magnesium-containing compound, or may be obtained 6 week or less before, e.g., 3 weeks or less before, 1 week or less before, 5 days or less before, 3 days or less before, 2 days or less before, 1 day or less before, 12 hours or less before, 6 hours or less before, 3 hours or less before, 1 hour or less before, 30 min or less before, 15 min or less before, including 5 min or less before the administering.

In certain embodiments, the blood sample is obtained from the individual after the administering of the $[Mg^{2+}]_i$-elevating agent, e.g., magnesium-containing compound, (e.g., after administering a dosage regimen). In some embodiments, the blood sample may be obtained at the time of completing the dosage regimen or later, or may be obtained 5 min or more after, e.g., 15 min or more after, 30 min or more after, 1 hour or more after, 3 hours or more after, 6 hours or more after, 12 hours or more after, 1 day or more after, 2 days or more after, 3 days or more after, 5 days or more after, and up to 1 week after completing the dosage regimen. In certain embodiments, the blood sample may be obtained after evaluating the change in cognitive competency from before to after the administering. In some embodiments, the blood sample may be obtained at the time of evaluating the change in cognitive competency or later, or may be obtained 5 min or more after, e.g., 15 min or more after, 30 min or more after, 1 hour or more after, 3 hours or more after, 6 hours or more after, 12 hours or more after, 1 day or more after, 2 days or more after, 3 days or more after, 5 days or more after, and up to 1 week after evaluating the change in cognitive competency from before to after the administering.

Determining the level of magnesium in blood cells of a blood sample may be done using any suitable method. The blood cells may include any suitable blood cells, such as, but not limited to, red blood cells, lymphocytes, or platelets. The present methods may include measuring the level of magnesium (e.g., the concentration of intracellular magnesium) in the blood cells. In some cases, the method may include separating the blood cells (e.g., red blood cells) from plasma, and measuring the level of magnesium in the separated blood cells. In some embodiments, the separated blood cells are lysed to extract the intracellular content. The measuring may be done using any suitable technique, such as, without limitation, flow cytometry, a photometric method, thin film reflectance photometry, atomic absorption spectrometry (AAS), and ion-selective electrode detection. In some embodiments, the measuring is done using inductively coupled plasma-mass spectrometry (ICP-MS), or particle induced x-ray emission (PIXE). In certain embodiments, the method includes measuring the ionized magnesium in a cell by labeling the cells with a membrane-permeable magnesium indicator dye, and measuring the level of fluorescence in individual labeled cells using flow cytometry. In some cases, the magnesium level is measured using a metallochromic indicator dye (such as, without limitation, calmagite, xylidyl blue or magon, chlorophosphonazo III and arsenazol) that selectively bind to magnesium and change color upon binding. In some cases, a formazan dye that forms a complex with magnesium may be used, e.g., with thin film reflectance photometry.

In certain embodiments, the neurological disorder being treated according to the present methods may be a magnesium deficiency-caused neurological disorder (such as, without limitation, attention deficit hyperactivity disorder (ADHD)). In certain embodiments, the neurological disorder being treated according to the present methods is a neurological disorder associated with sustained and/or elevated spontaneous activity of neurons, including, without limitation, seizure, epilepsy, Alzheimer's disease, cerebral palsy, chronic pain, involuntary muscular contractions and convulsive twitches, spasm, wrinkling, dystonia and tremor, anxiety and depression associated with sustained neural activity in prefrontal cortex (PFC) and amygdala, and insomnia.

In some embodiments, the neurological disorder is caused by insufficient synaptic density in one or more brain regions of the individual. In some embodiments, the neurological disorder includes Alzheimer's disease, mild cognitive impairment (MCI), age-related cognitive decline or dementia, Huntington's disease, autism, schizophrenia, cognitive decline as secondary effect of disease or medical treatment, depression, sleep disorder, anxiety, attention deficit hyperactivity disorder (ADHD), migraine, headache, stroke, and neuropathy.

The $[Mg^{2+}]_i$-elevating agent may be any suitable compound that increases the intracellular magnesium of neurons and may be administered to an individual for treatment of a neurological disorder (e.g., cognitive impairment). In some embodiments, the $[Mg^{2+}]_i$-elevating agent may be a compound that is capable of elevating intracellular magnesium concentration in neurons but does not include magnesium, such as, without limitation, inhibitors or activators of magnesium ion transport across the plasma membrane, as described herein.

In some embodiments, the $[Mg^{2+}]_i$-elevating agent is a magnesium-containing compound. Suitable magnesium-containing compounds include various magnesium salts, such as, without limitation, magnesium chloride, magnesium sulfate, magnesium oxide. The magnesium-containing compound may be any suitable organic acid magnesium salt, such as a magnesium salt of a non-toxic $C_2$-$C_{12}$ carboxylic acid or a magnesium salt of a non-toxic $C_2$-$C_{12}$ sulfonic acid, for example. Merely by way of example, the magnesium-containing compound may be a magnesium salt of an amino acid (such as magnesium diglycinate), magnesium acetate, magnesium ascorbate, magnesium citrate, magnesium gluconate, magnesium lactate, magnesium malate, magnesium pyrrolidone carboxylate (magnesium pidolate), magnesium taurate, and/or magnesium threonate. Suitable magnesium-containing compounds are described in, e.g., U.S. Application Publication No. 2008/0249170, which is incorporated herein by reference. In some embodiments, the magnesium-containing compound is magnesium threonate.

The $[Mg^{2+}]_i$-elevating agent, e.g., magnesium-containing compound, may be administered using any suitable method, and in some cases, may be administered orally, intravenously, intrathecally, etc. The $[Mg^{2+}]_i$-elevating agent may be formulated in a suitable dosage form for administering to the individual, as described above.

The $[Mg^{2+}]_i$-elevating agent, e.g., magnesium-containing compound, may be administered for any suitable length of time to evaluate a response to treatment of the neurological disorder (e.g., cognitive impairment). In some embodiments, the $[Mg^{2+}]_i$-elevating agent is administered for 9 days or more, e.g., 2 weeks or more, or more, 3 weeks or more, 6 weeks or more, 9 weeks or more, including 12 weeks or more, and in some cases, is administered for 1 year or less, e.g., 9 months or less, 6 months or less, including 12 weeks or less. In some embodiments, the $[Mg^{2+}]_i$-elevating agent is administered from 9 days to 1 year, e.g., from 2 weeks to 9 months, from 3 weeks to 6 months, including from 6 weeks to 12 weeks.

The $[Mg^{2+}]_i$-elevating agent, e.g., magnesium-containing compound, may be administered to the individual at any suitable dose to evaluate a response to treatment of the neurological disorder (e.g., cognitive impairment). In some embodiments, the $[Mg^{2+}]_i$-elevating agent is administered at from about 5 mg/kg/day to about 50 mg/kg/day, e.g., from about 10 mg/kg/day to about 45 mg/kg/day, from about 15 mg/kg/day to about 40 mg/kg/day, including from about 20 mg/kg/day to about 35 mg/kg/day. In some embodiments, the $[Mg^{2+}]_i$-elevating agent is a magnesium-containing compound, such as magnesium threonate, and is administered at about 25±5 mg/kg/day. The $[Mg^{2+}]_i$-elevating agent may be administered daily, every other day, every third day, every 5 days, etc.

The cognitive test may be any suitable cognitive test for testing, e.g., executive function, working memory, language, or episodic memory. In some cases, the test for executive function includes TMT-B. In some embodiments, the test for working memory includes DigitSpan test. In some embodiments, the test for working memory includes the Eriksen Flanker Congruent/Incongruent Test. In some embodiments, the test for episodic memory includes the Face-Name Association Test. One or more of the cognitive tests may be administered to the individual to obtain a measure of the individual's cognitive competence. In some embodiments, results of multiple tests (e.g., 2 or more, 3 or more, or 4 tests)

are combined into a composite score, where the composite score provides a measure of the individual's cognitive competence. In some embodiments, the test for global cognitive ability includes the Mini-Mental Status Examination (MMSE).

In some embodiments, the administration is sufficient to improve cognitive competency by about 10% or more, e.g., 15% or more, 20% or more, 25% or more, 30% or more, 45% or more, 50% or more, including 60% or more above the baseline cognitive competency of the individual established before administering the $[Mg^{2+}]_i$-elevating agent, e.g., magnesium-containing compound. In some embodiments, the administration is sufficient to improve cognitive competency by from about 10% to about 100%, e.g., from about 10% to about 75%, from about 10% to about 60%, including from about 10% to about 50% above the baseline cognitive competency of the individual established before administering the $[Mg^{2+}]_i$-elevating agent.

Where the method includes continuing administering the $[Mg^{2+}]_i$-elevating agent, e.g., magnesium-containing compound, after an initial administration of the $[Mg^{2+}]_i$-elevating agent, e.g., as determined by the improvement in cognitive competency and/or an increase in the level of magnesium in blood cells from before to after the initial administration, the continued administration of the $[Mg^{2+}]_i$-elevating agent improves cognitive competency by about 10% or more, e.g., 15% or more, 20% or more, 25% or more, 30% or more, 45% or more, 50% or more, including 60% or more above the baseline cognitive competency of the individual established before the initial administration, or after the initial administration but before the continued administration. In some embodiments, the administration of the $[Mg^{2+}]_i$-elevating agent improves cognitive competency by from about 10% to about 100%, e.g., from about 10% to about 75%, from about 10% to about 60%, including from about 10% to about 50% above the baseline cognitive competency of the individual established before the initial administration, or after the initial administration but before the continued administration. Thus, in some cases, the method may further include evaluating the cognitive competency of the individual after the continued administration of the $[Mg^{2+}]_i$-elevating agent.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Regulation of Functional Density of Functional Terminal Density, Mitochondria Function/Density and Terminal Ca-Sensitivity Related Proteins of Neurons by Change in $[Mg^{2+}]_i$ Materials and Methods
Imaging and Analysis Most of the in vitro fluorescent or differential interference contrast (DIC) images for an area of interest (AOI) (59 μm×59 μm) were taken at 1024×1024 pixels with a 0.05754 μm/pixel resolution using a 60×NA1.20 water-immersion objective on a Laser Scanning Confocal Microscopy System FV300 (Olympus) at room temperature (RT, 22-26° C.), the exceptions were clarified in the following methods. A z-stack of images was taken with 0.5-1 μm steps and compressed at maximal intensity to generate the final image, which was then processed and analyzed in Image-Pro Plus 5.0 (IPP5.0) (Media Cybernetics) and/or an open source software Fiji (Image J). For the measurements of vesicle turnover and protein expression in terminals at dendrites, the AOIs were chosen at the high-density regions of dendritic branches among the "islands" of cell bodies. The general criterion for choosing a "high-density dendritic area" was that most of area in the AOI was covered by neuronal branches. For the fluorescent colocalization experiments (described below), the images from the same AOI were aligned together and registered using the algorithms Rigid Body Registration and UnwarpJ to register the images and tackle the distortions in Fiji. For in vivo experiments, the Electron Microscopy (EM) images and immunofluorescent images of ultrathin brain slices were described below.

Hippocampal Neuron Cultures

High-density primary cultures of hippocampal CA3-CA1 pyramidal neurons of neonatal Sprague-Dawley rats (<24 hr) were used in the current study, as described before (Slutsky et al., Neuron. 2004; 44(5):835-49). The neurons were cultured on 1 #coverslips (8 mm×8 mm) for 14-28 days in vitro (div) before use. $[Mg^{2+}]_o$ in culture medium was adjusted to different concentrations according to experimental designs. In each experiment, sister cultures from the same batch were always used for treatment and control conditions on the same day, and the experimental results were repeated using several different batches.

Vesicle Turnover Detection

Vesicle turnover in response to bursting action potentials (see below) is a measure of the functional status of a presynaptic terminal. FM dyes were used to visualize the vesicle turnover of presynaptic terminals. In the current study, 10 μM FM1-43 or 20 μM FM4-64 (Biotium) was loaded under different patterns of field stimulations, such as 5AP bursts (5 action potentials (Aps) at 100 Hz for each burst, 6 bursts (30 APs totally) with 10 s inter burst interval were given) and "maximal stimulation" (600 APs at 10 Hz). Releasable fluorescence in the AOI (ΔF) was obtained from the difference of loading ($F_1$) and unloading ($F_2$) images, i.e. $\Delta F=F_1-F_2$ (see FIG. 1A). For FIG. 3C, the loading/unloading procedures were performed under 5AP bursts and 600AP stimulation at the same area of network successively. Subsequently, the $\Delta F_{5AP}$ and $\Delta F_{600AP}$ images were registered to colocalize the vesicle turnover for these two stimulating protocols for individual terminals.

Functional Terminal Density Measurement

The functional terminal density ($N_{5AP}$) at a dendritic branch was defined as the number of 5AP bursting stimulation induced FM(+) puncta (#$FM_{5AP}$) per unit area of dendritic branch (A), $N_{5AP}$=#$FM_{5AP}$/A. Retrograde immunofluorescence (IF) staining of MAP2 (as described below), which specifically presents in dendritic skeleton, was used to label dendritic area and A was calculated from MAP2(+) area. To limit the error of A introduced by the immunoreactivity of MAP2(+), the staining and imaging parameters were rigorously controlled in different batches of IF and the grey-scale histograms of MAP2(+) images were equalized before measuring A. Here, to ensure the equalized MAP2(+) marked area could reflect the real morphology of dendrites, the parameters of histogram equalization were set based on the comparison of MAP2(+) and DIC images. For most experiments, the average $N_{5AP}$ of an AOI was calculated from the total number of FM(+) puncta divided by total MAP2(+) area to reduce the sampling error. Then the mean $N_{5AP}$ of all AOIs (1-5 AOIs/coverslip) was used to represent the average $N_{5AP}$ in a coverslip; for each statistical data point, several coverslips were used and the mean±standard error of the mean (SEM) of all coverslips was represented (see figure legends). For FIGS. 3B and D, the FM(+) puncta density induced by 600AP stimulation was also calculated and presented in the same way as described above. Exceptionally, for FIG. 2B, each point represented the $N_{5AP}$ at a single segment of dendritic branch. In general, in an AOI (59 μm×59 μm, with varying dendritic density) 351-1598 presynaptic functional terminals could be detected by FM dyes for different experimental groups under 5AP bursting stimulation.

Immunofluorescence In Vitro

The neurons were fixed in 1×PBS (pH 7.4) containing 1% Paraformaldehyde (E.M.S.), 0.01% Glutaraldehyde (Alfa Aesar) and 4% Sucrose (Amresco) for 1 hr RT. The fixatives were gently washed several times in Tris buffer (pH 7.6), which contained (in mM): Tris Base 25, Tris-HCl 25, NaCl 150 (Amresco), and was filtered through 0.22 μm film before use. The coverslips were then permeablized and blocked in freshly prepared blocking solution (using the Tris buffer), which contained 1% (w/v) bovine serum albumin (BSA; Amresco) and 0.1% (w/v) Saponin (Sigma) for 1.5 hr RT. Primary antibodies were incubated overnight at 4° C. and probed with CF™-dye conjugated secondary antibodies (Biotium) for 1 hr RT. Z-stack images (with 0.5 μm step in z-direction) were taken immediately on FV300, and processed as described above. Specifically, images from 236 μm×236 μm regions were taken at 2048×2048 pixels for FIG. 5B.

The following primary and secondary antibodies were used (name, catalogue number, company and dilution): anti-MAP2 (188004, SYSY or NB300-213, Novus) 1:200-1:400; Synaptophysin (SYP) (MAB5258, Millipore or 101 004 SYSY) 1:400; VGLUT1 (AB5905, Millipore) 1:300; VGAT (AB5062, Millipore) 1:200; Bassoon (141 003, SYSY) 1:200; Synapsin1 (AB 1543, Millipore) 1:400; $Ca_v2.2$ (AB5154, Millipore) 1:200; $Ca_v2.1$ (152 103, SYSY) 1:200; Synaptotagmin1 (SYT1) (105 011 or 105 003, SYSY) 1:200; Rab3a (107 111 or 107 102, SYSY) 1:200; RIM1 (140 013 or 140 003, SYSY) 1:200; Munc13-1 (126 103, SYSY) 1:200; ERC1b2 (ELKS) (143 003, SYSY) 1:200; Syntaxin1 (110 011, SYSY) 1:100. CF-dye conjugated secondary antibodies: CF488A 1:400, CF555 1:100-1:200 and CF640R 1:100-1:200 (Biotium).

In Vitro Protein Immunofluorescence Quantifications

Figure 3A:
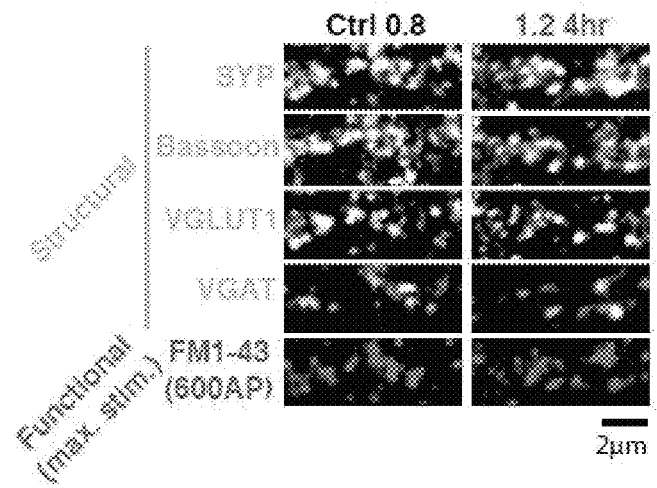
FIGS. 3A-3F are a collection of graphs and images showing the effect of presynaptic $Ca^{2+}$ sensitivity on functional terminal density in response to burst pattern of inputs, according to embodiments of the present disclosure.
Figure 3B:
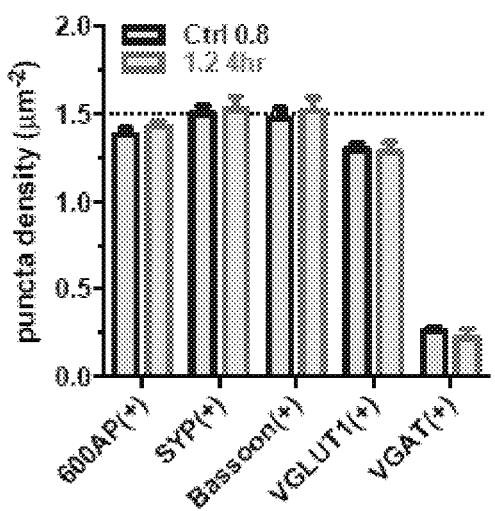

For FIG. 3B, the average density of immunoreactive puncta of a given AOI was calculated from the total puncta number divided by the total MAP2(+) area; the values from several AOIs were averaged to represent the average puncta density in a coverslip; for each data bar, the mean±SEM of these coverslips were presented. For FIG. 4D, and FIGS. 5D-5F, the total fluorescence intensity of all immunoreactive puncta in an AOI was divided by the total MAP2(+) area to get the average immunoreactivity per unit area of dendrites in the AOI; several AOIs were measured from a coverslip and the mean of these AOIs was calculated to represent the average immunoreactivity per unit area of dendrite in the coverslip; for each data point, several coverslips were used and the mean±SEM of these coverslips were presented. For FIGS. 5C and 5D, the mean fluorescence intensity per pixel in each cell body was measured (the somatic area of each cell body was measured from DIC image) and then the mean±SEM of all the cell bodies were presented. For FIGS. 7B-7E, the average protein immunoreactivity of an AOI was defined as the total fluorescence of a protein per unit area of MAP2(+) marked dendrites (as described above); 9 AOIs were selected from a low $[Mg^{2+}]_o$ (Ctrl 0.8) coverslip or a high $[Mg^{2+}]_o$ (1.2 4 hr) coverslip respectively (these two coverslips were sister cultures from the same culturing dish); for each protein, the average protein immunoreactivity values were normalized to the mean of the 9 AOIs of Ctrl 0.8 group. The normalized immunoreactivity per unit area of dendrites was defined as Q index, then $\Sigma Q_{proteins} = Q_{SYT1} + Q_{Rab3a} + Q_{RIM1} + Q_{Munc13} + Q_{ELKS} + Q_{Syntaxin1}$.

Intracellular $Mg^{2+}$ Measurement

The mature cultures were incubated in Tyrode's solution with 2 μM Magnesium Green™-AM (MgGrn, an intracellular $Mg^{2+}$ indicator, Invitrogen) for 30 min and washed out for 20 min; both at 37° C. Fluorescent images of several AOIs in each coverslip were taken on FV300 at RT. In the current study, the MgGrn fluorescence at basal condition (without eliciting any AP stimulus) (FIG. 1A) was measured to eliminate any effects caused by AP-induced intracellular $Ca^{2+}$ fluctuations. Since the intracellular $Ca^{2+}$ concentration ($[Ca^{2+}]_i$) at basal condition was usually <100 nM, the contribution of $Ca^{2+}$ to MgGrn fluorescence was very small. Thus, the fluorescent intensity of MgGrn could be considered proportional to $[Mg^{2+}]_i$. Since the measured MgGrn fluorescence was also dependent on the local volume of branches in network, a physical model was built to describe this phenomenon and the calculating formula that corrected the effect of varying local volumes was derived.

Figure 10A:
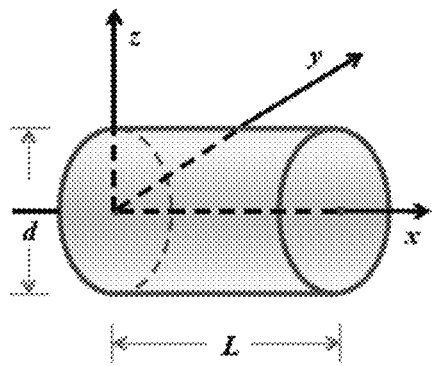
FIGS. 10A-10F are a collection of schematic diagrams and graphs modeling the measurement of intracellular $Mg^{2+}$ concentration in a segment of dendrite branch by magnesium green (MgGrn) fluorescence, according to embodiments of the present disclosure.

At basal condition, the total fluorescence in a branch was positively proportional to the total amount of free $Mg^{2+}$ ions in cytoplasm. A cylindrical shape of each neuronal branch was assumed (FIG. 10A); thus the following relationship was deduced:

$$fluo_{total} = \iiint_{V'} F(x, y, z)dv = \iiint_{V'} F(x, y, z)dxdydz$$

Where $fluo_{total}$ was the total fluorescence, $F(x, y, z)$ was the spatial distribution function of fluorescence, dv was the differential volume at the point (x, y, z), V' represented the volume of fluorescence detectable space.

Then the relationship as follows was derived based on the assumption that $[Mg^{2+}]_i$ was proportional to integral fluorescence per unit volume of a neuronal branch:

$$[Mg^{2+}]_i \propto \frac{\int\int\int_{V'} F(x, y, z)\, dx\, dy\, dz}{V}$$

Where V was the volume of the branch.
From FIGS. 10A and 10B:

$$[Mg^{2+}]_i \propto \frac{\int_{-h}^{h} dz \int_{d} dy \int_{L} F(x, y, z)dx}{\frac{1}{4}\pi d^2 L}$$

Where [−h, h] was the range in z-direction, where fluorescence was detectable, L, d were the length (in x-direction) and width (in y-direction) of the maximal projection of fluorescence on xy-plane (FIG. 10B), which were roughly equal to the length and diameter of the branch when the threshold of fluorescence during segmentation was set properly. Thus the branch volume V was approximately equal to $\pi d^2 L/4$.

θ (μm/pixel) was set as the resolution in x- and y-direction, which was 0.05754 μm/pixel in the experiments, and set ρ as the resolution in z-direction, which was equal to the scanning step of z-stack, i.e. ρ=1 μm. Thus L=lθ, d=mθ, 2h=nρ, where l, m were the pixels of the branch in x, y directions, n was the number of images in the stack:

$$[Mg^{2+}]_i \propto \frac{4}{\pi \theta^2 d} \cdot \frac{\int_{-h}^{h} dz \int_{d} dy \int_{L} F(x, y, z)dx}{ml}$$

Figure 10B:
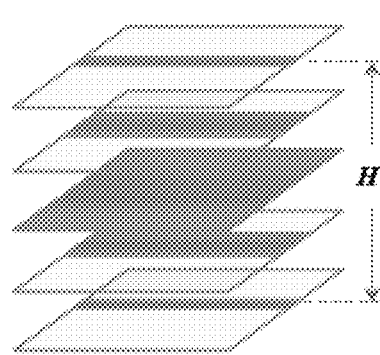

By approximate numerical integration:

$$[Mg^{2+}]_i \propto \frac{4}{\pi \theta^2 d} \cdot \frac{\sum_{z=-\frac{1}{2}n\rho}^{\frac{1}{2}n\rho} \sum_{y=0}^{m\theta} \sum_{x=0}^{l\theta} F(x, y, z)}{ml} = \frac{4}{\pi \theta^2 d} \cdot \sum_{z=-\frac{1}{2}n\rho}^{\frac{1}{2}n\rho} \overline{F(z)}$$

Where $\overline{F(z)}$ was the mean fluorescence per pixel in the region of the branch in the image (whose coordinate was z) in z-stack (FIG. 10B).

Figure 10C:
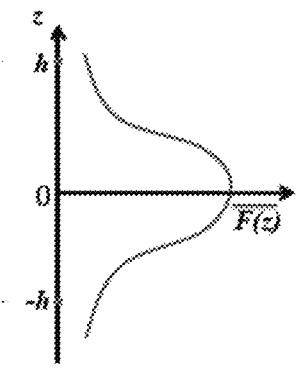

Since $\overline{F(z)}$ exhibited Gaussian distribution well in the range of [−nρ/2, nρ/2] (FIG. 10C), and the normalized distribution curve was the same among different branches (FIG. 10C), then $\Sigma \overline{F(z)}$ was linearly proportional to $\overline{F(z)}_{max}$ according to the properties of Gaussian curve, thus:

$$[Mg^{2+}]_i \propto \frac{4}{\pi \theta^2 d} \cdot \overline{F(z)}_{max}$$

And this formula could further be simplified as follows:

$$[Mg^{2+}]_i \propto \frac{\overline{F(z)_{max}}}{d}$$

Where $\overline{F(z)}_{max}$ was the mean intensity per pixel in the area of a branch in the compressed image of the stack (the compressed image was achieve by maximal z-projection of the stack, as described above).

Figure 10D:
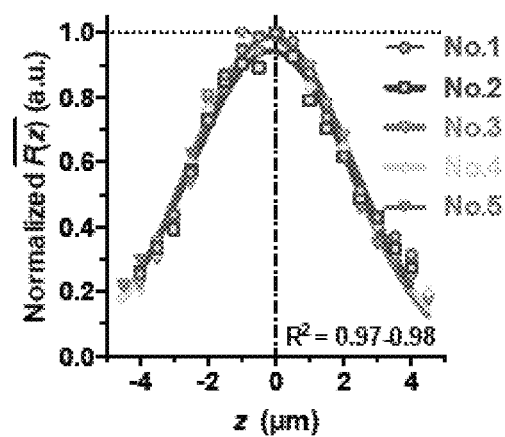
Figure 10E:
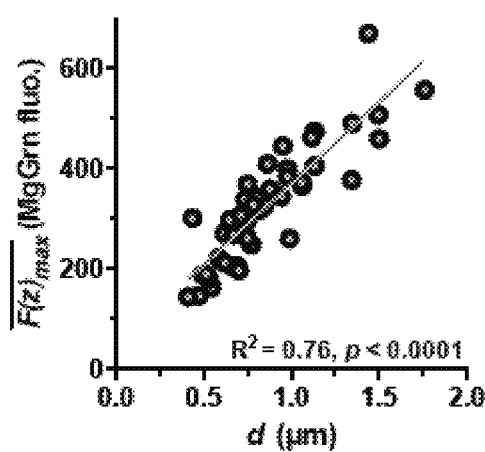
Figure 10F:
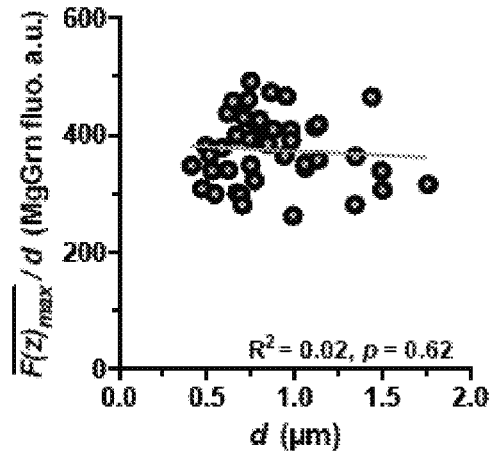

From the formula, $[Mg^{2+}]_i$ was approximately positively proportional to $\overline{F(z)}_{max}$ but negatively proportional to the diameter of branch, consistent with the experimental observations (FIGS. 10D and 10E).

FIGS. 10A-10E. Modeling the measurement of $[Mg^{2+}]_i$ in a segment of branch by MgGrn fluorescence. (FIG. 10A) A segment of branch was modeled as a cylinder characterized by diameter (d) and length (L). (FIG. 10B) Z-stack of MgGrn fluorescent images was taken in the range of −h to h at z-axis. $\overline{F(z)}$ represented the mean fluorescent intensity per pixel within a branch area from each layer in the z-stack (left). Theoretically, $\overline{F(z)}$ should exhibited a Gaussian distribution along z-axis (right). (FIG. 10C) Normalized $\overline{F(z)}$ values (normalized to maximum) from z-stacks of 5 representative branches (No. 1-5) exhibited well Gaussian distributions with almost the same shape in parallel experiments (Gaussian curve fitting). (FIG. 10D) In the maximal z-projection of the stack, the mean intensity of individual branches ($\overline{F(z)}_{max}$) showed a linear correlation with diameter (d). (FIG. 10E) After correction, the value $\overline{F(z)}_{max}/d$ was not correlated with diameter in different branches.

In the experiments, given a randomly selected AOI of dendritic area (the image was obtained as described above), 50-100 branches were randomly selected from each AOI and the mean intensity of fluorescence (i.e. $\overline{F(z)}_{max}$) of each branch was measured. Meanwhile, the diameter of each branch (d) was measured from the DIC image, then the $\overline{F(z)}_{max}/d$ was calculated to represent the $[Mg^{2+}]_i$ in the branch. The mean value of these 50-100 branches was calculated to represent the level of $[Mg^{2+}]_i$ in the AOI. For each coverslip, several AOIs were measured and the mean value of these AOIs was calculated to represent the average level of $[Mg^{2+}]_i$ in the coverslip. For each data point, several coverslips were used. For each statistical data point, the mean±SEM of all coverslips was presented. Specifically for FIG. 2B, each data point represented the $[Mg^{2+}]_i$ (MgGrn fluorescence arbitrary units (a.u.)) value in an individual branch.

Mitochondrial Status Assessment

Figure 6A:
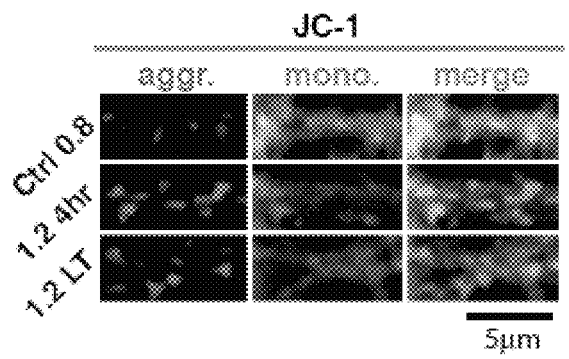
FIGS. 6A-6D are a collection of images and graphs showing increase of general mitochondrial function and intracellular adenosine triphosphate (ATP) by elevating intracellular $Mg^{2+}$ levels, according to embodiments of the present disclosure.
Figure 6B:
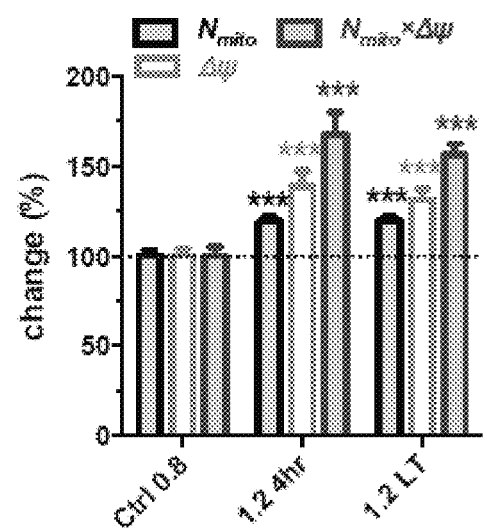
Figure 6C:
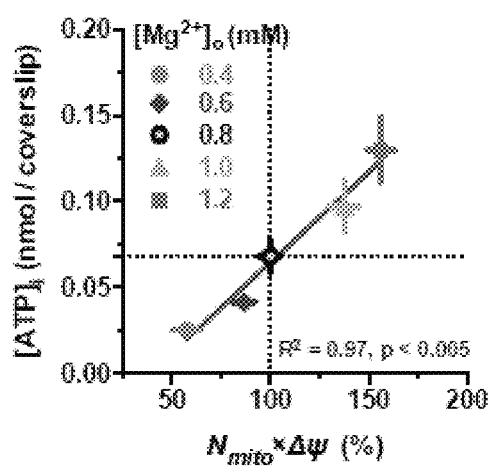
Figure 6D:
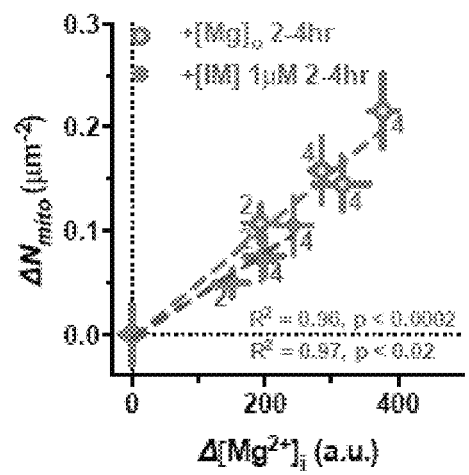
Figure 7A:
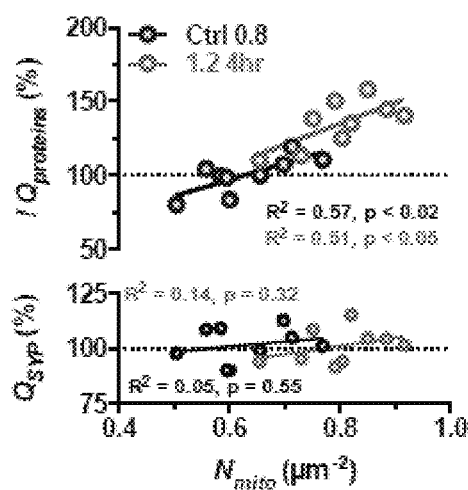

For FIG. 7A, mitochondria were marked with 40 nM Mitoview633 (Biotium) for 15 min and then washed out in blank medium for 15 min, both at 37° C. For FIG. 6A, the membrane potential-sensitive fluorescent dye JC-1 (1 μM) (Invitrogen) was used. JC-1 was incubated for 15 min followed by a 15 min washout at 37° C. Fluorescent images were taken on FV300 confocal. Mitochondrial membrane potential (ΔΨ) of each mitochondrion was estimated by the ratio of fluorescence of aggregate versus monomer form of JC-1, i.e. $F_{aggr}/F_{mono}$. JC-1 was excited by 488 nm laser and the emission spectra were collected at 510-575 nm and >575 nm at the same time separately. Then the ratio of fluorescence at >575 nm versus at 510-575 nm ($F_{aggr}/F_{mono}$) was calculated for each individual mitochondrial punctum to represent the ΔΨ of that mitochondrion. To estimate the valid range of $F_{aggr}/F_{mono}$, $F_{aggr}/F_{mono}$ of individual mitochondria was measured before and after administering 5 μM Carbonyl cyanide 4-(trifluoromethoxy)phenylhydrazone (FCCP) 5 min at the same AOI. The mean $F_{aggr}/F_{mono}$ of all the mitochondria (1.21±0.02, n=942 mitochondria) was lowered to 0.26±0.002 (the minimal value of $F_{aggr}/F_{mono}$). Thus, the $F_{aggr}/F_{mono}$ value of a mitochondrion was considered to be meaningful only if it was >0.26 in the experiments, and the puncta with $F_{aggr}/F_{mono}$<0.26 (17/942 mitochondria in this experiment, i.e. ~2%) were excluded in statistics. $F_{aggr}/F_{mono}$ was calculated for each individual meaningful punctum and the mean value of population was calculated from all the puncta to represent the general $\Delta\Psi$ in this AOI. 3-5 AOIs were measured for each coverslip and the mean of the AOIs were calculated to represent the average $\Delta\Psi$ of the coverslip. For each bar or point in FIG. 6, several coverslips were used (described in legends). The density of mitochondria ($N_{mito}$) was also quantified by counting the number of JC-1-aggregate(+) fluorescent puncta (FIG. 6) or MitoView633(+) puncta (FIG. 7) per area of branches. No difference in $N_{mito}$ measurement between the two markers was observed.

Co-Staining of Multiple Fluorescent Markers

For FIG. 3A, FM1-43 staining was performed and images were taken on confocal. Then retrograde IF was performed at the same AOI. For FIG. 7A, MitoView633 was used to mark mitochondria, images were taken, and then FM1-43 staining was performed and images were taken. For the combination of FM and IF imaging, a new strategy of retrograde IF was performed for several rounds to label multiple presynaptic proteins at a given AOI (HZ and GL unpublished method: Single Synapse Analysis by FM1-43 and Immunofluorescence Imaging Array, which was named "SAFIA"). For each round, 2-3 antibodies were stained and probed by fluorophore-conjugated secondary antibodies (as described above), and then both the DIC and the fluorescent images were taken immediately. After taking all images, primary and secondary antibodies were completely eluted (data not shown) by a stripping buffer containing 0.2 M NaOH and 0.015% (w/v) SDS (Amresco) in deionized water for 20 min RT, twice, and then washed out gently and thoroughly in Tris buffer (described above) for more than 1 hr at room temperature (RT) (to make sure no residual SDS was left). Then the IF of other 2-3 primary antibodies at the same AOI was performed as described above and images of these AOIs were taken. DIC image was used as landmark of each AOI. All the fluorescent images were aligned and registered in Fiji and analyzed as described above. In the first round of IF in the SAFIA experiments, 300 μM ADVASEP-7 (sulfonated β-cyclodextrin; Biotium) was added into the blocking solution during the permeablization procedure to quench the residual FM-dye in the membrane and to ensure that the background introduced by FM-dye was as low as possible in the following IF experiments (data not shown). For FIGS. 1B and 2A, $[Mg^{2+}]_i$ was stained with MgGrn, images were taken at basal condition, and then the FM4-64 staining was performed. All the procedures were described separately as aforementioned.

Figure 5A:
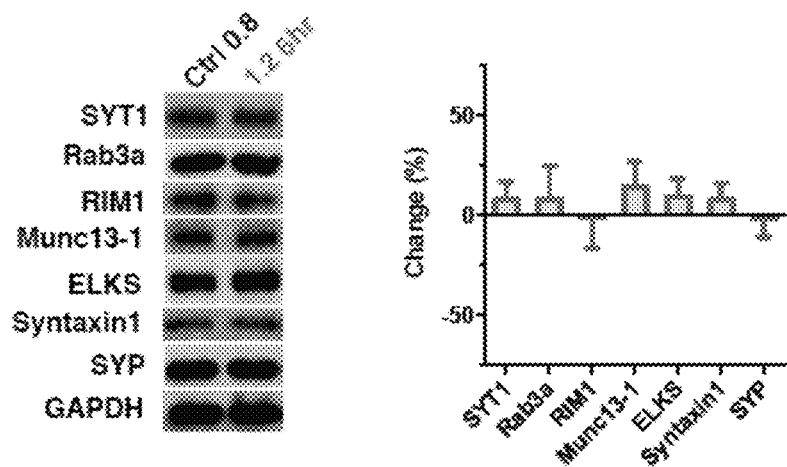
FIGS. 5A-5I are a collection of images and graphs showing increase in the efficiency of axonal transport of $Ca^{2+}$-sensitivity-related proteins in response to elevated intracellular $Mg^{2+}$ levels, according to embodiments of the present disclosure.

Western Blot $[Mg^{2+}]_o$ was elevated from 0.8 to 1.2 mM in mature sister cultures (14-28 div) for 6 hr. Proteins were extracted from the cultures and then resolved on Polyacrylamide gels. Proteins were transferred from gels to polyvinylidene fluoride (PVDF) membrane and probed with the following antibodies: anti-SYP (Millipore) 1:50,000, SYT1 1:5,000, Rab3a 1:500-1,000, RIM1 1:800, Munc13-1 1:400, ERC1b2 (ELKS) 1:1,000, Syntaxin1 1:500-1,000 (SYSY), GAPDH 1:1,000 (CST). The other procedures were the same as previously described. For the analysis, digital images were quantified using IPP5.0, and the level of each protein was normalized by the level of GAPDH in the same lane. The sample from each coverslip was resolved individually and repeated for 3 times, and then the average value of the 3 times was calculated to represent the protein level in the coverslip. For each bar in FIG. 5A, the mean±SEM of coverslips was presented.

ATP Measurement

Cultured neurons were quickly detached from a coverslip with 500 μL boiling extraction solution containing 40 mM HEPES (pH 7.8) and 4 mM $MgSO_4$. The solution was repeatedly pipetted to ensure complete lysis. The lysed neurons were immediately transferred into a centrifugal tube and centrifuged at 12000 rpm at 4° C. for 5 min. For each coverslip, total ATP content of supernatant was immediately determined using a Luciferin-luciferase ATP Assay Kit (Invitrogen). For each data point in FIGS. 6C, 7E and 7F, the mean±SEM of coverslips was presented.

Electron Microscopy and Immunofluorescence In Vivo

Mature Sprague-Dawley rats (male, 16 months old) were fed Magnesium L-Threonate (MgT; dosage as previously described) (Magceutics Inc.) in their water for 8 months. Control (n=10) and MgT-supplemented (n=11) rats (24 months old) were anesthetized with 4% Benbarbitol (0.2 mL/100 g body weight), and sacrificed by transcardioperfusion of 1% Paraformaldehyde (E.M.S. or Ted Pella), 0.01% Glutaraldehyde (Alfa Aesar) and 0.05% Picric Acid (Sigma) in 1× phosphate buffer saline (PBS; Gibco) (pH 7.4, pre-cooled at 4° C.). Each brain was dissected, the hippocampus was coronally sliced on a vibratome (VT1000S Vibratome, Leica) into 50 μm sequential sections, and slices were stored in fixative solution at 4° C. for 24 hr. The Hippocampus CA1 Stratum Radiatum region from the neighbor sections was cut off and dissected into <1 $mm^2$ square blocks which were then used for electron microscopy (EM) and IF separately. The blocks were rinsed in 1×PBS (pH 7.4) for 1 hr and 1× Maleate Acid (Sigma) buffer (pH 6.0) for 1 hr to wash out the fixatives.

For the blocks prepared for EM, they were post-fixed in 1% Osmium Tetraoxide (Ted Pella) and 1.5% Potassium Ferricyanide (Sigma) in MB (pH 6.0) for 1 hr, and stained with 3% Uranyl Acetate (Ted Pella) for 1 hr. Then the blocks were dehydrated with 50, 70, 80, 95%, 100%, and 100% Ethanol sequentially, for 15 min each. Following dehydration, blocks were placed in 100% Propyleneoxide (Sigma) for 10 min twice. All the procedures above were performed on ice. Then blocks were infiltrated with 50% Propyleneoxide+50% SPI-PON 812 resin (SPI-CHEM) for 60 min RT, 100% resin for 24 hr at 4° C., and subsequently transferred into embedment molds fulfilled with pure resin and placed in 60° C. oven for polymerization for 24 hr. 70 nm ultrathin slices were cut and then stained with 3% Uranyl Acetate and 0.4% (w/v) Lead Citrate, sequentially. Images were taken on Transmission (Hitachi H-7650) (80 kV, 1 k×1 k pixels, 25 kX, 2 nm/pixel) or Scanning EM (Supra55, Zeiss) (10 kV, 8 k×8 k pixels, 2 nm/pixel, 15 μs/pixel). For the SEM, ultrathin slices were mounted on silicon chips, which can enhance the electro-conductivity dramatically (even without carbon coating). The density of mitochondria in an EM image was defined as #mitochondria/area. For each rat, the density of mitochondria was calculated from the mean density of 67-96 TEM images and 5 SEM images (the density measured in TEM images was the same as that measured in SEM images).

Blocks prepared for IF were treated with 1% Tannic Acid (Sigma) for 1 hr, 1% Uranyl Acetate in Maleate Acid buffer (pH 6.0) for 1 hr, and then dehydrated with 50, 70, 80, 95, 100%, and 100% Ethanol containing 1% PPD (Sigma) sequentially, for 15 min each. Mixture of Ethanol and LR White resin (E.M.S.) with the ratios 2:1, 1:1, 2:1 and pure resin were used to infiltrate the tissue blocks, each for 1 hr, then replaced by 100% LR White for 24 hr. All the above procedures were performed on ice. The blocks were placed in capsules filled with LR White resin and put in 55° C. oven for polymerization for 48 hr. 70 nm ultrathin slices were cut and mounted on coverslips. The IF was performed according to Array Tomography technique. SYP, VGLUT1, SYT1, Rab3a, RIM1, Munc13-1, ELKS and Syntaxin1 were stained in the ultrathin slices and fluorescent images of each protein were taken at 1024×1024 resolution with 0.03836 μm/pixel resolution using a 60× objective (UPlanSApo 60XW N.A. 1.20) on FV300. For each protein, the total fluorescence (F) of all the puncta per area of image was measured to represent the quantity of that protein. For each rat, F values from 5-7 tissue blocks were averaged to represent the protein quantity in that rat ($F_{rat}$). $F_{rat}$ of each protein was normalized by the mean value of all rats in control group to get the normalized quantity Q. To estimate the total quantity of the $Ca^{2+}$-sensitivity-related proteins, the Q of the 6 proteins in the same rat was summed together to represent the total quantity in that rat ($\Sigma Q_{proteins}$), $\Sigma Q_{proteins}=Q_{SYT1}+Q_{Rab3a}+Q_{RIM1}+Q_{Munc13}+Q_{ELKS}+Q_{Syntaxin1}$.

Experimental Animals

All the rats involved in this paper were purchased from Vital River Laboratory (Beijing). All the animal experiments were approved by Tsinghua University Committees on Animal Care.

Statistics Analysis

Data are shown as mean±SEM. Statistical significance is considered as p<0.05. Two-tailed Student-t or Kolmogorov-Smirnov test was used, unless otherwise noted.

Results

Functional Terminal Density is Determined by Intracellular $Mg^{2+}$

Bursting action potentials (APs) (correlated activity) were used as input to quantify the functional synapse density. The stimuli sequence contained 6 groups of 5AP bursts with an inter-burst-interval of 10 s (30 APs total) (FIG. 1A). FM1-43 or FM4-64 was used to detect vesicle turnover of functional terminals (FIG. 1A). Here, a terminal was defined as functional if releasable FM dye was detectable following bursting input stimulation. A terminal was considered to be nonfunctional if it failed to release even one vesicle after 30 AP bursting input (i.e. no detectable FM dye; Pr<0.04).

FIGS. 1A-1D. Functional terminal density in response to 5AP bursts is nonlinearly associated with extracellular $Mg^{2+}$ concentration. (FIG. 1A) The schematic experimental procedures. Magnesium Green-AM ester (MgGrn) staining and imaging were performed at basal condition (close to natural culturing state, without eliciting any stimulus). After MgGrn imaging, vesicle turnover was detected by FM dye under field stimulations, such as bursting stimulations (e.g. 5AP bursts). For the bursting stimulation, 30 action potentials (APs) were divided into 6 bursts (inter-burst-interval was 10 s), each of which contained 5 APs at 100 Hz. The MgGrn and FM dye imaging procedures were combined (e.g. for the experiment in B) or conducted separately based on different experimental designs. (FIG. 1B) Neuron cultures with $[Mg^{2+}]_o$ of 0.8, 1.2 or 2.0 mM in culture medium (for 48 hr to 2 weeks) were marked by MgGrn to reveal their $[Mg^{2+}]_i$ level, and then functional terminals were detected by FM4-64 under 5AP bursts (as described in A) at the same area of interests (AOIs). Pseudo-color scale: fluorescent intensity. (FIG. 1C) Bell-shape association between functional terminal density in response to 5AP bursts ($N_{5AP}$) and $[Mg^{2+}]_o$ (n=3-5 coverslips, Gaussian curve fitting, $R^2$=0.84). (FIG. 1D) Bell-shape association between $[Mg^{2+}]_i$ (MgGrn fluorescence) and $[Mg^{2+}]_o$ (n=3-5 coverslips, Gaussian curve fitting, $R^2$=0.86). The mean±SEM of coverslips was presented. For the measurement of $N_{5AP}$ and $[Mg^{2+}]_i$ see "Materials and Methods", above.

Figure 1B:
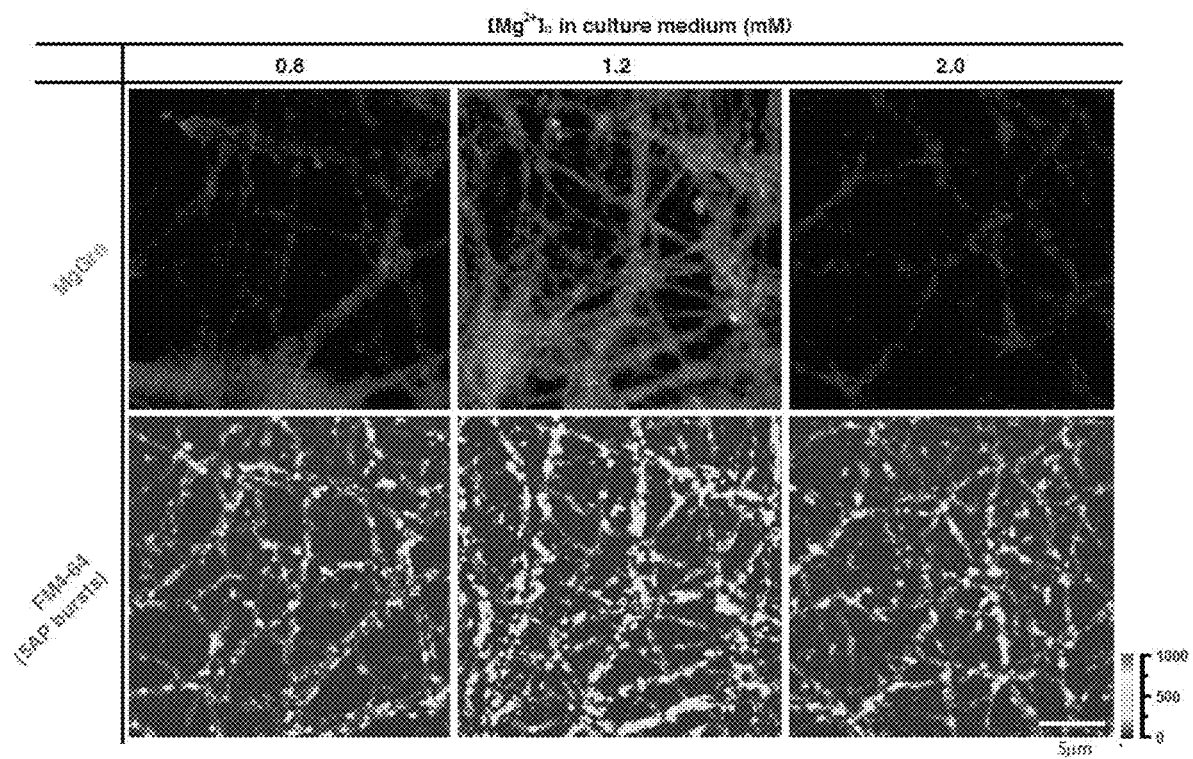
Figure 1C:
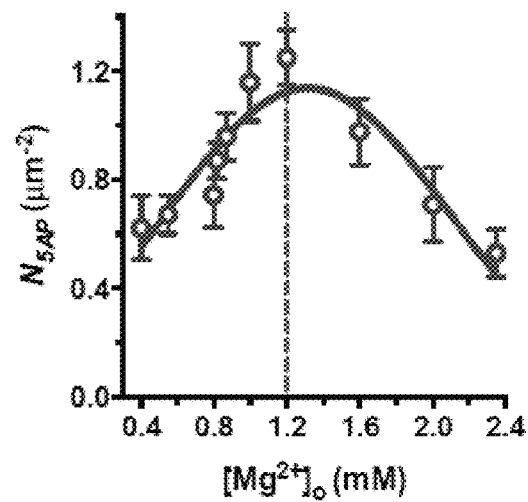
Figure 1D:
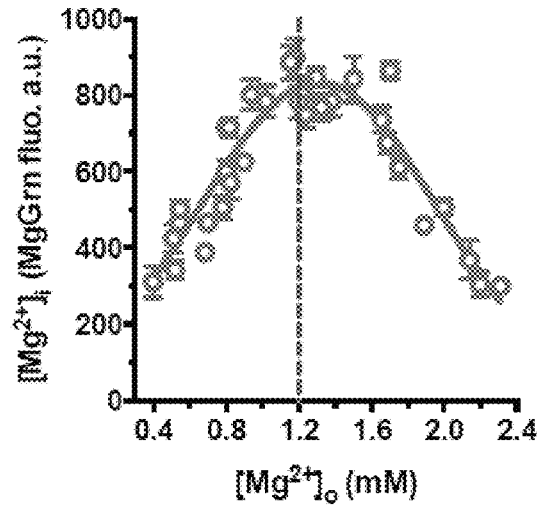
Figure 2A:
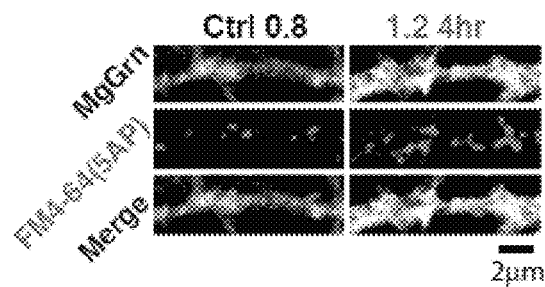
FIGS. 2A-2F are a collection of images and graphs showing regulation of functional terminal density in response to burst pattern of inputs at individual branches by intracellular $Mg^{2+}$ level, according to embodiments of the present disclosure.

Here, it was determined whether the change of $[Mg^{2+}]_o$ could influence functional terminal density. After a long term (48 hr to 2 weeks) increase of $[Mg^{2+}]_o$ in culture medium, functional terminal density ($N_{5AP}$) was positively proportional to $[Mg^{2+}]_o$ as $[Mg^{2+}]_o$ increased from 0.4 to 1.2 mM. However, $N_{5AP}$ decreased as $[Mg^{2+}]_o$ further increased from 1.2 to 2.4 mM (FIG. 1B lower and C). To understand why $N_{5AP}$ and $[Mg^{2+}]_o$ exhibited such a bell-shape relationship, the relationship between $[Mg^{2+}]_o$ and intracellular $Mg^{2+}$ concentration ($[Mg^{2+}]_i$) was investigated. An intracellular $Mg^{2+}$ indicator, Magnesium Green-AM ester (MgGrn), was used to label intracellular $Mg^{2+}$ at basal condition (without eliciting any AP stimulus), the fluorescent intensity of MgGrn could be considered proportional to $[Mg^{2+}]_i$ (see Methods). Thus MgGrn fluorescence was used to determine the relative quantity of $[Mg^{2+}]_i$ in each branch and to estimate the average $[Mg^{2+}]_i$ at a local area of the network (see Methods). By measuring MgGrn fluorescence in the neurons cultured in different $[Mg^{2+}]_o$ culture media (for 48 hr to 2 weeks), it was found that altering $[Mg^{2+}]_o$ led to a dramatic change in MgGrn fluorescence at basal condition (FIG. 1B upper; the MgGrn images were taken before FM staining at the same area of the network, for procedures see FIG. 1A). Interestingly, $[Mg^{2+}]_i$ (represented by the corrected MgGrn fluorescence, see "Materials and Methods" above) versus $[Mg^{2+}]_o$ exhibited a bell-shape relationship (FIG. 1D) similar to that of $N_{5AP}$ versus $[Mg^{2+}]_o$ (FIG. 1C). These data implied the possibility that $N_{5AP}$ was closely correlated with $[Mg^{2+}]_i$ but not $[Mg^{2+}]_o$.

Figure 2B:
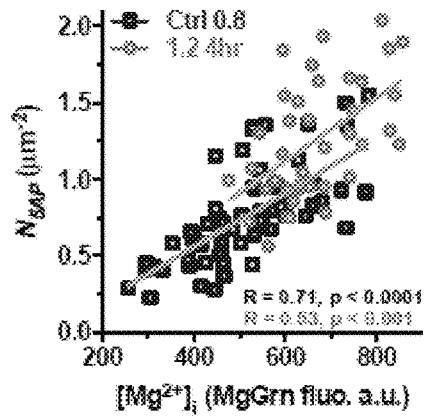

To check this hypothesis, $[Mg^{2+}]_o$ of 0.8 mM was chosen as the baseline concentration (Ctrl 0.8) and $[Mg^{2+}]_o$ was elevated from 0.8 to 1.2 mM for 4 hr (1.2 4 hr). Intracellular $Mg^{2+}$ was then monitored with MgGrn and functional terminals (responding to 5AP bursts) was observed with FM4-64; and the colocalization of FM4-64(+) puncta and MgGrn(+) fluorescence at each branch was measured (FIG. 2A, left panel). Quantitative analysis revealed that $N_{5AP}$ was linearly correlated with $[Mg^{2+}]_i$ at individual branches (FIG. 2B, squares, linear regression) at control conditions. After elevating $[Mg^{2+}]_o$ for 4 hr, both the density of FM4-64(+) puncta and MgGrn(+) fluorescence increased (FIG. 2A, right panel), and remained linearly correlated (FIG. 2B, circles, linear regression). This result demonstrated that the functional terminal density is closely matched with $[Mg^{2+}]_i$ at different branches in the same network. Because of this positive correlation, it was hypothesized that $[Mg^{2+}]_i$ might play a pivotal role in the regulation of $N_{5AP}$.

FIGS. 2A-2F. Functional terminal density to bursts is regulated by intracellular $Mg^{2+}$ level at individual branches. (FIG. 2A) Colocalization of MgGrn-marked $[Mg^{2+}]_i$ and FM4-64-marked functional terminals responding to 5AP bursts input at single branches before (Ctrl 0.8) and after elevating $[Mg^{2+}]_o$ for 4 hr (1.2 4 hr). (FIG. 2B) $N_{5AP}$ was linearly correlated with $[Mg^{2+}]_i$ (normalized fluorescence intensity of MgGrn) at individual branches before and after elevating $[Mg^{2+}]_o$ for 4 hr. Each point represents the data from a branch. (FIG. 2C) $[Mg^{2+}]$'ON' and 'OFF' experiment. MgGrn marked $[Mg^{2+}]_i$ and FM1-43 marked functional terminals responding to 5AP input. "1.2 LT": elevating $[Mg^{2+}]_o$ from 0.8 to 1.2 mM for >48 hr; "1.2 LT to 0.8 6 hr": decreasing $[Mg^{2+}]$ from 1.2 to 0.8 mM for 6 hr;

"Ctrl+IM 4 hr": adding 1 μM Imipramine (IM) into Ctrl ($[Mg^{2+}]_o$ 0.8 mM) for 4 hr. Pseudo-color scale: fluorescent intensity. (FIGS. 2D-2F) The time-course curves of $[Mg^{2+}]_i$ and $N_{5AP}$ by different treatments shown (FIG. 2C) (n=5 coverslips for each point). For (FIGS. 2C-2F), data from sister cultures of the same batch. For (FIGS. 2D-2F), the mean±SEM of coverslips was presented. Two-tailed Student's t-test comparing each time point after $[Mg^{2+}]_o$ change to initial $[Mg^{2+}]_o$, ***p<0.001.

Figure 2C:
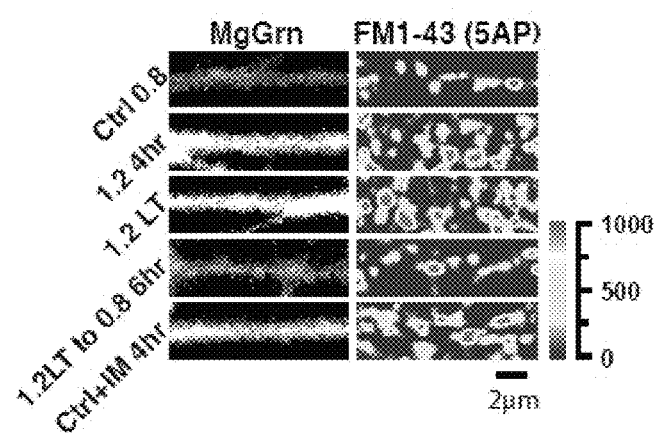
Figure 2D:
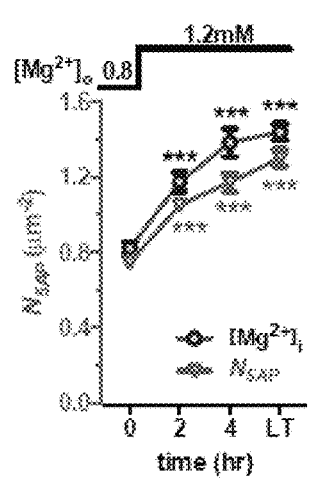
Figure 2E:
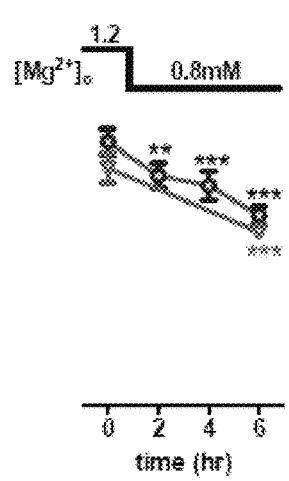
Figure 2F:
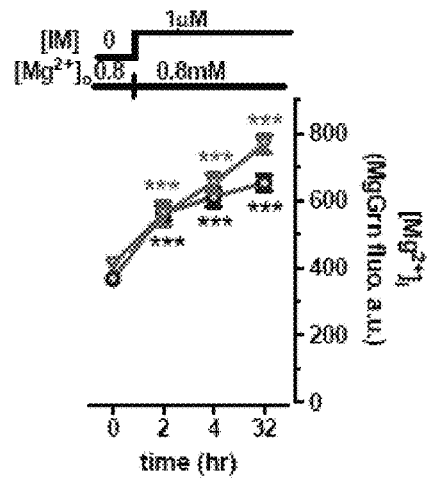

To verify the hypothesis, two types of experiments were performed using sister cultures from the same experimental batch of cultured neurons. First, the temporal correlation of $[Mg^{2+}]_i$ and $N_{5AP}$ was examined by performing a $[Mg^{2+}]_o$ 'ON' and 'OFF' experiment and comparing the time-course curves of $[Mg^{2+}]_i$ and $N_{5AP}$. The increase in $N_{5AP}$ matched temporally with the increase in $[Mg^{2+}]_i$ after elevating $[Mg^{2+}]_o$ from 0.8 to 1.2 mM. Maximum $N_{5AP}$ was reached after 4 hr as the number of $N_{5AP}$ at 4 hr persisted permanently (48 hr to 2 weeks) (FIGS. 2C and D). In contrast, $N_{5AP}$ decreased following the reduction of $[Mg^{2+}]_o$ from 1.2 to 0.8 mM for 6 hr (FIGS. 2C and E). Second, the effects of $[Mg^{2+}]_i$ elevation was examined via a chemical agent—Imipramine (IM), to rule out the possibility that increasing $[Mg^{2+}]_o$ could increase $Ca^{2+}$ channel blockage, thereby contributing to the increase in functional terminal density. IM, which can increase $[Mg^{2+}]_i$ by blocking efflux of $Mg^{2+}$ through $Mg^{2+}$ channels, was administered at 1 μM for 4 hr. Following 4 hr IM administration, $N_{5AP}$ was increased in concert with the elevation of $[Mg^{2+}]_i$, and the enhancement persisted for ~32 hr (FIGS. 2C and F). Based on these data, it was concluded that $[Mg^{2+}]_i$ might be an important factor in the regulation of functional terminal density.

Low Presynaptic $Ca^{2+}$ Sensitivity can Account for the Nonfunctional Terminals By means of manipulation of $[Mg^{2+}]_i$ by $[Mg^{2+}]_o$, $N_{5AP}$ could be conveniently and reversibly altered under physiological conditions. Since 4 hr $[Mg^{2+}]_o$ elevation was effective at increasing $N_{5AP}$ (FIG. 2D), $[Mg^{2+}]_o$ elevation in neuronal cultures was used as a tool to determine the molecular substrates involved in $N_{5AP}$ regulation.

To start, it was examined whether the increase in $N_{5AP}$ was caused by synaptogenesis. Structural terminals were labeled with antibodies against several presynaptic proteins, including synaptophysin (SYP, vesicle protein), VGLUT1 (excitatory vesicle protein), VGAT (inhibitory vesicle protein) and Bassoon (active zone protein), and their localization was monitored by immunofluorescence (IF) (FIG. 3A). There were no significant changes in the density of presynaptic protein puncta after elevating $[Mg^{2+}]_o$ for 4 hr (FIG. 3B), suggesting that elevation of $[Mg^{2+}]_i$ might not, at least within 4 hr, induce synaptogenesis.

Figure 3C:
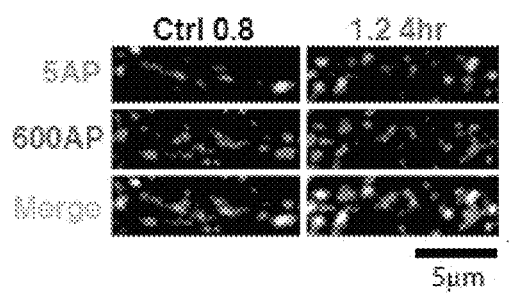
Figure 3D:
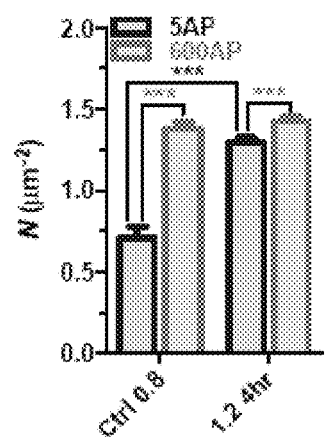
Figure 3E:
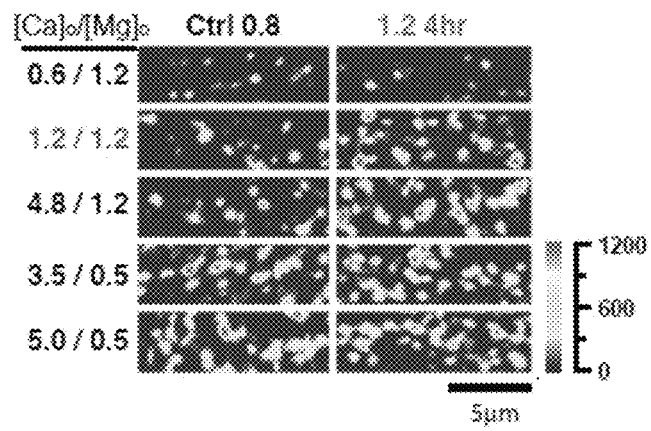

FIGS. 3A-3F. Presynaptic $Ca^{2+}$ sensitivity determines functional terminal density to bursts. (FIGS. 3A and 3B) At low (Ctrl 0.8) and high $[Mg^{2+}]_o$ (1.2 4 hr) conditions, colocalization of SYP, VGLUT1, VGAT and Bassoon positive fluorescent puncta with FM1-43 labeled releasable terminals to "maximal stimulation" (600 APs at 10 Hz) at the same dendrite (FIG. 3A). No significant changes were observed (n=6 coverslips for each bar, p=0.38-0.84) (FIG. 3B). Dotted line represents the total number of SYP(+) puncta of Ctrl 0.8. (FIGS. 3C and 3D) Colocalization of FM(+) terminals following 5AP- and 600AP-stimulation at the same branches (FIG. 3C). 51.3±9.8% (n=12 coverslips, totally 7542 5AP-induced puncta and 14701 600AP-induced puncta were analyzed) and 90.6±2.9% (n=16 coverslips, totally 16926 5AP-induced puncta and 18601 600AP-induced puncta were analyzed) terminals were functional in response to 5AP bursts (FIG. 3D) at low and high $[Mg^{2+}]_o$ conditions. (FIGS. 3E and 3F) Acute change of $[Ca^{2+}]_o/[Mg^{2+}]_o$ ratio led to the change of detectable functional terminals (FIG. 3E). Statistics of $N_{5AP}$ at different $[Ca^{2+}]_o/[Mg^{2+}]_o$ ratio (FIG. 3F) (n=5-11 coverslips). Pseudo-color scale: fluorescent intensity. Two-tailed Student's t-test comparing 5AP to 600AP as indicated (FIG. 3D), or comparing 1.2 4 hr to Ctrl 0.8 at each $[Ca^{2+}]_o/[Mg^{2+}]_o$ (FIG. 3F), p<0.01, *p<0.001. For each bar or point in (FIGS. 3B, 3D and 3F), the mean±SEM of coverslips was presented.

Next, the functionality of these terminals was evaluated. A "maximal stimulation", 600 APs at 10 Hz (600AP) was applied, to determine the vesicle turnover ability of terminals. At the low $[Mg^{2+}]_o$ condition, almost all available structural terminals had the ability to release vesicles under maximal stimulation (FIG. 3A). The density of FM(+) puncta (1.38 μm$^{-2}$) was close to that of structure-protein positive puncta (SYP(+) 1.50 and Bassoon(+) 1.47 μm$^{-2}$), indicating almost all terminals are functional under maximal stimulation (FIG. 3B).

Notably, at the low $[Mg^{2+}]_i$ condition, the 5AP bursting input-induced FM(+) puncta density was remarkably lower (0.73 μm$^{-2}$, FIG. 2D control) than the 600AP-induced FM(+) puncta density (1.38 μm$^{-2}$). It is possible that this difference was due to the ability of terminals to release vesicles under maximal stimulation but not under 5AP bursting input. To test this possibility, the vesicle release of terminals under 5AP and 600AP stimulations at the same dendrite was compared (FIG. 3C). Indeed, only ~50% of terminals were activated under 5AP stimulation at the low $[Mg^{2+}]_o$ condition (FIGS. 3C and D, Ctrl 0.8), while ~90% of terminals were functional under 5AP stimulation after elevating $[Mg^{2+}]_o$ for 4 hr (FIGS. 3C and 3D, 1.2 4 hr).

Figure 3F:
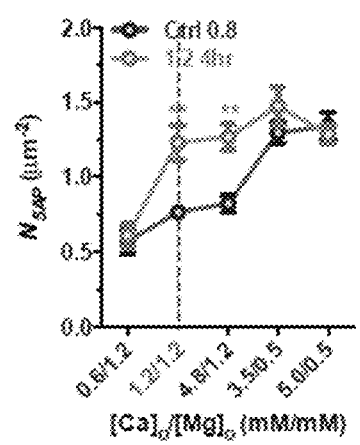

The cellular processes modified after elevation of $[Mg^{2+}]_i$ were then determined. One of the prominent differences between 5AP and 600AP stimulation is the resultant amount of presynaptic $Ca^{2+}$ influx. At the low $[Mg^{2+}]_o$ condition, if terminals have low $Ca^{2+}$ sensitivity, they might not be able to release vesicles in response to 5AP-induced $Ca^{2+}$ influx, but able to release vesicles under the much higher 600AP-induced $Ca^{2+}$ influx. If this hypothesis was true, elevation of $[Ca^{2+}]_o/[Mg^{2+}]$, which is a classic approach to enhance presynaptic $Ca^{2+}$ influx, should be able to turn nonfunctional terminals into functional ones under 5AP bursting stimulation. Experimentally, the $[Ca^{2+}]_o/[Mg^{2+}]_o$ was acutely manipulated in working solution right before FM dye staining. At the low $[Mg^{2+}]_o$ condition (Ctrl 0.8), raising the $[Ca^{2+}]_o/[Mg^{2+}]_o$ from 1 (normal working solution, $[Ca^{2+}]_o$ 1.2 and $[Mg^{2+}]_o$ 1.2 mM) (FIGS. 3E and 3F, dotted line) to 4 ($[Ca^{2+}]_o$ 4.8 and $[Mg^{2+}]_o$ 1.2 mM) induced no increase in $N_{5AP}$ (FIGS. 3E and 3F, Ctrl 0.8). However, strikingly, when $[Ca^{2+}]_o/[Mg^{2+}]_o$ was >7, $N_{5AP}$ increased dramatically up to levels comparable to those at the high $[Mg^{2+}]_o$ condition (1.2 4 hr) (FIGS. 3E and 3F). These data suggest that the primary effect of elevating $[Mg^{2+}]_i$ on the functionality of terminals might be the enhancement of presynaptic $Ca^{2+}$ sensitivity. If so, a decrease in $Ca^{2+}$ influx in terminals at the high $[Mg^{2+}]_o$ condition (1.2 4 hr) might lead to the neutralization of the increase in $N_{5AP}$. Indeed, reducing $[Ca^{2+}]_o/[Mg^{2+}]_o$ to 0.5 ($[Ca^{2+}]_o$ 0.6 and $[Mg^{2+}]_o$ 1.2 mM) led to a significant decrease in $N_{5AP}$ in comparison with that under normal $[Ca^{2+}]_o/[Mg^{2+}]_o$ (FIGS. 3E and 3F), showing that $Mg^{2+}$-induced enhancement of functional terminal density is $Ca^{2+}$ influx-dependent. Note that when $[Ca^{2+}]_o/[Mg^{2+}]_o$ was at extreme (0.5 or ≥7), there were no differences in $N_{5AP}$ at the low (Ctrl 0.8) and high $[Mg^{2+}]_o$ conditions (1.2 4 hr).

Taking these results together, it was concluded that (1) at low $[Mg^{2+}]_o$ conditions (e.g. Ctrl 0.8), approximately half of the terminals failed to release vesicles in response to physiological patterns of input and are thereby in a nonfunctional state; (2) the non-function is due to low presynaptic $Ca^{2+}$ sensitivity, which can be ameliorated by increasing $Ca^{2+}$ influx by either boosting temporal intensity of stimuli or elevating $[Ca^{2+}]_o/[Mg^{2+}]_o$ ratio; (3) elevation of $[Mg^{2+}]_i$ can enhance presynaptic $Ca^{2+}$ sensitivity such that most terminals are capable of releasing vesicles to physiological stimuli, leading to higher functional terminal density at dendritic branches.

Figure 4A:
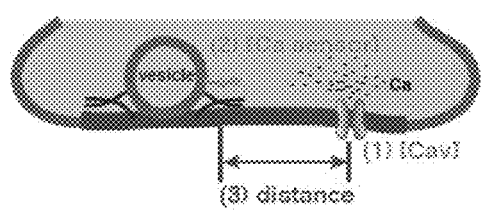
FIGS. 4A-4D are a collection of schematic diagrams, images and graphs showing increased $Ca^{2+}$ sensitivity-related proteins in terminals by elevating intracellular $Mg^{2+}$ levels, according to embodiments of the present disclosure.

The Quantity of $Ca^{2+}$-Sensitivity-Related Proteins in Presynaptic Terminals Determines the Terminal Functionality Under Physiological Conditions To further understand how $[Mg^{2+}]_i$ affects presynaptic $Ca^{2+}$ sensitivity, the potential molecular mechanisms underlying this phenomenon was investigated. Generally, $Ca^{2+}$ sensitivity of presynaptic terminals is determined by three biophysical factors (illustrated in FIG. 4A): (1) the quantity of presynaptic $Ca^{2+}$ channels (mainly $Ca_v2.1$ and $Ca_v2.2$ in hippocampal terminals), which conduct the $Ca^{2+}$ influx; (2) the quantity of $Ca^{2+}$ sensor proteins (mainly Synaptotagmin1 [SYT1] for excitatory central synapses), which couple the $Ca^{2+}$ signals to vesicle release; and (3) the distance from $Ca^{2+}$ channels to vesicle release machinery, which determines the coupling efficacy of the $Ca^{2+}$ influx to the operation of release machinery. The coupling efficacy is regulated by multiple vesicle and active zone proteins (e.g. Rab3, RIM1, Munc13, ELKS, Syntaxin1).

Figure 4B:
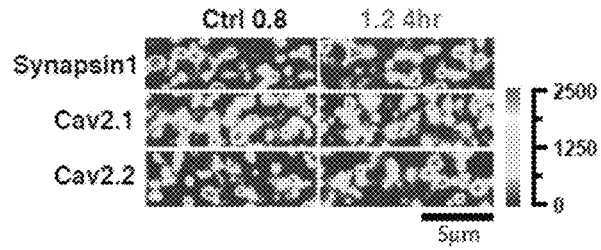
Figure 4C:
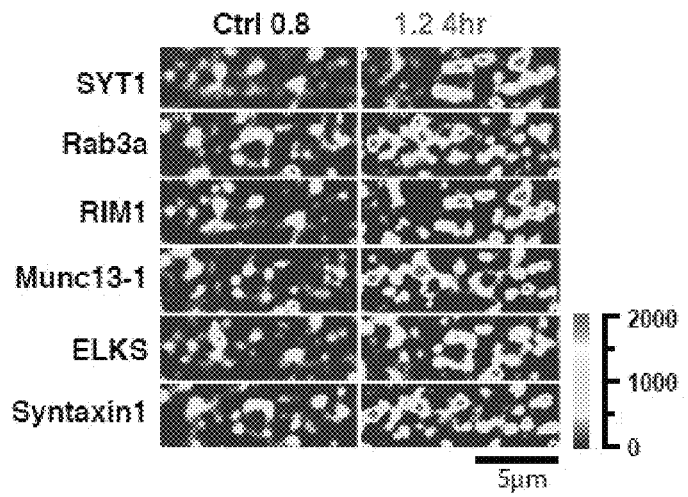
Figure 4D:
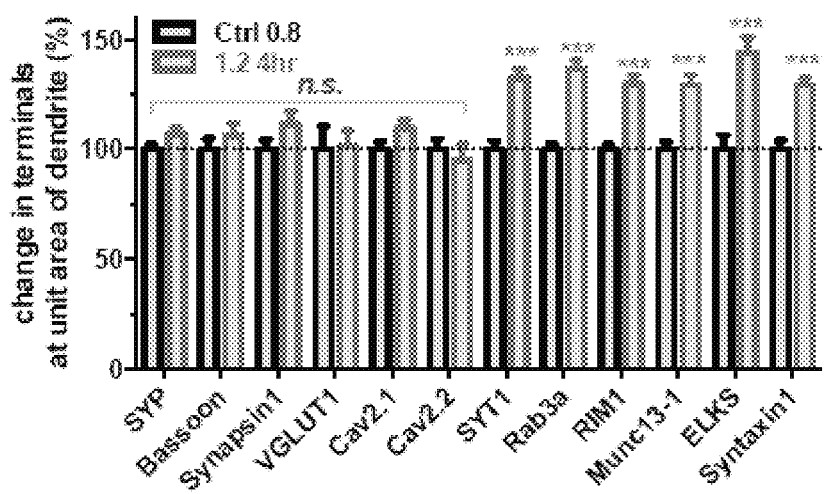

To address these three possibilities, the profiles of protein expression in terminals at the low (Ctrl 0.8) versus the high $[Mg^{2+}]_o$ condition (1.2 4 hr) were compared using IF staining. There was no difference in the expression level of $Ca_v2.1$ and $Ca_v2.2$ per area of dendrites (FIGS. 4B and 4D), eliminating the first possibility. However, the expression of $Ca^{2+}$ sensor protein (SYT1) and coupling proteins (e.g. Rab3a, RIM1, Munc13-1, ELKS, Syntaxin1) were significantly higher in terminals at the high $[Mg^{2+}]_o$ condition (30-44%, $p<0.001$) (FIGS. 4C and 4D). These data, together with the observation that the expression of structural (vesicle and active zone) presynaptic proteins (SYP, Bassoon, VGLUT1 and Synapsin1) did not change (FIGS. 3A and 3B, 4B) suggest that elevation of $[Mg^{2+}]_i$ increased presynaptic $Ca^{2+}$ sensitivity via enhancing the expression of presynaptic proteins critical for controlling presynaptic $Ca^{2+}$ efficacy (these proteins are referred to hereafter as presynaptic $Ca^{2+}$-sensitivity-related proteins).

FIGS. 4A-4D. Elevating $[Mg^{2+}]_i$ leads to increased $Ca^{2+}$-sensitivity-related proteins in terminals. (FIG. 4A) Schematic cartoon illustrates the three critical biophysical factors affecting presynaptic vesicle release. (FIGS. 4B and C) Immunofluorescence. No change of quantity of Synapsin1, $Ca_v2.1$ and $Ca_v2.1$ (FIG. 4B), but remarkable increase in $Ca^{2+}$-sensitivity-related proteins at dendritic branches (FIG. 4C) after elevating $[Mg^{2+}]_o$ for 4 hr. Pseudo-color scale: fluorescent intensity. (FIG. 4D) Elevating $[Mg^{2+}]_o$ for 4 hr led to increase in $Ca^{2+}$-sensitivity-related protein positive fluorescence in terminals at dendritic branches (n=10-21 coverslips for each point). The mean±SEM of coverslips was presented. Two-tailed Student's t-test, comparing 1.2 4 hr to Ctrl 0.8, n.s. no significance, ***$p<0.001$.

Role of $[Mg^{2+}]_i$ in Controlling the Efficiency of Axonal Transport of $Ca^{2+}$-Sensitivity-Related Proteins within Several Hours Further experiments were carried out to explore how elevating $[Mg^{2+}]_i$ promoted the augmentation of $Ca^{2+}$-sensitivity-related proteins in terminals. Generally, the quantity of proteins in terminals depends on the three major processes involved in the protein life cycle: (1) synthesis, (2) transport, and (3) degradation, so whether $[Mg^{2+}]_i$ affected any of these processes in regard to $Ca^{2+}$-sensitivity-related proteins in terminals was investigated.

First, the quantity of SYP and $Ca^{2+}$-sensitivity-related proteins from total proteins extracted from entire neurons at the low (Ctrl 0.8) and high $[Mg^{2+}]_o$ (1.2 6 hr) conditions was compared by Western blot. Surprisingly, the quantity of each protein at the high $[Mg^{2+}]_o$ condition was not significantly higher (at least within 6 hr) than that at the low $[Mg^{2+}]_o$ condition (FIG. 5A), ruling out the possibility that elevating $[Mg^{2+}]_i$ could promote the detectable enhancement of synthesis of $Ca^{2+}$-sensitivity-related proteins rapidly (within 6 hr).

FIGS. 5A-5I. Elevating $[Mg^{2+}]_i$ might increase the efficiency of axonal transport of $Ca^{2+}$-sensitivity-related proteins. (FIG. 5A) Western blot detection showed no significant increase in the total protein levels of each $Ca^{2+}$-sensitivity-related protein or SYP after elevating $[Mg^{2+}]_o$ for 6 hr (n=12 coverslips from 4 batches). (FIG. 5B) The immunoreactivity of Rab3a in a soma island from the culture coverslips before and after elevating $[Mg^{2+}]_o$ for 4 hr. The pseudo-colored images were the magnifications of the local somatic or terminal regions marked in the large images. Stars $s_1$-$s_4$: examples of immunoreactive cell bodies. Dashed boxes $d_1$-$d_6$: representative terminal regions. Pseudo-color scale: fluorescent intensity; the upper one was for $s_1$-$s_4$ and the lower one was for $d_1$-$d_6$. (FIG. 5C) Significant decreases in $Ca^{2+}$-sensitivity-related proteins in somatic area after elevating $[Mg^{2+}]_o$ for 4 hr (analyzed from the same raw data as in FIG. 4D, 50-98 cell bodies). Dotted line represents levels of proteins at $[Mg^{2+}]_o$ 0.8 normalized to 100%. (FIG. 5D) Quantity of immunostained SYT1 at terminals (n=6-8 coverslips for each data bar) or soma (40-55 cells from the same AOIs) changed in opposite directions after elevating $[Mg^{2+}]_o$ from 0.6 to 0.75-1.2 mM (in gradient) for 4 hr. Dotted line represents initial SYT1 at Terminal and Soma, normalized to 0% change. Pseudo-colored images represented the immunoreactivity in somatic area at different $[Mg^{2+}]_o$ levels. Pseudo-color scale: fluorescent intensity. (FIGS. 5E and 5F) Blocking axonal transport by 0.5 mM Colchicine (Colch) caused a decrease in proteins in terminals at low (FIG. 5E) and high $[Mg^{2+}]_o$ conditions (FIG. 5F) (n=8-10 coverslips for E and 10-15 coverslips for F). Dotted lines represent initial protein levels before addition of Colch, normalized to 100%. (FIGS. 5G and 5H) Blocking axonal transport by 0.5 mM Colch led to a decrease in $N_{SAP}$ but no effect on $[Mg^{2+}]_i$ compared to not adding Colch (blue dashed lines) (n=5-6 coverslips for FIG. 5G and 5-8 coverslips for FIG. 5H). Dotted line represented the initial $[Mg^{2+}]_i$ and $N_{SAP}$ normalized to 100%. (FIG. 5I) Schematic cartoon: intracellular $Mg^{2+}$ might majorly affect axonal transport efficiency, but not affect protein synthesis or degradation within a few hours. The mean±SEM of all coverslips was presented. Two-tailed Student t-test for comparing 1.2 4 hr to Ctrl 0.8 (FIG. 5C) and comparing pre and post treatment values (FIGS. 5D-5H), *$p<0.05$, $p<0.01$, *$p<0.001$.

Figure 5B:
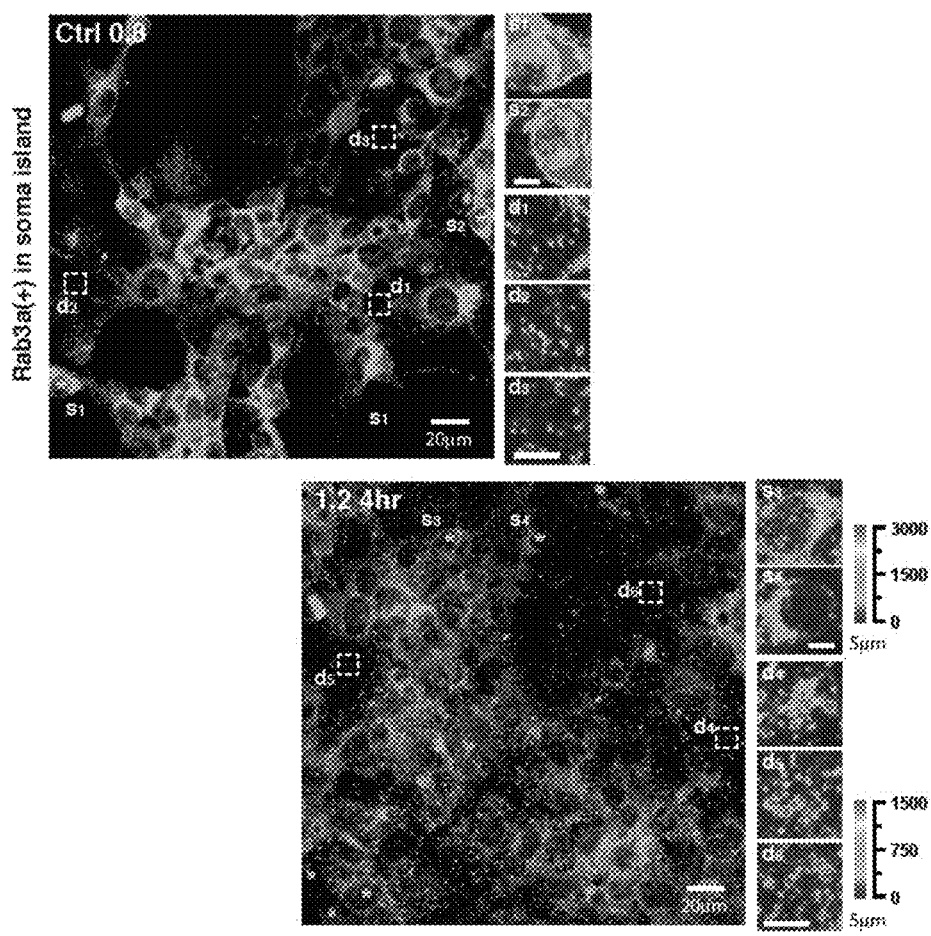
Figure 5C:
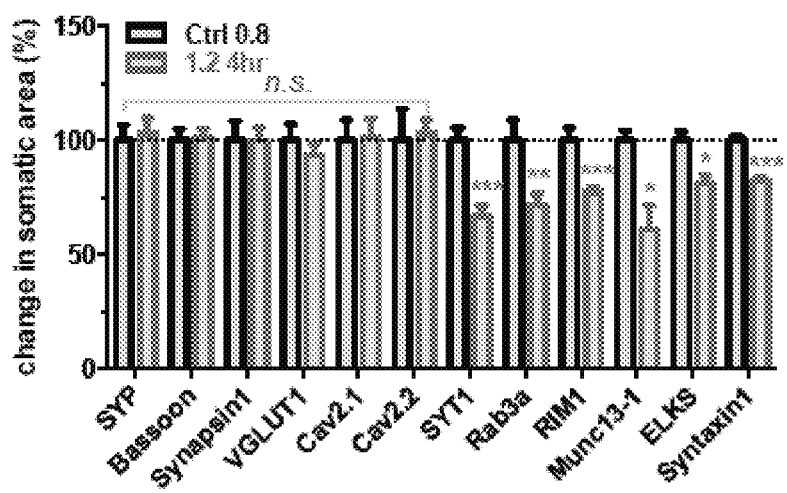

Next, it was determined whether elevating $[Mg^{2+}]_i$ could promote the transport of $Ca^{2+}$-sensitivity-related proteins from soma to axonal terminals. Interestingly immunoreactive fluorescence for the $Ca^{2+}$-sensitivity-related protein Rab3(+) decreased in somatic area (FIG. 5B $s_1$-$s_2$ vs. $s_3$-$s_4$) but increased in terminals (FIG. 5B $d_1$-$d_3$ vs. $d_4$-$d_6$). This result was also found for other $Ca^{2+}$-sensitivity-related proteins tested (FIG. 5C; from the same experiment as in FIG.

Figure 5D:
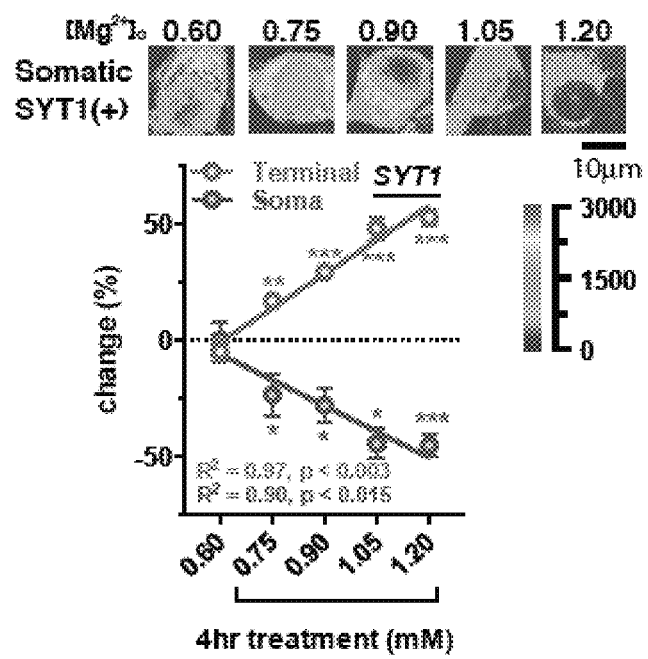

4D). Conversely, after 4 hr high $[Mg^{2+}]_o$, those proteins whose immunoreactivity changed little in terminals at dendrites (SYP, Bassoon, Synapsin1, VGLUT1, $Ca_v2.1$ and $Ca_v2.2$) (FIG. 4D) also had constant immunoreactivity in the somatic area (FIG. 5C, from the same experiments as in FIG. 4D). These data highly suggested that elevation of $[Mg^{2+}]_i$ might accelerate the transport of $Ca^{2+}$-sensitivity-related proteins from soma to terminals selectively. To study this phenomenon quantitatively, the changes of the quantity of SYT1 in the somatic area and terminals at dendrites by IF after elevating $[Mg^{2+}]_o$ from 0.6 to 0.75-1.2 mM in gradient for 4 hr (thereby $[Mg^{2+}]_i$ could be clamped at different levels). The immunoreactivity of SYT1 in the somatic area (FIG. 5D, upper panel) and terminals at dendrites changed in opposite directions, linearly proportional to the $Mg^{2+}$ level (FIG. 5D, linear regression).

Figure 5E:
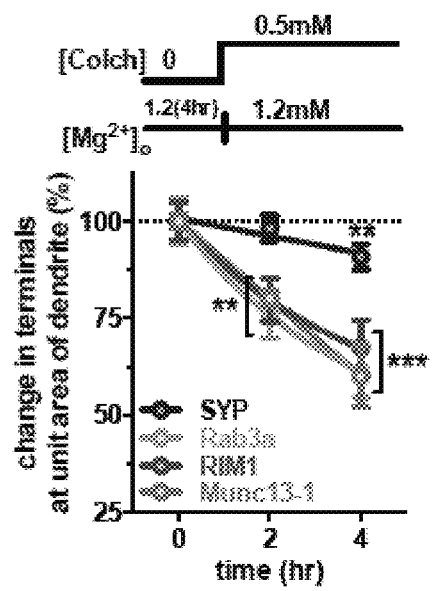
Figure 5F:
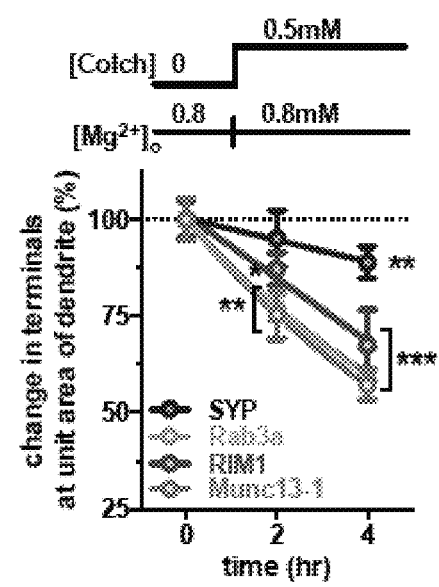

Third, the effects of elevating $[Mg^{2+}]_i$ on the rate of protein degradation in terminals was examined. Assuming that presynaptic terminals do not have the capacity to synthesize new $Ca^{2+}$-sensitivity-related proteins (no evidence has been found that they do), the quantity of presynaptic $Ca^{2+}$-sensitivity-related proteins at equilibrium would be largely determined by the balance of protein transport and degradation. Therefore, if axonal transport is blocked, the rate of protein decline would reflect the rate of protein degradation. When axonal transport was blocked by 0.5 mM Colchicine (Colch), the concentration of the presynaptic proteins studied decreased linearly, as a function of the amount of blocking time (FIGS. 5E and 5F), albeit at varying rates. The rate of protein degradation (half-life) for the $Ca^{2+}$-sensitivity-related proteins (e.g. Rab3a, RIM1 and Munc13-1) (several hours) was much faster than that for structure-protein SYP (several days). Interestingly, the elevation of $[Mg^{2+}]_i$ did not alter the degradation rate of presynaptic proteins, indicating that degradation rate was not part of the mechanism by which increased $[Mg^{2+}]_i$ altered presynaptic $Ca^{2+}$ sensitivity (FIGS. 5E and 5F).

Altogether, these data suggested that the $Ca^{2+}$-sensitivity-related proteins had a relatively fast degradation rate and thereby their quantities in terminals at dendrites were strongly dependent upon the efficiency of axonal transport. The elevation of $[Mg^{2+}]_i$ likely promoted the augmentation of $Ca^{2+}$-sensitivity-related proteins in terminals by increasing the efficiency of their transport from soma to terminals, which ensured sufficient $Ca^{2+}$ sensitivity for AP-dependent vesicle turnover (illustrated in FIG. 5I).

Figure 5G:
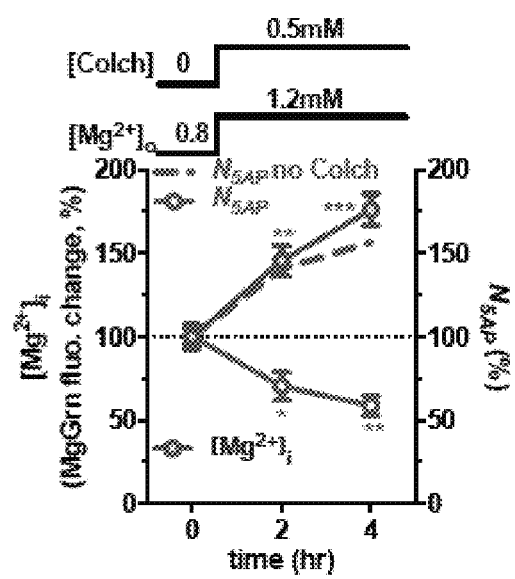
Figure 5H:
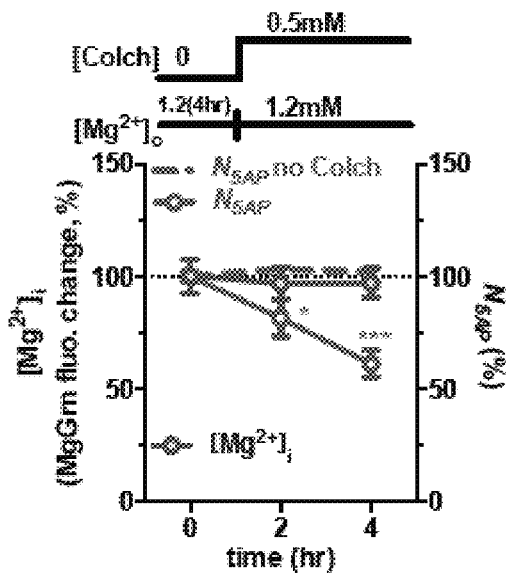
Figure 5I:
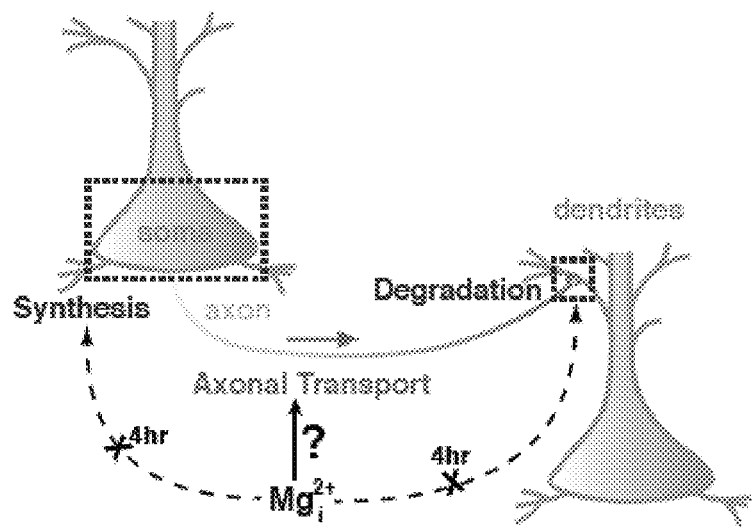

Based on these data, it was inferred that impairment of axonal transport would reduce the density of functional terminals immediately (within hours). To validate this, the temporal changes of $N_{5AP}$ after blockade of axonal transport by Colch was measured. Colch treatment did not prevent elevation of $[Mg^{2+}]_i$ after increasing $[Mg^{2+}]_o$ but it prevented the increase in $N_{5AP}$ (FIG. 5G). Furthermore, blocking axonal transport at the high $[Mg^{2+}]_o$ condition caused a remarkable reduction of $N_{5AP}$, without change of $[Mg^{2+}]_i$ (FIG. 5H). These data demonstrate the critical role of ongoing axonal transport in maintaining functional status of terminals.

Local Energy Supply isCed by Elevation of Intracellular $Mg^{2+}$

The effects of elevating $[Mg^{2+}]_i$ on the spatial distribution and function of mitochondria was studied. The function of each mitochondrion was quantified by measuring its membrane potential ($\Delta\Psi$), using the $\Delta\Psi$-sensitive fluorescent dye JC-1. $\Delta\Psi$ increased by ~39% after elevating $Mg^{2+}$ for 4 hr and this increase persisted up to several weeks (FIGS. 6A and 6B). The number of mitochondria per unit area of distal dendritic branches ($N_{mito}$) also increased, by ~20% (FIG. 6B). Since $N_{mito}$ and $\Delta\Psi$ are two key parameters for the determination of mitochondrial function, the product of $N_{mito}$ and $\Delta\Psi$ was used to represent the total mitochondrial function per unit area of dendritic branches in the synaptic network, and found $N_{mito} \times \Delta\Psi$ increased by ~68% after elevating $[Mg^{2+}]_o$ for 4 hr (FIG. 6B).

FIGS. 6A-6D. Elevating $[Mg^{2+}]_i$ increases general mitochondrial function and intracellular ATP. (FIG. 6A) The mitochondrial potential (A P) was determined by the ratio of aggregate and monomer of JC-1 fluorescence. (FIG. 6B) Both mitochondrial density ($N_{mito}$) and general mitochondrial function ($N_{mito} \times \Delta\Psi$) in distal branches were significantly enhanced after elevating $Mg^{2+}$ level for 4 hr (19.4±2.9% and 67.8±12.4%, n=14 coverslips) and for long term (>48 hr) (19.6±2.1% and 56.2±6.5%, n=20 coverslips). Dotted line represents initial value of $N_{mito}$, $N_{mito} \times \Delta\Psi$ and $\Delta\Psi$ normalized to 100%. (FIG. 6C) Intracellular ATP concentration ($[ATP]_i$) was linearly correlated with $N_{mito} \times \Delta\Psi$ at equilibrium (altering $[Mg^{2+}]_o$ for >12 hr) (n=7 coverslips). (FIG. 6D) Absolute temporal changes of $N_{mito}$ ($\Delta N_{mito}$) and $[Mg^{2+}]_i$ ($\Delta[Mg^{2+}]_i$) exhibited a linear correlation, either by elevating $[Mg^{2+}]_o$ or by administering 1 µM Imipramine (IM) for 2-4 hr (n=5-11 coverslips). Each point represented the changes of both $\Delta N_{mito}$ and $\Delta[Mg^{2+}]_i$ (using sister cultures from the same batch) at different time after a treatment, and the colored numbers beside each point indicated the hours after the treatment. These data were collected from 2 individual batches of measurements. The mean±SEM of coverslips was presented. Two-tailed Student t-test for (FIG. 6B) comparing both 1.2 4 hr and 1.2 LT to Ctrl 0.8, ***p<0.001. Linear regression for (FIGS. 6C and 6D).

Next, whether increased $N_{mito} \times \Delta\Psi$, after elevation of $[Mg^{2+}]_o$ led to increased was examined $[ATP]_i$. The range of $[Mg^{2+}]_o$ at 0.4-1.2 mM was set for more than 12 hr before measuring $[ATP]_i$ to ensure equilibrium of the cytoplasmic ATP concentration. Indeed, as $N_{mito} \times \Delta\Psi$ increased linearly with the elevation of $[Mg^{2+}]_o$, $[ATP]_i$ also increased linearly with $N_{mito} \times \Delta\Psi$ (FIG. 6C). To directly show that the extent of $[Mg^{2+}]_i$ influenced mitochondrial function at the local area of distal branches, the correlation between the change of $[Mg^{2+}]_i$ ($\Delta[Mg^{2+}]_i$) and the change of $N_{mito}$ ($\Delta N_{mito}$) was plotted. Indeed, $\Delta N_{mito}$ was linearly correlated with $\Delta[Mg^{2+}]_i$ (FIG. 6D).

These data suggest that the elevation of $[Mg^{2+}]_i$ increased energy supply in local area of the network.

Local Energy Supply, $Ca^{2+}$-Sensitivity-Related Proteins and Functional Terminal Density Whether the increased quantity of $Ca^{2+}$-sensitivity-related proteins at terminals and subsequently the functionality of terminals as a result of elevated $[Mg^{2+}]_i$ was due to enhanced mitochondrial function and local energy supply at dendritic branches was determined. To address this, whether the quantity of $Ca^{2+}$-sensitivity-related proteins or functional terminal density was correlated with mitochondrial density since both are upregulated after the elevation of $[Mg^{2+}]_i$ was examined (FIGS. 4D, 6B and 6D). Mitochondria were stained with the fluorescent marker MitoView™ 633. Then, at the same region, functional terminals responding to 5AP bursts were labeled by FM1-43. Subsequently, structure- and $Ca^{2+}$-sensitivity-related proteins in terminals were stained by IF at the low and high $[Mg^{2+}]_o$ conditions (FIG. 7A). The nonfunctional terminals (the SYP positive but FM 1-43 negative puncta) usually lacked some of the $Ca^{2+}$-sensitivity-related proteins, but the type of proteins whose expression was low varied in different nonfunctional terminals. For example, in terminal 1 of FIG. 7A, the expression of SYT1 and ELKS was relatively low, while in terminal 2, the expression of Rab3a, RIM1 and Munc13-1 was relatively low (FIG. 7A white circles: terminal 1, 2). This observation suggested that it was the inadequate expression of multiple $Ca^{2+}$-sensitivity-related proteins, but not specific one of them that made a presynaptic terminal nonfunctional. Therefore, $\Sigma Q_{proteins}$ was used to represent the total quantity of $Ca^{2+}$-sensitivity-related proteins (see "Materials and Methods").

FIGS. 7A-7C. Linear correlations between local energy supply, $Ca^{2+}$-sensitivity-related proteins in terminals and functional terminal density. (FIGS. 7A-7D) At the low and high $[Mg^{2+}]_o$ conditions, mitochondria, functional terminals and $Ca^{2+}$-sensitivity-related proteins were marked at the same dendritic branch (FIG. 7A). The numbers 1 and 2 indicated the positions of two nonfunctional terminals marked by white circles. No correlation between normalized quantity (Q) of SYP ($Q_{SYP}$) and $N_{mito}$, whereas linear correlation between total amount of $Ca^{2+}$-sensitivity-related proteins ($\Sigma Q_{proteins}$) and $N_{mito}$ (FIG. 7B). Relative quantity of $Ca^{2+}$-sensitivity-related proteins to structure-related protein SYP, i.e. $\Sigma Q_{proteins}/Q_{SYP}$, was linearly correlated with $N_{mito}$ (FIGS. 7C and 7D, circles), meanwhile the density of functional terminals ($N_{5AP}$) was also linearly correlated with $N_{mito}$ (FIGS. 7C and 7D, diamonds) at the low (FIG. 7C) and high $[Mg^{2+}]_o$ conditions (FIG. 7D) (n=9 AOIs from 1 coverslip for each group, the two coverslips were from the same culturing dish). Each point represented an AOI (FIGS. 7B-7D). Pseudo-color scale: fluorescent intensity. (FIG. 7E) The change of $\Sigma Q_{proteins}$ ($\Delta \Sigma Q_{proteins}$) was linearly correlated with the change of $[ATP]_i$ ($\Delta[ATP]_i$) after different treatments. (FIG. 7F) $\Delta N_{5AP}$ and $\Delta[ATP]_i$ exhibited linear correlation after different treatments. For (FIGS. 7E and 7F), the treatments included adding 50 nM FCCP for 16 hr, reducing Glucose concentration from 28 to 2 mM in culture medium for 12 hr and elevating $[Mg^{2+}]_o$ from 0.8 to 1.0 or 1.2 mM for 4 hr (n=4-6 coverslips for E; n=5-8 coverslips for FIG. 7F). The percentage in (FIGS. 7E and 7F) was normalized to the mean of Ctrl 0.8 group (0%). The experiments were performed using sister cultures for each treatment. The mean±SEM of coverslips was presented. Linear regression for FIGS. 7B-7F.

When the relationship of $N_{mito}$ with the quantity of the structure-related protein SYP ($Q_{SYP}$) and with $\Sigma Q_{proteins}$ was compared, $\Sigma Q_{proteins}$ was correlated with $N_{mito}$, while $Q_{SYP}$ was not (FIG. 7B lower panel). Elevating $[Mg^{2+}]_o$ increased both $\Sigma Q_{proteins}$ and $N_{mito}$ (FIGS. 7B-7D). The correlation between $\Sigma Q_{proteins}$, the ratio of $\Sigma Q_{proteins}/Q_{SYP}$ and $N_{mito}$ remained (FIG. 7B upper, FIGS. 7C and 7D). Most importantly, $N_{5AP}$ at the same local area was also linearly correlated with $N_{mito}$ (FIGS. 7C and 7D). Therefore, the close linear correlations between $\Sigma Q_{proteins}$, $\Sigma Q_{proteins}/Q_{SYP}$, $N_{5AP}$ and $N_{mito}$ support the notion that local energy supply provided by mitochondria might be important for maintaining high levels of $Ca^{2+}$-sensitivity-related proteins in terminals, which in turn determine the density of functional terminals.

To demonstrate the causal relationship between energy supply and $N_{5AP}$, whether modification of energy supply would affect both $\Sigma Q_{proteins}$ and $N_{5AP}$ concurrently was tested. Energy supply was increased by elevating $[Mg^{2+}]_o$ (from 0.8 to 1.0 or 1.2 mM for 4 hr), or decreased by either adding FCCP (disturbs mitochondrial function by preventing the $H^+$-coupling of respiratory chain) or by lowering the extracellular glucose concentration (from 28 to 2 mM) for 12 hr in sister cultures from the same batch of cultured neurons, and then $[ATP]_i$, $\Sigma Q_{proteins}$ and $N_{5AP}$ under these conditions were compared. Using cultures under the low $[Mg^{2+}]_o$ condition (Ctrl 0.8) as a control, the relationship between the change of $[ATP]_i$ and the change of $\Sigma Q_{proteins}$ and $N_{5AP}$ was plotted. The increase or decrease in $[ATP]_i$ was linearly correlated with the increase or decrease in $\Sigma Q_{proteins}$ and $N_{5AP}$ (FIGS. 7E and 7F).

Taking all the data together, it was concluded that local energy supply is one of major factors that determine functional terminal density.

Correlation Between Quantity of $Ca^{2+}$-Sensitivity-Related Proteins and Mitochondrial Density in Intact Animals Finally, whether the in vitro findings could be verified in intact animals was determined. Mature male Sprague-Dawley rats (16 months old) were treated with Magnesium L-Threonate (MgT) in drinking water. This treatment is known to be effective in elevating $[Mg^{2+}]_{CSF}$. After 8 months of MgT supplement (24 months old), the animals were sacrificed, the Hippocampus CA1 Stratum Radiatum region of the brain were dissected, and both electron microscopy (EM) and IF were conducted.

First it was determined whether MgT supplementation could modify mitochondrial density ($N_{mito}$). $N_{mito}$ (number of mitochondria per unit area of image) was measured in EM images of each animal (FIG. 8A). Mean $N_{mito}$ in MgT group (0.47±0.02 $\mu m^{-2}$, N=11 rats) was ~26% higher than that in control group (0.37±0.02 $\square m^{-2}$, N=10 rats) (Kolmogorov-Smirnov test, p<0.01) (FIG. 8B). The extent of the increase in $N_{mito}$ by MgT supplementation in intact animals was similar to that in cultured neurons (FIG. 7B).

Figure 8C:
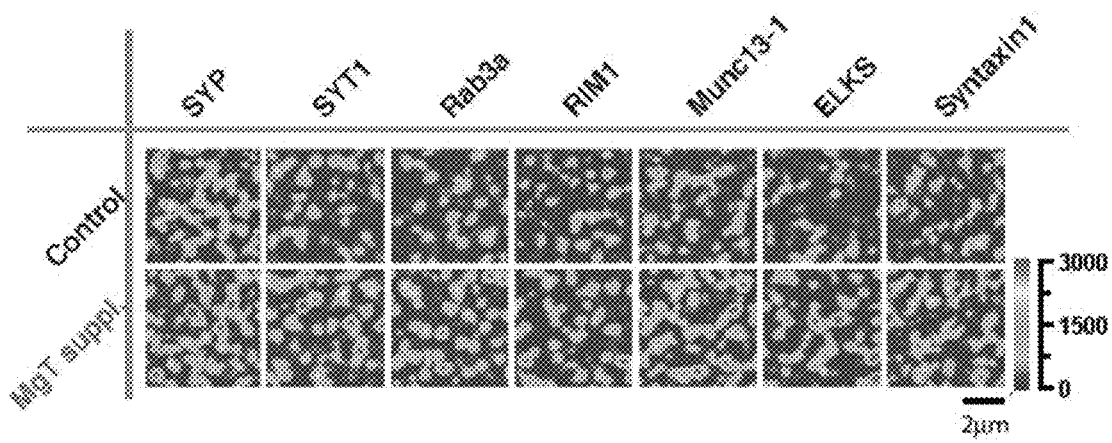
Figure 8D:
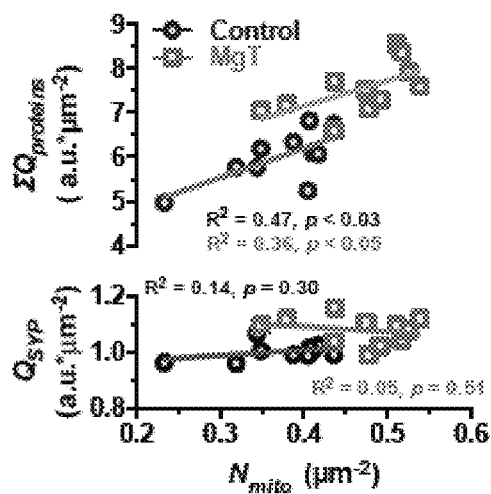
Figure 8E:
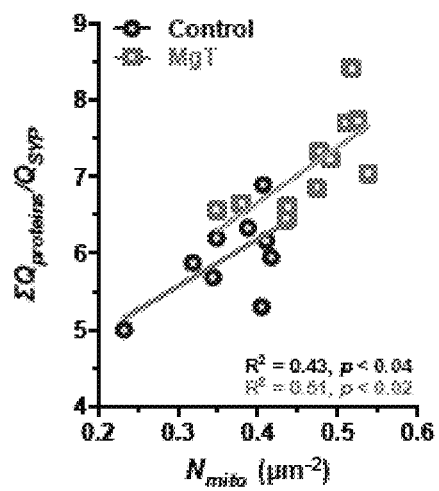

FIGS. 8A-8E. Quantity of $Ca^{2+}$-sensitivity-related proteins versus density of mitochondria in intact animals. (FIG. 8A) Electron Microscopy (EM) images of Hippocampus CA1 Stratum Radiatum region (HP/CA1/SR) from 24-months-old Control and MgT-supplemented (for 8 months) rats (m, mitochondrion [red colored]; s, synapse). (FIG. 8B) Density of mitochondria ($N_{mito}$, number of mitochondria per area of 70 nm brain slice) in MgT group (0.47±0.02 $\mu m^{-2}$, n=11 rats) was 25.9% higher than Control group (0.37±0.02 $\mu m^{-2}$, n=9 rats) (Kolmogorov-Smirnov test, p<0.01). (FIG. 8C) Immunostained structure-related protein SYP and $Ca^{2+}$-sensitivity-related proteins in 70 nm ultrathin slices from adjacent tissue blocks in HP/CA1/SR of the same rats as in (FIGS. 8A and 8B). Quantity of $Ca^{2+}$-sensitivity-related proteins was higher in MgT group than in Control group. Pseudo-color scale: fluorescent intensity. (FIG. 8D) Normalized total quantity of each protein (Q) was calculated for each rat. $Q_{SYP}$ was not correlated with $N_{mito}$ (FIG. 8D lower panel) Total amount of $Ca^{2+}$-sensitivity-related proteins ($\Sigma Q_{proteins}$) was linearly correlated with $N_{mito}$ for both groups and the correlation curve was positively shifted in MgT group (FIG. 8D upper panel) (Kolmogorov-Smirnov test, p<0.0005). (FIG. 8E) Relative quantity of $Ca^{2+}$-sensitivity-related proteins to SYP, i.e. $\Sigma Q_{proteins}/Q_{SYP}$, was linearly correlated with $N_{mito}$, and the linear correlation was positively shifted in MgT group (Kolmogorov-Smirnov test, p<0.003). Linear regression for (FIGS. 8D and 8E).

Next, the expression of structure-related (e.g. SYP) and $Ca^{2+}$-sensitivity-related proteins (e.g. SYT1, Rab3a, RIM1, Munc13-1, ELKS and Syntaxin1) was checked in 70 nm ultrathin slices by IF. The total fluorescent intensity of immunoreactive puncta of $Ca^{2+}$-sensitivity-related proteins was higher in MgT group than that in control group (FIG. 8C). The quantity of each protein (Q) was calculated in each individual rat, and no correlation between $Q_{SYP}$ and $N_{mito}$ was found for each rat in both groups (FIG. 8D lower panel). However, $\Sigma Q_{proteins}$ (total amount of immunoreactive $Ca^{2+}$- sensitivity-related proteins) was linearly correlated with $N_{mito}$ in both groups, and MgT treatment positively shifted the correlation curve (FIG. 8D upper panel). Thus, the data from intact rats were in agreement with the in vitro data (FIG. 7B). On average, $\Sigma Q_{proteins}$ was ~25% higher in MgT group (Kolmogorov-Smirnov test, p<0.0005) than that in control group, suggesting that the administration of MgT can promote the presence of $Ca^{2+}$-sensitivity-related proteins in the Stratum Radiatum layer of CA1.

Furthermore, the quantity of $Ca^{2+}$-sensitivity-related proteins relative to the structure-related protein SYP (i.e. $\Sigma Q_{proteins}/Q_{SYP}$) was measured, and was found to linearly correlate with $N_{mito}$ in both control and MgT groups (FIG. 8E). After MgT supplementation, both $N_{mito}$ and $\Sigma Q_{proteins}/Q_{SYP}$ increased, maintaining the linear correlation between each other (FIG. 8E). These data were also similar to the in vitro data (FIGS. 7C and 7D).

Altogether these in vivo results were in agreement with the in vitro findings, and further supported the hypothesis that $Mg^{2+}$ plays an important role in controlling mitochondrial density in branches, which in turn determines the expression of $Ca^{2+}$-sensitivity-related proteins in terminals.

Figure 9:
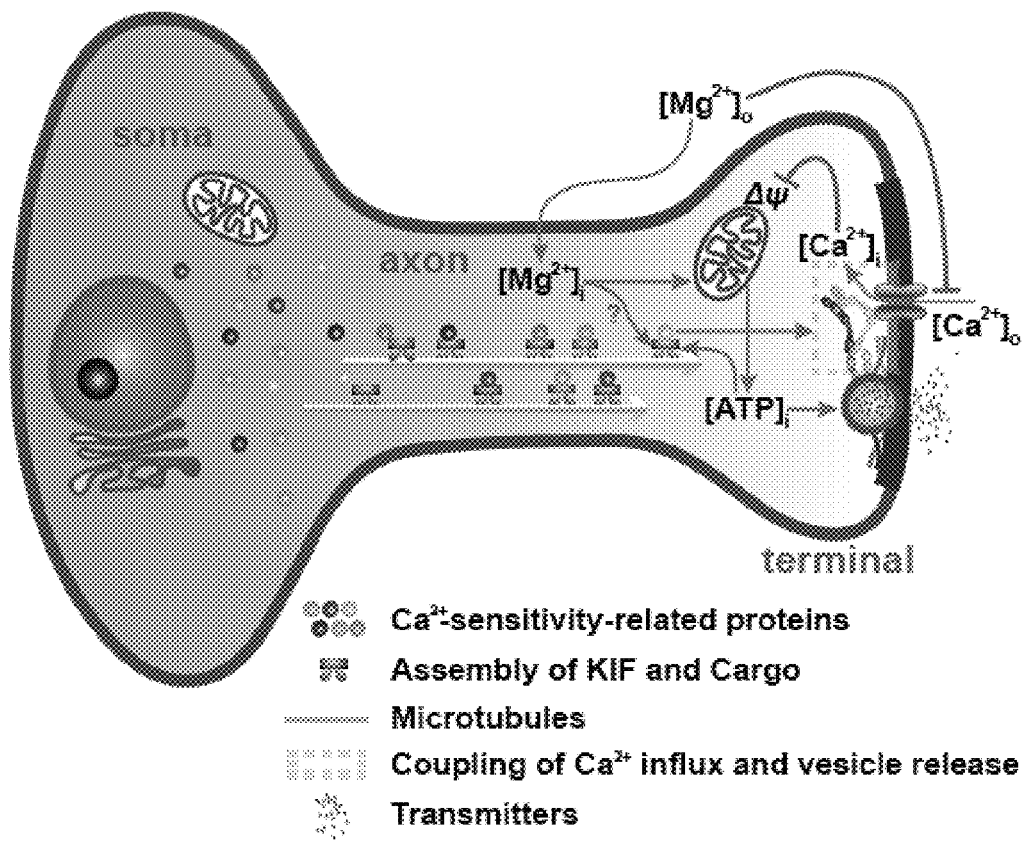
FIG. 9 is a schematic diagram depicting a model for the regulation of functionality of a terminal by intracellular $Mg^{2+}$, according to embodiments of the present disclosure.

This study showed that functionality of presynaptic terminals is likely determined by the amount of $Ca^{2+}$-sensitivity-related proteins in terminals, and the molecular mechanisms of $Mg^{2+}$ in regulating presynaptic functional terminal density (FIG. 9).

FIG. 9. Regulation of functionality of a terminal by intracellular $Mg^{2+}$. Schematic cartoon to illustrate the regulation of presynaptic functionality at a single terminal.

↑$[Mg^{2+}]_i$→↑Mitochondria→↑$[ATP]_i$→↑Axonal transport efficiency→↑$Ca^{2+}$-sensitivity-related proteins→↑$Ca^{2+}$ sensitivity→Terminal in functional state Example 2: Intracellular Magnesium is a Negative Regulator of Terminal Probability of Transmitter Release It was found that the probability of release (Pr) of excitatory synapses are strongly inhibited by increasing intracellular magnesium concentration $[Mg^{2+}]_i$. In fact, Pr of synaptic terminals was inversely correlated with $[Mg^{2+}]_i$. Elevation of $[Mg^{2+}]_i$ by increase in extracellular $[Mg^{2+}]$ ($[Mg^{2+}]_o$) led to the proportional reduction of Pr of synaptic terminals.

Interestingly, in contrast to non-selective inhibitors of neural activity, inhibition of Pr by $[Mg^{2+}]_i$ depended upon input type. $[Mg^{2+}]_i$ could profoundly inhibit transmission in response to a single action potential input (FIGS. 25Aa to 25B), negatively regulating spontaneous (i.e. background) neural activity. Thus, intracellular magnesium is a negative regulator of terminal probability of transmitter release. The higher the intracellular magnesium, the lower the probability of transmitter release.

Figure 25A:
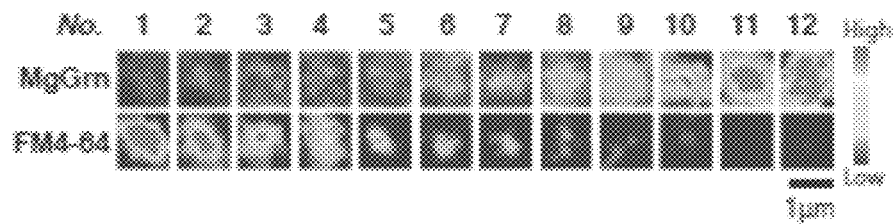
FIGS. 25Aa, 25Ab, 25Ac, and 25B are a collection of graphs and images showing reduction in the probability of synaptic release (Pr) in neurons in response to single action potential input, by increasing $[Mg^{2+}]_i$, according to embodiments of the present disclosure.
Figure 25A:
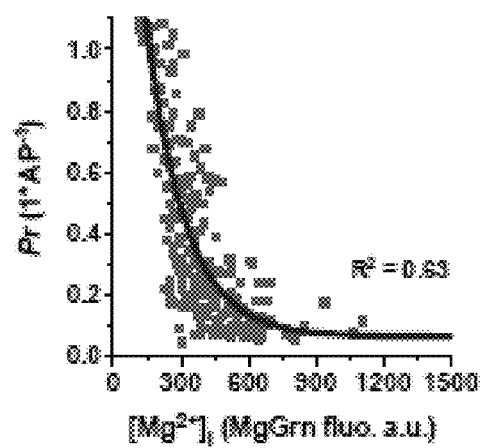
Figure 25A:
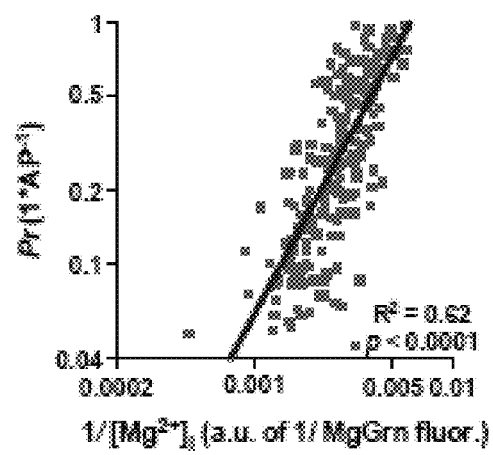
Figure 25B:
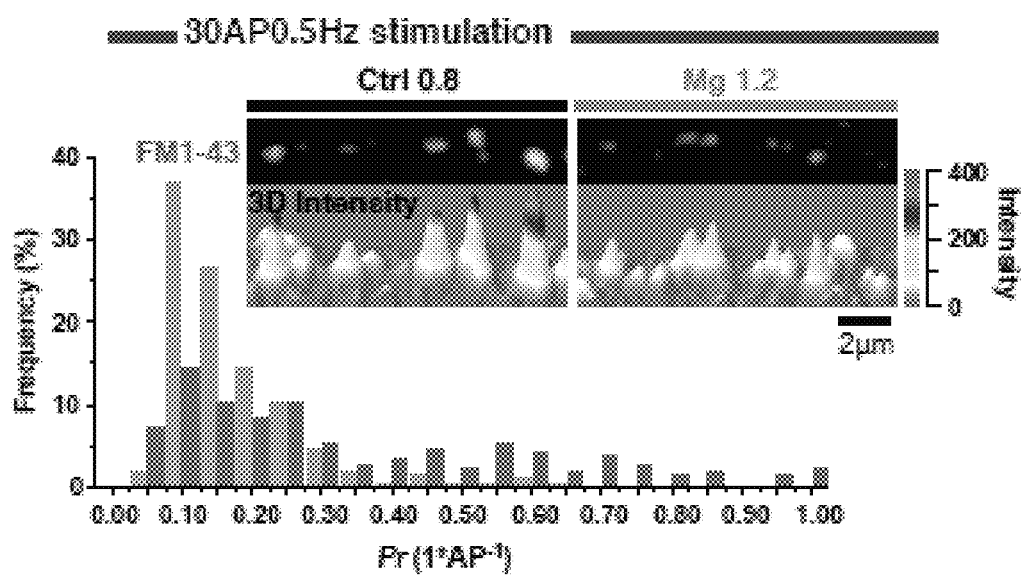

FIGS. 25Aa to 25B. Intracellular $Mg^{2+}$ is a negative regulator of Pr. (FIG. 25Aa-25Ac) Inverse relationship between Pr and intracellular $Mg^{2+}$ concentration ($[Mg^{2+}]_i$) in individual boutons. For individual terminals, the higher the $[Mg^{2+}]_i$, the lower the Pr. (FIG. 25Aa) $[Mg^{2+}]_i$ and Pr in individual boutons were determined by Magnesium Green (MgGrn) and FM4-64, respectively. (FIG. 25Ab) Pr was negatively associated with $[Mg^{2+}]_i$ in individual boutons in a synaptic network. (FIG. 25Ac) Pr was linearly correlated with $1/[Mg^{2+}]_i$. (FIG. 25B) $[Mg^{2+}]_i$ can regulate Pr, demonstrating a causal relationship between $[Mg^{2+}]_i$ and Pr. Extracellular $Mg^{2+}$ concentration ($[Mg^{2+}]_o$) was elevated from 0.8 to 1.2 mM for four hours to increase $[Mg^{2+}]_i$. As a result of increased $[Mg^{2+}]$, the distribution of Pr was shifted to the left, indicating that Pr was reduced.

Figure 26A:
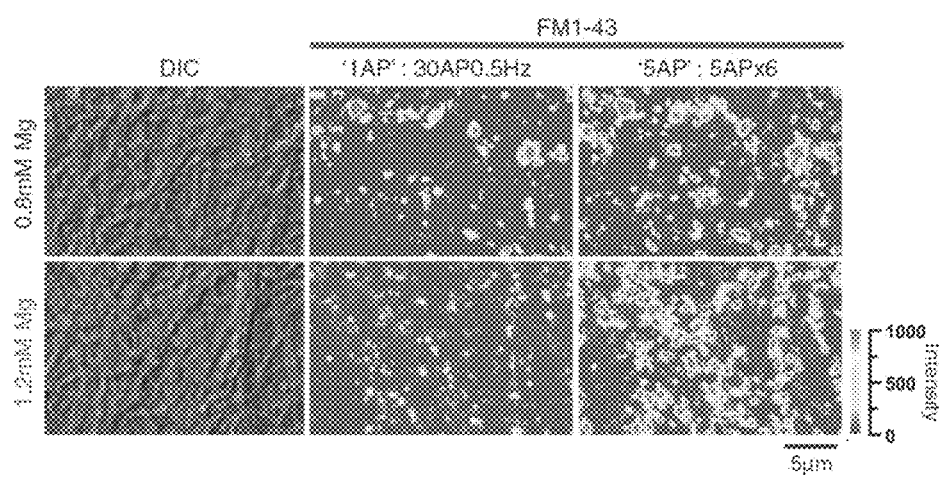
FIGS. 26A-26B are a collection of images and a graph showing input pattern-dependent reduction of Pr by elevating $[Mg^{2+}]_i$, according to embodiments of the present disclosure.
Figure 26B:
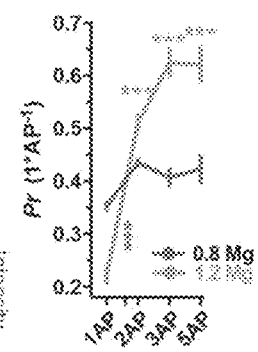

The reduction of Pr in neurons with higher $[Mg^{2+}]_i$ was completely removed in response to bursting inputs (FIGS. 26A and 26B), typically associated with functional input. Thus, inhibition of Pr by elevation of $[Mg^{2+}]_i$ was specific. As shown in FIGS. 26A and 26B, increasing $[Mg^{2+}]_i$ led to the reduction of Pr when triggered by a single action potential input (1AP). However, at bursting input pattern (i.e., >1AP) increasing $[Mg^{2+}]_i$ resulted in greater Pr. 1AP is typically associated with spontaneous background activity, while bursting input pattern is typically associated with physiological functional input. This feature helped prevent sustained background neural activity, but maintained transmission associated with physiological function.

FIGS. 26A and 26B. (FIG. 26A) Representative DIC and FM1-43 images comparing presynaptic responses to single ("1AP": 30AP0.5 Hz) and bursting ("5AP": 6 groups of 5 APs at 100 Hz, ISI 10 sec) stimulus at low (0.8 mM) and high (1.2 mM) $[Mg^{2+}]_o$. (FIG. 26B) Quantitative analysis of images from FIG. 26A. ***p<0.001. For methods see Slutsky et al, 2004, and Example 1. 2AP and 3AP refer to 6 groups of 2 APs at 100 Hz or 3 APs at 100 Hz, respectively.

The functional terminal density (N5AP) at a dendritic branch was defined as the number of 5AP bursting stimulation induced FM(+) puncta (#FM5AP) per unit area of dendritic branch (A), N5AP=#FM5AP/A. Retrograde immunofluorescence (IF) staining of MAP2, which specifically presents in dendritic skeleton, was used to label dendritic area and A was calculated from MAP2(+) area. The average N5AP of an area of interest (AOI) was calculated from the total number of FM(+) puncta divided by total MAP2(+) area to reduce the sampling error. Then, the mean N5AP of all AOIs (1-5 AOIs/coverslip) was used to represent the average N5AP in a coverslip.

Example 3: Efficacy and Safety of MMFS-01, an Intracellular Magnesium Concentration ([Mg2+]$_i$)-Elevating Agent, for Treating Cognitive Impairment in Elderly: A Randomized, Double-Blind, Placebo-Controlled Trial Materials and Methods
Study Design This was a 12-week parallel-designed, randomized, single-site, double-blind, placebo-controlled clinical trial that compared MMFS-01 and placebo. MMFS-01 is a compound containing L-threonic acid magnesium salt (L-TAMS), trademarked under the name ClariMem®.
Participants Subjects were elderly men or women between 50 and 70 years of age with self-reported complaints of their cognition (memory and concentration), and with anxiety and sleep disorder. Subjects had a Mini-Mental State Examination score (MMSE) equal to or greater than 24. Sleep difficulties defined by a score of greater than 5 on the Pittsburgh Sleep Quality Index (PSQI), and the presence of mild-to-moderate anxiety, with scores ≥12 and ≤28 on the Hamilton Anxiety Questionnaire sub-score A (HAM-A), were required for inclusion in the study.
Exclusion criteria included active heart disease; uncontrolled high blood pressure (≥140/90 mmHg); renal or hepatic impairment/disease; Type I or II diabetes; bipolar disorder; Parkinson's disease; Alzheimer's disease; dementia; unstable thyroid disease; diagnosed major affective disorder; psychiatric disorder (hospitalized in the past year); immune disorder (such as HIV/AIDS); a history of cancer (except localized skin cancer without metastases or in situ cervical cancer) within 5 years prior to screening; current use of calcium channel blockers, SSRI's or anxiolytics other than benzodiazepines as needed, with "as needed" defined as less than 5 times per month; current use of any medications that are known to interact with magnesium including loop, thiazide, potassium-sparing diuretics, muscle relaxants, penicillamine, corticosteroids, intracellular magnesium-elevating antacids or other magnesium containing products; use less than 7 days before the randomization visit of calcium channel blockers, any anxiolytics or SSRIs; current use of antibiotics (a washout period of 2 weeks was allowed); presence of an unstable dose of medication (defined as fewer than 90 days at the same dose); presence of an allergy or sensitivity to any ingredient in the test product; hepatic or renal dysfunction as evidenced by ALT, AST, AP being ≥2 times the upper limit of normal or serum creatinine value ≥2.0 mg/; history of drug or alcohol abuse in the past 12 months or had begun/stopped smoking ≤6 months ago or had plans to begin/quit smoking; possibility that the subject may become pregnant as shown by lack of birth control use, pre-menopausal status or absence of hysterectomy; status of pregnancy, lactation or plans to become pregnant during the study period; participation in another research study either presently or within 30 days prior to the screening visit; any condition, abnormality, medication usage or clinically significant clinical laboratory findings that, in the opinion of the investigator, would compromise the safety of the subject or the quality of the study data. Subjects were allowed to take medications if the medication was not part of the exclusion criteria and the dose was unchanged at least 90 days before screening and throughout the study.

Subjects stopped taking any dietary supplements at least 7 days prior to randomization, and maintained cessation during the study. They refrained from alcohol consumption or exercise for at least 24 hours prior to each test visit. No changes to the methods, including eligibility requirements and dosing, were made after commencement of the trial.

Recruitment and Randomization

Subject randomization began in November 2012, and recruitment was completed in June 2013. A total of 51 subjects (age 50-70) were recruited by Miami Research Associates (MRA) and enrolled in a randomized double-blind, placebo-controlled trial conducted at MRA (Miami). Data for all subjects at every time point were collected by MRA at their Miami clinical laboratory.

Subjects were recruited by MRA at their Miami location. Before the study began, the protocol, informed-consent form, and other information provided to subjects and caregivers were reviewed and approved by the Aspire IRB (Sep. 20, 2012). Subjects were randomly assigned to the MMFS-01 or placebo group in a ratio of 1:1, using a block-2 randomization schedule. Subjects received a sequential number corresponding to the order in which they entered the study. Study sponsors, investigators, research coordinators, attending care teams, and subjects were blinded to treatment group. The consulting statistician locked the database of data elements and unblinded it by accessing the table of randomized assignments and merging them into the data tables.

Dosage

Dosage was set to correspond to approximately 25 mg/kg/day. To accomplish this, subjects between 50 and 70 kg took 1.5 g/day, and subjects between 70 and 100 kg took 2 g/day of MMFS-01. At conclusion of the study, 8 subjects (35 percent) were taking 1.5 g of MMFS-01 per day, and 15 subjects (65 percent) were taking 2 g of MMFS-01 per day.

Power Analysis

Enrollment for this study was targeted at 50 subjects (25 per group). These subject's subjective feeling was a significant improvement in anxiety, sleep, and mental clarity. They had significant improvement in anxiety based on the HAM-A questionnaire. Therefore, the analysis was powered in this trial by reduction of HAM-A score. It was predicted the treatment would lead to a 50% reduction in HAM-A score, with a SD of HAM-A scores of approximately ±10 score points. Assuming a serial coefficient correlation of about 0.5 for HAM-A scores at baseline and 12 weeks, the within-group SD of the 12-week changes would also be ±10 score points. With the use of an unpaired Student t-test with a significance level of 0.05, a total enrollment of 50 subjects (40 completers if 20% attrition) was required for the study to be able to detect differences of about a 45% reduction in HAM-A score. An attrition rate of 20% in line with previous experience by the contract research organization who ran the study, MRA, was assumed. Even if the attrition rate had been as high as 32%, there would have been enough analyzable subjects (34 subjects) to provide 87% power in detecting a clinically meaningful 50% HAM-A score reduction.

Efficacy Endpoints

Efficacy assessments were made at Baseline Visit, Week 6 Visit and Week 12 Visit. The change in the body's magnesium status was quantified by assessing blood magnesium concentration (plasma $Mg^{2+}$), urine magnesium concentration normalized by the estimated glomerular filtration rate ($uMg^{2+}$/GFR), and intracellular magnesium concentration (Red Blood Cell; RBC $Mg^{2+}$). The key functional efficacy outcome measures included measurements of cognitive abilities, sleep quality and affect.

TMT-B Test

The Trail Making Test-Part B (TMT-B) assesses executive function as well as impulsivity, visual search, visual attention and motor speed. In the test, subjects were required to connect a series of label circles that constituted a trail. Scores were calculated as the inverse of the time (in milliseconds) it took the subject to complete the task (all 25 circle connections), representing speed. Scores from subjects unable to complete the task in the maximum allotted time (360 seconds), or from those who quit prior to the maximum allotted time, were scaled to the time to complete 25 circle connections before converting to speed. Six out of 44 (13%) subjects did not complete the task at least once with a total of 9 occurrences, 5 at baseline, 3 at Week 6, and 1 at Week 12. Higher speeds reflected better performance.

DigitSpan Test

The DigitSpan test assesses working memory performance. Scores were based on the length of the longest sequence of digits (consecutive numbers) subjects could remember and thus ranged from 0 without an upper bound, with higher scores reflecting better performance.

Eriksen Flanker Congruent/Incongruent Test

The Eriksen Flanker Congruent/Incongruent test assesses attention, that is, cognitive processes involved in detection and recognition of targets in the presence of distracting information. A target directional arrow was flanked by either arrows in the same (congruent) or opposite direction (incongruent). The average time to correctly select the target arrow's direction was recorded. The incongruent task was more difficult than the congruent task because the congruent task did not require attention or response inhibition and wasn't confounded by training effects. Therefore, the response times in the congruent condition were subtracted from that in the incongruent condition to remove training effects and discern effects on attention. The opposite of this difference was reported so higher scores reflected better performance.

Face-Name Association Test

Finally, the Face-Name Association test assesses hippocampal-dependent episodic memory. Twenty faces with twenty fictional popular first names were shown on screen. Subjects were then asked to remember and later recognize each face and name pair when presented with the same or novel face and name pairs. Using signal detection theory, the hit rate, false alarm rate, and sensitivity index (d') were calculated, where $d'=z_{(hit\ rate)}-z_{(false\ alarm\ rate)}$. d' showed how well the subject distinguished old from new. Hit rate was defined as a correct identification of an old face and name pair and false alarm as an incorrect identification of a new face and name pair. Higher scores reflected improved performance with scores above three indicative of a near perfect score.

Composite Score

Scores from several cognitive tests, evaluating four domains of cognition—executive function, working memory, attention, and episodic memory—were combined to produce a composite score to assess overall cognitive ability. The cognitive tests included TMT-B for executive function, DigitSpan for working memory capacity, Face-Name Association for short episodic memory, and Eriksen Congruent/Incongruent Flanker for attention.

The composite score was calculated as the average of the four individual z scores ($\bar{z}$). z scores were calculated for each subject on each test using the formula $$z = \frac{x - \mu_b}{\sigma_b},$$

where $\mu_b$ is the mean of all subjects (MMFS-01 and placebo combined) at baseline and $\sigma_b$ is the standard deviation (SD) of all subjects at baseline. Baseline means and SDs were used to convert the raw scores of Week 6 and Week 12 to z scores in order to determine the treatment effects (change from baseline) of MMFS-01 versus placebo for each subject for each test.

Effect size (Cohen's d) was determined for each of the cognitive endpoints at Week 6 and Week 12 using the formula Cohen's $$d = \frac{(\overline{X}_{n,\Delta MMFS-01}) - (\overline{X}_{n,\Delta Placebo})}{\sigma_{pooled}},$$

where $\overline{X}_n$ was the mean of the change from baseline values in the MMFS-01 or placebo group at either Week 6 or Week 12 and $\sigma_{pooled}$ was the pooled SD of the change from baseline of the MMFS-01 and placebo groups at either Week 6 or Week 12. Pooled SD was calculated using the formula $$\sigma_{pooled} = \sqrt{\frac{[(n_{MMFS-01} - 1)(\sigma_{\Delta MMFS-01})^2 + (n_{Placebo} - 1)(\sigma_{\Delta Placebo})^2]}{[(n_{MMFS-01} + n_{Placebo}) - 2]}}.$$

Sleep

Sleep quality was measured with the Pittsburgh Sleep Quality Index (PSQI). PSQI is a self-rated questionnaire which assesses sleep quality and disturbances over a 1-month time interval. Higher scores indicated worse sleep quality. Based on previous research, a global PSQI score greater than 5 yields a diagnostic sensitivity of 89.6% and specificity of 86.5% (kappa=0.75, p less than 0.001) in distinguishing good and poor sleepers.

Emotion

Affective personality was assessed with the HAM-A and the Positive and Negative Affect Schedule (PANAS). The HAM-A is a rating scale used in both clinical and research settings to measure the severity of psychic and somatic anxiety symptoms. It did not provide any standardized probe questions and was administered by a clinician (subject did not complete the questionnaire by his/herself). Scores ranged from 0 to 56 where ≤17 indicated mild severity, 18 to 24 mild to moderate severity, 25 to 30 moderate to severe severity, and >30 severe severity. The PANAS is a self-rated tool used to measure positive and negative affect over a 1-week time interval, and consists of two 10-item scales, one for Positive Affect and the other for Negative Affect. Subjects were asked to rate different feelings and emotions using the following Likert scale: 1=very slightly or not at all, 2=a little, 3=moderately, 4=quite a bit and 5=extremely. Scores for each scale ranged from 10 to 50. Higher positive affect scores represented more positive affect, and thus, better outcomes. Higher negative affect scores represented more negative affect, and thus, worse outcomes.

Cognitive Ability Fluctuation Analysis

The fluctuation of cognitive ability over time was evaluated by calculating variance of the change in composite score from Week 6 to Week 12 of individual subjects, with the formula $$\sigma^2 = \frac{\Sigma(X_{Week\ 12} - X_{Week\ 6})^2}{n - 1}.$$

The fluctuations of cognition of the placebo group and the MMFS-01 group were calculated separately.

Red Blood Cell Intracellular Magnesium Measurements

Total intracellular magnesium concentration in RBCs was determined using atomic absorption spectrometry (AAS). Briefly, the AAS method included the centrifugation, isolation, lysing, and dilution with an acidic solution of RBCs, followed by analysis on an atomic absorption spectrophotometer.

Tolerability and Safety

Safety evaluations included recording all adverse events, results of laboratory tests (comprehensive metabolic panel, uric acid, and complete blood count with differential), vital signs, body weight and subjective remarks.

Adverse events were listed, MedDRA encoded, grouped by general type of event (gastrointestinal, neurologic, cardiac, etc.), and cross-tabulated by event type and product group. The principal investigator catalogued adverse events as mild, moderate, or severe according to the following definitions: Mild (causing no limitation in normal activities), Moderate (causing some limitation in normal activities) and Severe (causing significant limitation in or the inability to perform normal activities). A central laboratory conducted all laboratory evaluations. Of these 47 events, 13 events, occurring in 10 subjects, were judged by the principal investigator to be probably related or possibly related to study product. Probably and possibly-related adverse events were considerably more prevalent in the placebo group than in the MMFS-01 group (9 and 4 events, in 6 and 4 subjects, respectively). The predominant adverse events were related to gastrointestinal function (affecting 5 of 25 subjects (20.0%) in the MMFS-01 group and 4 of 26 subjects (15.4%) in placebo group, p=0.726) or infections/infestations (affecting 4 of 25 subjects (16%) in the MMFS-01 group and 6 of 26 subjects (23%) in placebo group, p=0.726).

Statistical Analysis

The safety population consisted of subjects who received at least one dose of any study product, and who had any subsequent encounter with the study site. The efficacy population included all subjects who completed all scheduled visits, had no protocol deviations that in the judgment of the principal investigator would have invalidated their efficacy data (see product compliance section below). Only data from subjects that completed all visits were included in the statistical analysis; therefore, there were no missing data values in the dataset, and imputation was not required.

Statistical analyses for cognitive tests and body magnesium status variables were performed with SPSS and R. For categorical variables, difference in the distribution of categories between the different treatment groups was tested for nominal significance by the Chi-Square test, in SPSS or GraphPad Prism™. Formal statistical tests were performed for cognitive endpoints and magnesium status using a univariate analysis of covariance (ANCOVA) model at Week 6 and Week 12 with baseline values as a covariate. For safety endpoints, changes were tested for significance by the paired Student t-test, or the non-parametric Wilcoxon signed-ranks test if necessary. Differences in adverse event patterns between product groups were tested by the Fisher Exact test.

Longitudinal repeated measures ANCOVA analyses using observed data without any data imputation were used to determine the overall effect from baseline of MMFS-01 compared to placebo. The model included the categorical fixed effects of treatment (MMFS-01 versus placebo), week (6 and 12), and treatment-by-week interaction, as well as the continuous fixed covariate of baseline measurement. Normality of distribution and equality of variance were determined using the Shapiro-Wilk's test and Levene's test, respectively. For endpoint values that violated either test, additional bootstrapping was employed, using resampling methods. In the ANCOVA analyses, in order to simulate the F-distribution under the null hypothesis, resampling techniques were used to permute the treatment labels, time point labels, and baseline values. For each of the 10,000 random permutations, F-statistics for the ANCOVA model were computed, and used to compute a percentile p-value for the dataset. Bootstrapping was used for TMT-B, $Mg^{2+}$ Urine, and $Mg^{2+}$ Plasma. In one exception, to determine treatment differences at Week 6 and Week 12 between the MMFS-01 and placebo groups for percent change in RBC magnesium concentration, an analysis of variance (ANOVA) model was used instead of ANCOVA As this was not a pivotal Phase-III clinical trial, it was not required to control the study-wise Type-1 error rate to a specified alpha level. Each efficacy endpoint was considered an independent question of interest, with a hypothesized difference, and was tested independently using a two-tailed 0.05 alpha level ($p \leq 0.05$ required for a conclusion of statistical significance). No interim analysis was performed for this study.

To determine outliers, individual data for each test was analyzed. If a baseline score was greater than 2 SDs away from the mean then that data point was considered to be an outlier, and therefore excluded. Of the four cognitive tests, outliers were only found on the Flanker test. Out of 44 baseline data points, 3 were removed (1 MMFS-01, 2 placebo) from the analysis of the Flanker test. Additionally, some ceiling effects were found in the Face-Name test, in which some subjects had a near perfect baseline score (>3). Therefore, the threshold for the ceiling baseline Face-Name score was set as 3. Out of 44 data points, 3 subjects were removed (2 MMFS-01, 1 Placebo) from the analysis of the Face-Name test. The contribution of any excluded subject to the composite score was removed so the excluded data points did not erroneously skew the composite score. Except for outliers and scores at the ceiling, all data were included for all subjects for all outcome measurement analyses.

Product Compliance

Compliance was measured via the pill counting method, by documenting the number of calendar days between visits and the number of pills that should have been taken. Subject compliance was recorded as a percent of the prescribed amount for each visit and then averaged to produce an overall compliance figure. Per the original protocol, 80-120% compliance was considered acceptable. Of 44 subjects in the per protocol population, 41 returned their unused pills and were in the acceptable range. The remaining 3 did not return their pills, but were determined to be within the acceptable range of compliance based on the estimation of the PI, using MRA staff's familiarity with the subject and/or subject's compliance during other testing phase(s) of the study to make this decision. Therefore, all 44 subjects were considered compliant.

Results

Study Population

The mean subject age was 57.3±5.2 years, with 71% female. Baseline demographic and background characteristics are summarized in Table 1 (shown in FIG. 11); there were no significant differences in these characteristics between the treatment and control groups. 66.7% of the subjects (34 of 51) had coexisting medical conditions at baseline. The most common conditions were gastrointestinal (10 subjects; 19.6%). None of the subjects were taking CNS medications and there were no significant differences between groups in the presence of coexisting diseases or medication use.

Figure 14:
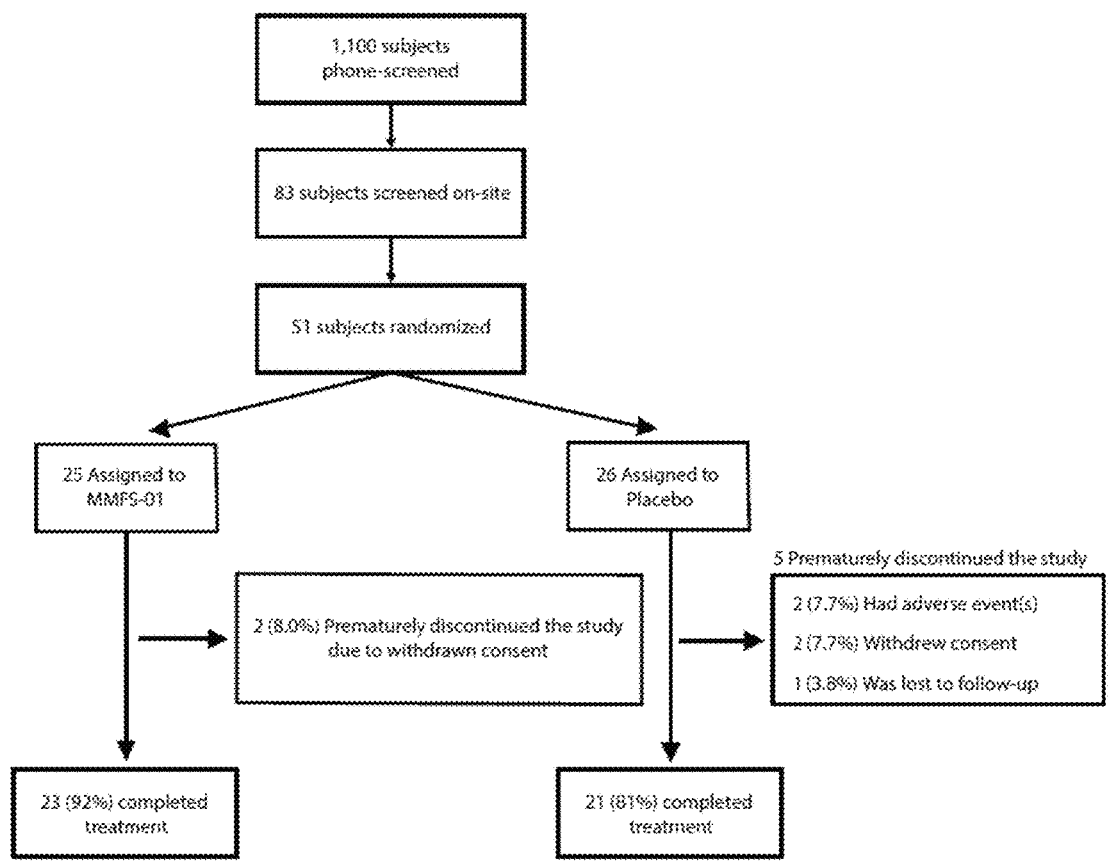
FIG. 14 is a schematic diagram of the study assignment and outcomes, according to embodiments of the present disclosure.

25 subjects received MMFS-01 (Neurocentria, Inc., Fremont, Calif., USA), and 26 received placebo. 7 subjects (14%) discontinued the study prematurely: 2 (7.7%) in the MMFS-01 group and 5 (19%) in the placebo group (FIG. 14). Withdrawn consent was the primary reason for discontinuation. The remaining 44 subjects completed the study and were included in the efficacy analysis.

FIG. 14. Study Assignment and Outcomes. All subjects who withdrew were evaluated for the presence of an adverse event. If an adverse event was determined as the reason for withdrawn consent then "had adverse event(s)" was listed as the reason for premature discontinuation.

Efficacy

The Effects of MMFS-01 on Body Magnesium Levels

The change in body magnesium status was determined by quantifying magnesium in urine (excretion), plasma (extracellular), and RBC (intracellular). Excreted magnesium was measured to estimate the relative amount of absorbed magnesium, because magnesium excreted in urine is proportional to absorbed magnesium, provided that the subject has normal kidney function for mineral reabsorption (i.e., the higher the absorption of magnesium, the higher the excretion). Treatment with MMFS-01 for 12 weeks resulted in a significant increase in the excretion rate of magnesium relative to placebo (p=0.027). Plasma magnesium concentration is tightly controlled by homeostatic mechanisms, and plasma magnesium concentration is hardly changed by conventional oral magnesium supplementation. While magnesium was initially higher in the plasma of subjects taking MMFS-01 (Week 6) versus placebo, there was no difference between the two groups at Week 12, due to a change in plasma magnesium concentration in the placebo group from Week 6 to Week 12. This difference is indicated by a significant treatment×time interaction between MMFS-01 and placebo (p<0.05). Finally, RBC magnesium concentration increased in MMFS-01 treated subjects from baseline to Week 12 (3.3±1.9%) and from Week 6 to Week 12 (3.0±2.0%) compared with a reduction in placebo treated subjects at Week 12 (−0.6%±1.8%) and from Week 6 to Week 12 (−3.6±2.1%, p=0.019). The body magnesium results are summarized in Table 2 (provided in FIG. 12A). These results suggest that the dosage of MMFS-01 was effective at loading magnesium into the body.

The Effects of MMFS-01 on Cognitive Abilities

The effect of MMFS-01 on cognitive ability was evaluated in four cognitive domains: executive function, working memory, attention, and short-term episodic memory by administration of the Trail Making, DigitSpan, Flanker, and Face-Name tests, respectively, at Baseline, Week 6, and Week 12 (Table 3, provided in FIG. 12B). These cognitive tests were chosen based on the current consensus that multiple domains of cognition should be evaluated to determine cognitive impairment. The selected cognitive domains were similar to those included in the Alzheimer's Disease Cooperative Study—Preclinical Alzheimer Cognitive Composite (ADCS-PACC), are in line with recent recommendations by the U.S. Food and Drug Administration, and are reliable for testing cognitive deficits and improvements.

Figure 15A:
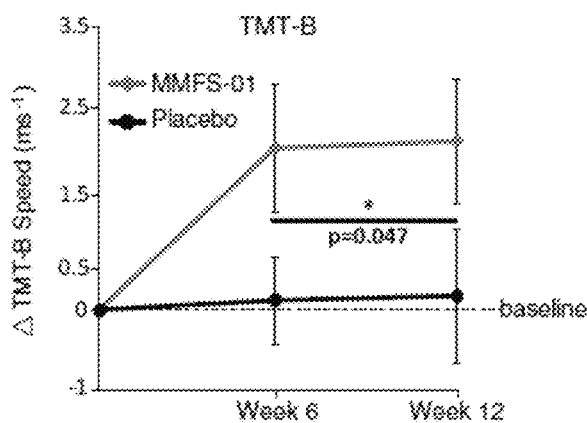
FIGS. 15A-15E are a collection of graphs showing measurements of cognitive endpoints for MMFS-01 and placebo.
Figure 15B:
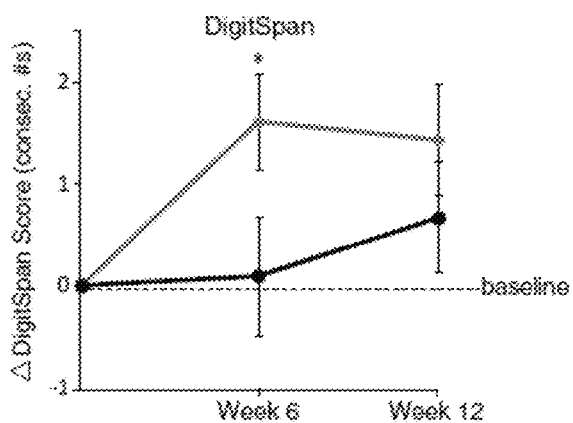
Figure 15C:
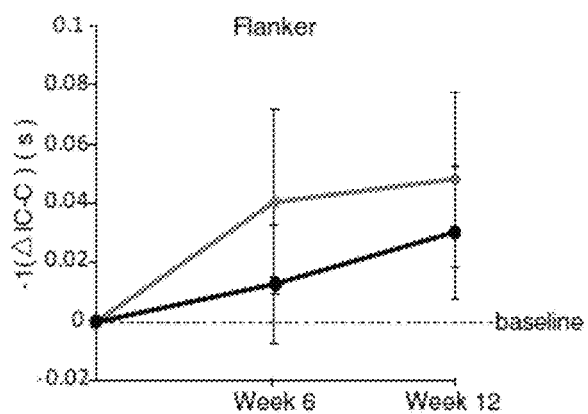
Figure 15D:
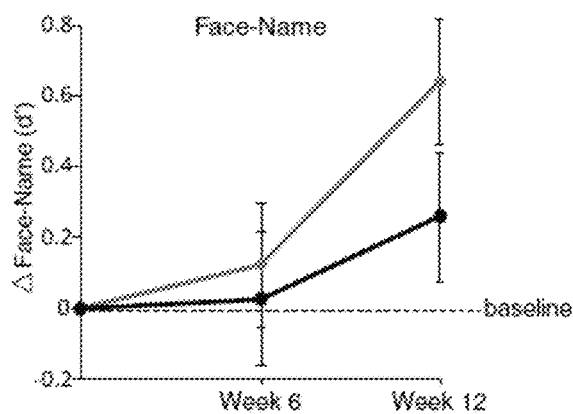
Figure 15E:
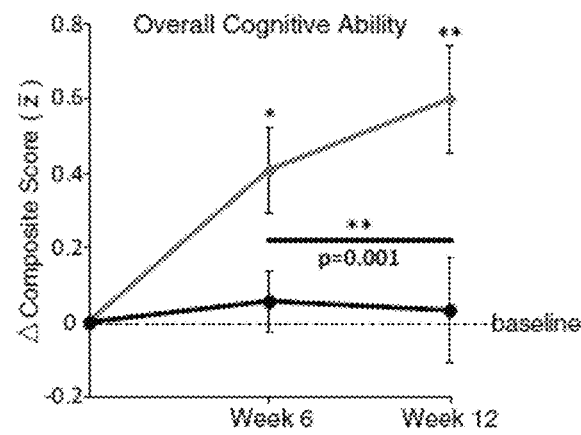

FIGS. 15A-15E. Cognitive Endpoints for MMFS-01 and Placebo. Change from baseline (dashed line) was evaluated at Week 6 and Week 12 for MMFS-01 (red line) and placebo (black line) treated groups in four cognitive tests: TMT-B (FIG. 15A), DigitSpan (FIG. 15B), Flanker (FIG. 15C), and Face-Name (FIG. 15D). TMT-B is presented as speed to complete 25 circle connections in milliseconds, DigitSpan as the number of consecutive numbers (consec. #s) repeated without error, Flanker as the opposite of the difference between Congruent time and Incongruent time −1(IC−C) in seconds, and Face-Name as relative d' score. The opposite of change in IC-C is shown to illustrate positive change for improvement in the task. Overall cognitive ability (composite score) is the average of the z scores ($\bar{z}$) of the four cognitive tests, presented as the change in composite score from baseline (FIG. 15E). Asterisk over individual time points denotes significance between MMFS-01 and placebo only at that time point whereas asterisk over line between Week 6 and Week 12 denotes a significant overall treatment effect. *p<0.05, **p<0.01. All values are mean±SEM.

MMFS-01 treatment resulted in a significant overall treatment effect in TMT-B (p=0.047; Table 3, provided in FIG. 12B; and FIG. 15A). Performance speed in TMT-B (FIG. 15A), reflecting executive function and cognitive processing, improved from baseline at Week 6. The mean improvement (MI) was 2.0±0.8 ms$^{-1}$ at Week 6 and 2.1±0.8 ms$^{-1}$ at Week 12 in the MMFS-01 group, corresponding to improvements of 19.1% (Week 6) and 19.9% (Week 12). There was little improvement from baseline in the placebo group at Week 6 (MI=0.1±0.5 ms$^{-1}$) and Week 12 (MI=0.2±0.8 ms$^{-1}$). These results correspond to an effect size (Cohen's d) of 0.58 at Week 6 and 0.51 at Week 12 (Table 3, provided in FIG. 12B).

The DigitSpan test assesses working memory capacity. Subjects receiving MMFS-01 improved their DigitSpan scores (Table 3, provided in FIG. 12B; and FIG. 15B) at Week 6 (MI=1.61±0.48 consecutive numbers) compared to those receiving placebo (MI=0.10±0.59 consecutive numbers). This difference was significant (p=0.023, Cohen's d=0.61), representing a 13.1% net improvement. At Week 12, the improvement persisted in the MMFS-01 group (MI=1.43±0.55 consecutive numbers), but there was an increase of the test scores in the placebo group (MI=0.67±0.54 consecutive numbers). Therefore, the difference between the MMFS-01 and placebo groups was not significantly different at Week 12 (p=0.225).

The Flanker test (Table 3, provided in FIG. 12B, and FIG. 15C) was used to evaluate attention capability. The opposite of the difference between incongruent and congruent test times was used to represent the test score (see "Materials and Methods", above, for explanation). Improved test scores relative to baseline was observed in the MMFS-01 group, but the improvements were not statistically different from that of the placebo group at either Week 6 or Week 12, and there was not an overall treatment effect. Flanker test time improved by 34.9% (Week 6) and 38.2% (Week 12) in subjects receiving MMFS-01; however, times of subjects receiving placebo also improved at Week 6 (14.3%) and Week 12 (32.3%). These results suggest that there were significant training effects in this test, which reduced the test's utility for evaluating efficacy of treatment.

The Face-Name association test was used to evaluate episodic memory (Table 3, provided in FIG. 12B, and FIG. 15D). In subjects receiving MMFS-01, test scores did not significantly change from baseline at Week 6 (7.1%, p=0.460), but improved significantly from baseline at Week 12 (37.6%, p=0.003). However, similarly, the test scores in the placebo group did not improve at Week 6, but increased from baseline by 16.2% at Week 12, although not significantly (p=0.207). Despite a 21.4% net improvement at Week 12 with MMFS-01 treatment, improvement in the MMFS-01 group was not significantly better than improvement in the placebo group (p=0.089, Cohen's d=0.44).

Finally, to evaluate the overall cognitive ability of each subject, the composite score of all subjects at baseline was calculated for Week 6 and Week 12. Each individual score from each cognitive test was converted to a z score and the z scores from the four tests were averaged (z) to obtain the composite score for each subject. The selected cognitive tests evaluated major domains of overall cognitive ability (Table 3, provided in FIG. 12B; and FIG. 15E). The composite score $\bar{z}$ of subjects treated with MMFS-01 improved significantly compared to placebo at Week 6 (p=0.017) and Week 12 (p=0.003), and had a significant overall treatment effect (p=0.001). Subjects treated with MMFS-01 had a MI of 0.41±0.12 $\bar{z}$ at Week 6 and 0.60±0.13 $\bar{z}$ at Week 12 compared to 0.06±0.08 $\bar{z}$ at Week 6 and 0.03±0.14 $\bar{z}$ at Week 12 for subjects treated with placebo. The effect size was 0.74 at Week 6 and 0.91 at Week 12. Based on the typical scale for effect size where 0.2-0.5 is small, 0.5-0.8 is medium, and ≥0.8 is large, the improvement of overall cognitive ability induced by MMFS-01 treatment was robust.

Figure 19A:
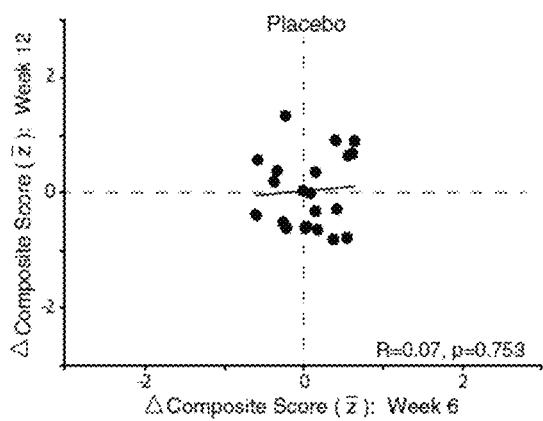
FIGS. 19A and 19B are a collection of graphs showing correlation of change in overall cognitive ability from baseline at Week 6 and Week 12, according to embodiments of the present disclosure.
Figure 19B:
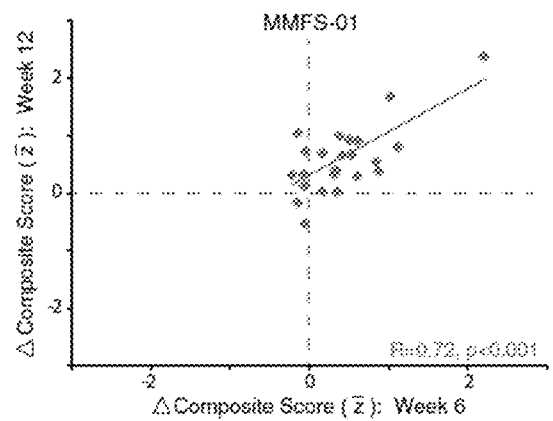

To determine if improvement in overall cognitive ability persisted from Week 6 to Week 12 in individual subjects the composite score change from baseline at Week 6 versus the change from baseline at Week 12 was plotted. The degree of improvement at Week 6 was significantly correlated with the degree of improvement from baseline at Week 12 (R=0.72, p<0.001; FIG. 19B). Conversely, in the placebo group, there was no correlation between change in composite score at Week 6 and change in composite score from baseline at Week 12 (R=0.07, p=0.753; FIG. 19A). This analysis suggests that the treatment effects of MMFS-01 persisted in individual subjects.

FIGS. 19A and 19B. Correlation of Composite Score Change from Baseline at Week 6 and Week 12. Correlations (R) were determined between the change from baseline in composite score at Week 6 and at Week 12 for placebo treated (FIG. 19A) and MMFS-01 treated (FIG. 19B) subjects.

MMFS-01 Treatment Reduces Fluctuation in Overall Cognitive Ability

Figure 16A:
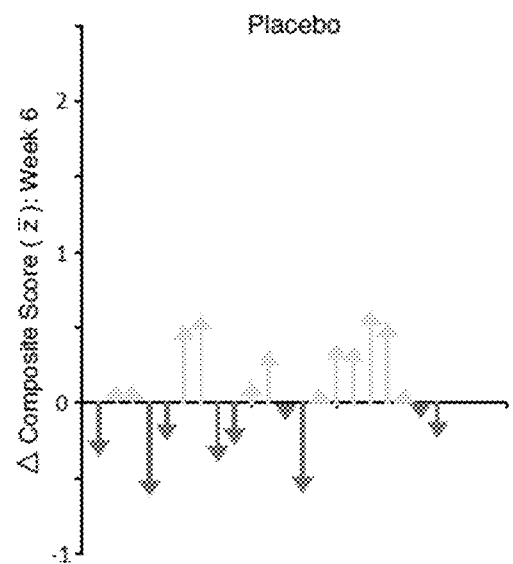
FIGS. 16A-16E are a collection of graphs showing an analysis of cognitive fluctuation with MMFS-01 treatment, according to embodiments of the present disclosure.
Figure 16B:
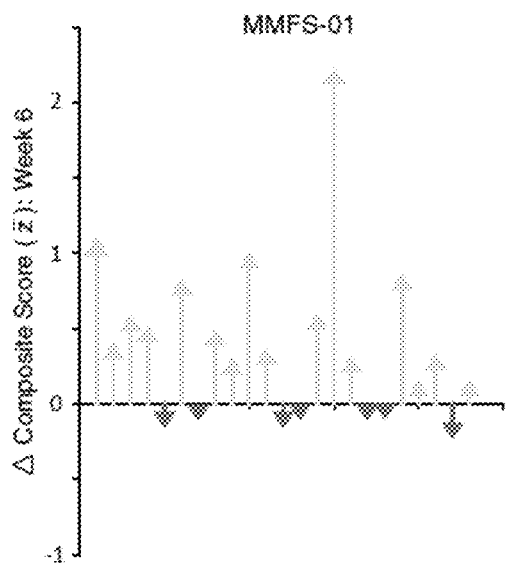
Figure 16C:
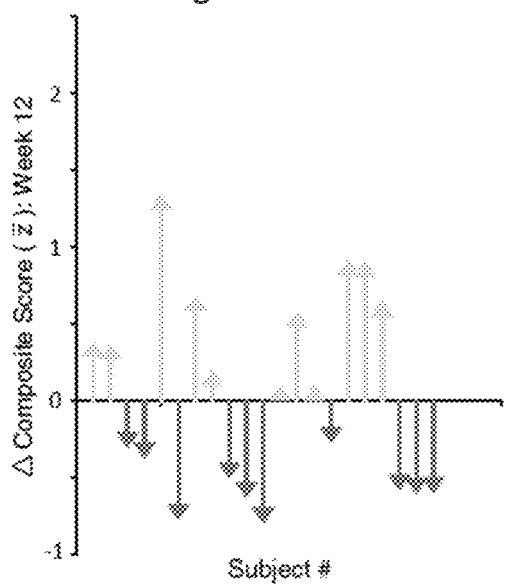
Figure 16D:
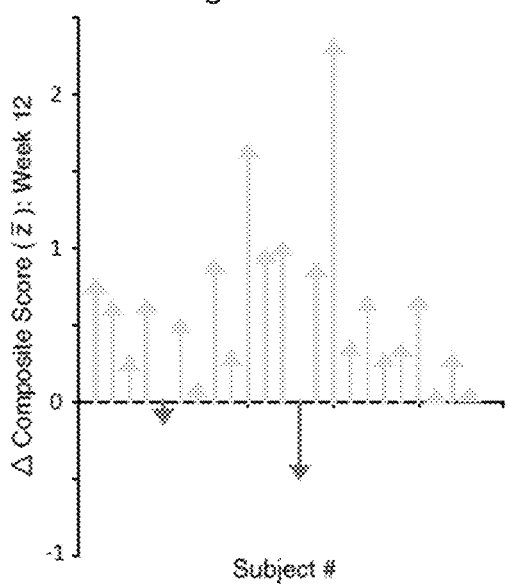

Fluctuation of cognitive ability is an early sign of cognitive impairment. It is reported that 85% of MCI patients have fluctuations over time in their cognitive ability. To evaluate if the subjects' cognitive ability fluctuated, for each subject the composite score change from baseline was plotted at Week 6 and Week 12 (FIGS. 16A-16D). In the placebo group, subjects' composite scores changed dramatically both positively and negatively from baseline (FIGS. 16A, 16C), confirming the existence of cognitive variance in subjects in the current study. Interestingly, in the MMFS-01 treated group, changes from baseline at both Week 6 and Week 12 were mostly positive (FIGS. 16B, 16D). Thus, MMFS-01 treatment appeared to reduce negative fluctuations in overall cognitive ability.

FIGS. 16A-16E. Analysis of composite score fluctuation. (FIGS. 16A-16D) Individual subject change from baseline composite score at Week 6 and Week 12. Each arrow represents an individual subject, ordered as subject number determined by the order in which each enrolled in the study. Green arrows indicate an increase from baseline in composite score and red arrows indicate a decrease from baseline in composite score. (FIG. 16E) Change in composite score from Week 6 to Week 12 for each subject. Bars indicate range of data. Only subjects in the MMFS-01 group who had a positive composite score at Week 6 were included in the "Responders only" group (far right).

Figure 16E:
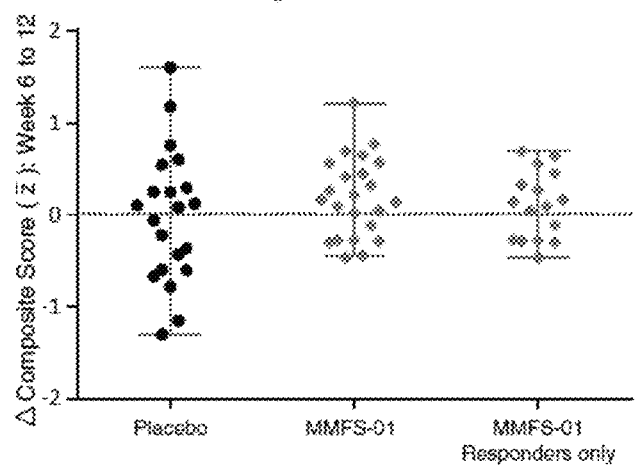

To quantify the effect of MMFS-01 on the fluctuation of cognitive ability, the variance of composite scores between MMFS-01 and placebo groups was compared (FIG. 16E). The variance of individual subjects' composite score between Week 6 and Week 12 was calculated (see "Materials and Methods", above, for equation). Change from Baseline to Week 6 was not used to avoid the pre-existing cognitive fluctuation prior to treatment. Variance of the composite scores in the placebo group was $\sigma^2=0.53$ whereas variance in MMFS-01 treated group was $\sigma^2=0.22$, a reduction of 57.6%. This analysis included all subjects, even those whose composite score did not improve at Week 6 (n=7 of 23), so any delayed improvement that occurred from Week 6 to Week 12 contributed to this variance. When only subjects whose composite score improved at Week 6 (n=16 of 23) were considered, variance was even smaller ($\sigma^2=0.14$), representing a 72.8% reduction in variance (FIG. 16E). Therefore, MMFS-01 treatment might also help reduce cognitive fluctuation.

Change in Intracellular Magnesium Predicted the Improvement of Cognitive Abilities It was noticed that the composite scores of subjects in the treatment group did not improve uniformly and in particular, four subjects had little or no improvement after 12 weeks of treatment. Pre-clinical studies indicate that the increase in intracellular magnesium concentration in neurons is related to the increase in synapse density and elevation of CSF magnesium may be an intermediary molecule in the mechanism of action through which the present compound leads to an improvement in cognitive abilities. As a surrogate marker for neuronal intracellular magenesium, intracellular magnesium of RBCs was used to provide a reference for the loading effectiveness of magnesium into cells.

Figure 17A:
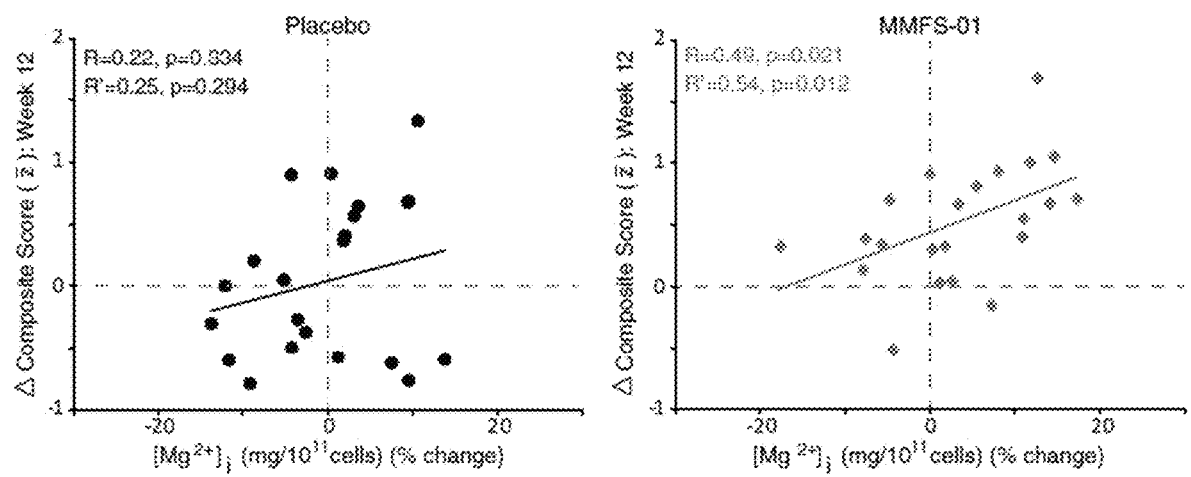
FIGS. 17A-17D are a collection of graphs showing the association of change in cognitive ability with change in intracellular RBC $Mg^{2+}$ concentration or with baseline cognitive ability, according to embodiments of the present disclosure.
Figure 17B:
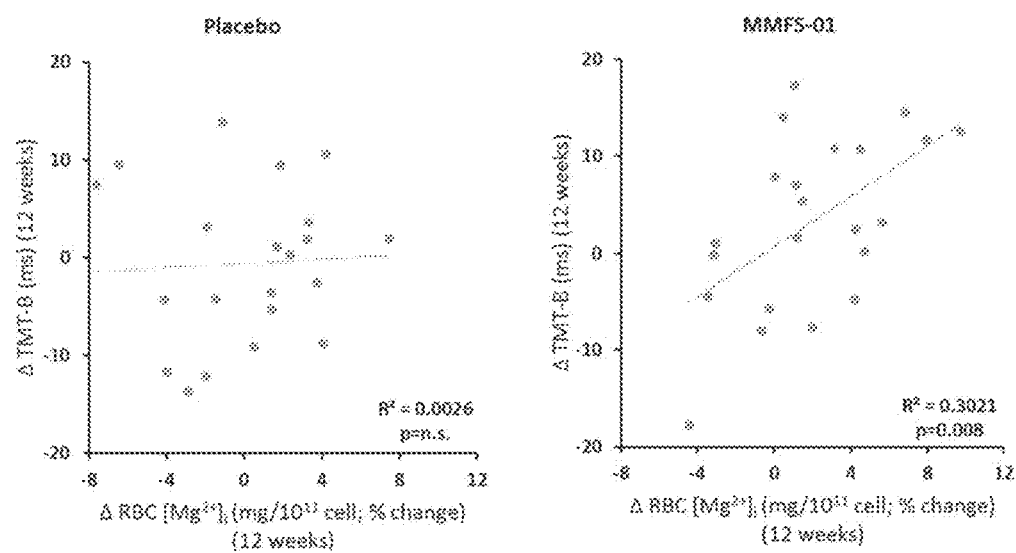

Remarkably, the percent change of RBC intracellular magnesium concentration predicted, with statistical significance, the enhancement in overall cognitive ability (composite score) in the MMFS-01 group (R=0.49; p=0.021; FIG. 17A, right panel), but not in the placebo group (R=0.22; p=0.334; FIG. 17A, left panel). The percent change of RBC intracellular magnesium concentration also predicted, with statistical significance, the improvement in performance on TMT-B in the MMFS-01 group (R=0.55; p=0.008; FIG. 17B, right panel), but not in the placebo group (R=0.05; p=0.829; FIG. 17B, left panel). Controlling for the effects of baseline composite score (see below), the correlation between the percent change of RBC intracellular magnesium concentration and the change in composite score at Week 12 further improved (denoted as R'=0.54; p=0.012; FIG. 17A, right panel), with no significant change in the placebo group (R'=0.25, p=0.294; FIG. 17A, left panel).

FIGS. 17A-17D. (FIGS. 17A-17B) Correlations (R) were determined between the percent change of RBC intracellular magnesium concentration and the change from baseline in composite score at Week 12 for placebo treated (FIG. 17A, left panel) and MMFS-01 treated (FIG. 17A, right panel) subjects or the change from baseline in TMT-B speed (milliseconds) at Week 12 for placebo treated (R=0.051 p=n.s., n=21; FIG. 17B, left panel) and MMFS-01 treated (R=0.550, p=0.008, n=22; FIG. 17B, right panel) subjects. (FIGS. 17C-17D) Correlations (R) were also determined between the baseline composite and the change from baseline in composite score at Week 12 for placebo treated (FIG. 17C) and MMFS-01 treated (FIG. 17D) subjects. To eliminate contribution to the correlation from other factors, either percent change of RBC intracellular magnesium concentration or baseline composite score was controlled for while calculating correlation with change of composite score at Week 12. These correlations (not graphed) are denoted as R'.

Figure 17C:
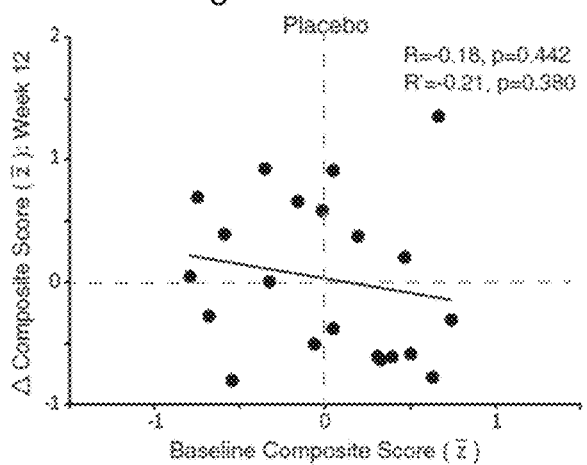
Figure 17D:
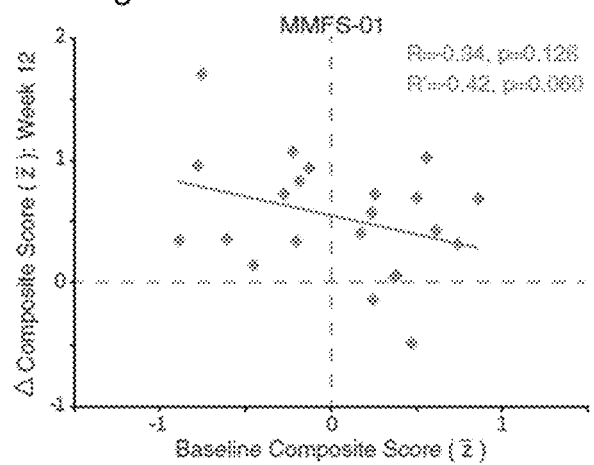

There was also a small but non-significant inverse correlation between baseline composite score and the change in composite score at Week 12 in the MMFS-01 group (R=−0.34; p=0.126; FIG. 17D), that was not present in the placebo group (R=−0.18; p=0.442; FIG. 16H). Controlling for the percent change of intracellular magnesium, the correlation between baseline composite score and change in composite improved nearly to statistical significance in the MMFS-01 group (R'=−0.42; p=0.060; FIG. 16I) but not in the placebo group (R'=−0.21; p=0.380; FIG. 17C). These data suggest that MMFS-01 might be more effective at improving the overall cognitive ability of subjects with greater cognitive deficits.

Clinical Significance of MMFS-01

Analysis of data from the cognitive tests demonstrated that the improvement of cognitive abilities by MMFS-01 treatment was statistically significant. Further analysis was carried out to determine the clinical significance of MMFS-01 treatment. One way to quantify clinical significance was to determine how much the cognitive deficit is reversed by comparing test scores with normative data of age-matched subjects. Unfortunately, normative data for the present composite score was not available. However, normative data for TMT-B was available from cognitively competent subjects from age 18 to 89 years, and performance on TMT-B declines with age (Tombaugh et al., (2004) *Archives of clinical neuropsychology: the official journal of the National Academy of Neuropsychologists* 19, 203-214; referred to hereafter as the "Tombaugh study"). Results from the present study were compared with results from the Tombaugh study. Subjects in the present study took significantly longer (125.7±17.6 s) to complete the TMT-B task than age-matched (average age 50-70 years) cognitively normal subjects in the Tombaugh study (75.0±1.3 s; p<0.0001), confirming that subjects in the present study indeed had executive function decline (FIG. 18A), and a mild cognitive impairment.

To quantify how much cognitive impairment was reversed, average speed of performance on TMT-B was plotted as a function of age. The youngest age group, age 18-24, performed the fastest, so all other age groups were normalized to the 18-24 age group. Strikingly, performance of cognitively normal subjects on the TMT-B task declined linearly with age (R=−0.99, p=$10^{-8}$), at a rate of 1.04% per year (FIG. 18B). Average TMT-B speed for all subjects in the present study was about 10% lower than age-matched controls. Following 12 weeks of MMFS-01 treatment there was an average increase of 10.3±3.8% in TMT-B speed, such that their speed was close to that of their age-matched controls.

With this data, each subject was assigned a "brain age" that corresponded to that subject's speed relative to the normative TMT-B data. The difference between each subject's actual age and brain age was representative of the degree of executive function decline. For example, a 50 year old subject who performed approximately 10% worse on the TMT-B test than a normal 50 year old had a brain age that corresponded approximately to a cognitively normal 60 year old, and therefore had a 10 year decline. The average age of all subjects who completed the current study was 57.9±0.8 years (FIG. 18B), but their average brain age at baseline was 68.3±3.0 years (FIG. 18B), suggesting that the subjects in the current study had about 10 years of cognitive impairment. After 6 weeks of treatment, the average brain age of the MMFS-01 group deceased from 69.6±4.2 years to 60.6±5.6 years, an improvement of 9.0±3.5 years (FIG. 18C, top left panel), and persisted after 12 weeks of treatment with 9.4±3.5 years of improvement (FIG. 18B; FIG. 18C, top right panel). In contrast, there was little change in the average brain age in the placebo group, improving 0.6±2.3 years at Week 6 (FIG. 18C, bottom left panel) and 0.8±3.5 years at Week 12 (FIG. 18C, bottom right panel). These data demonstrate that MMFS-01 treatment was effective in the subjects at reversing cognitive impairment almost back to normal ability relative to age.

Figure 18A:
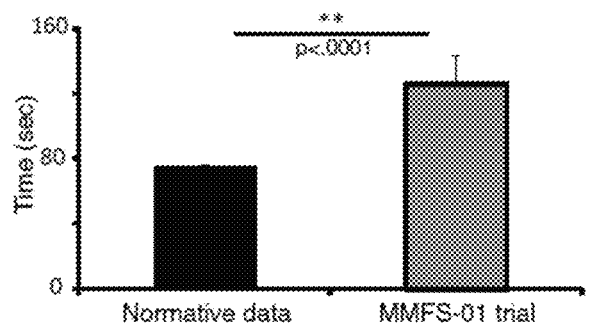
FIGS. 18A-18C are a collection of graphs showing the reversal of brain age deficits in MMFS-01 treated subjects, according to embodiments of the present disclosure.
Figure 18B:
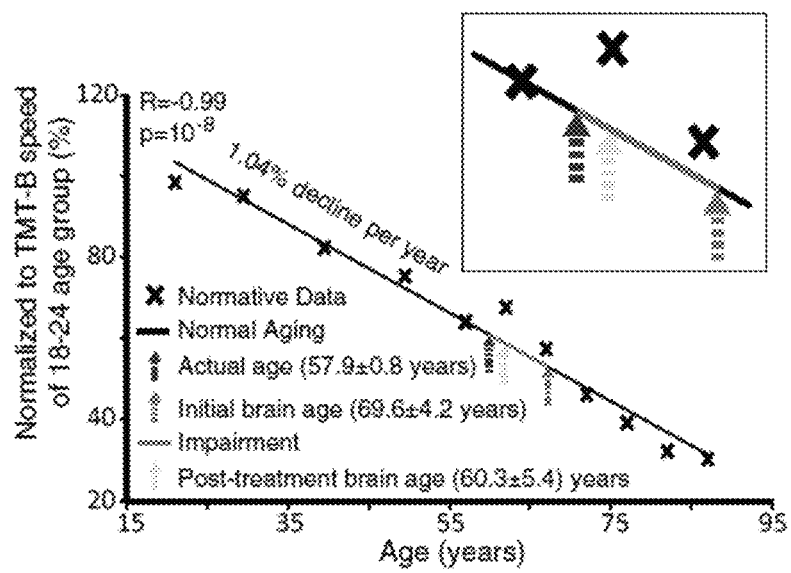
Figure 18C:
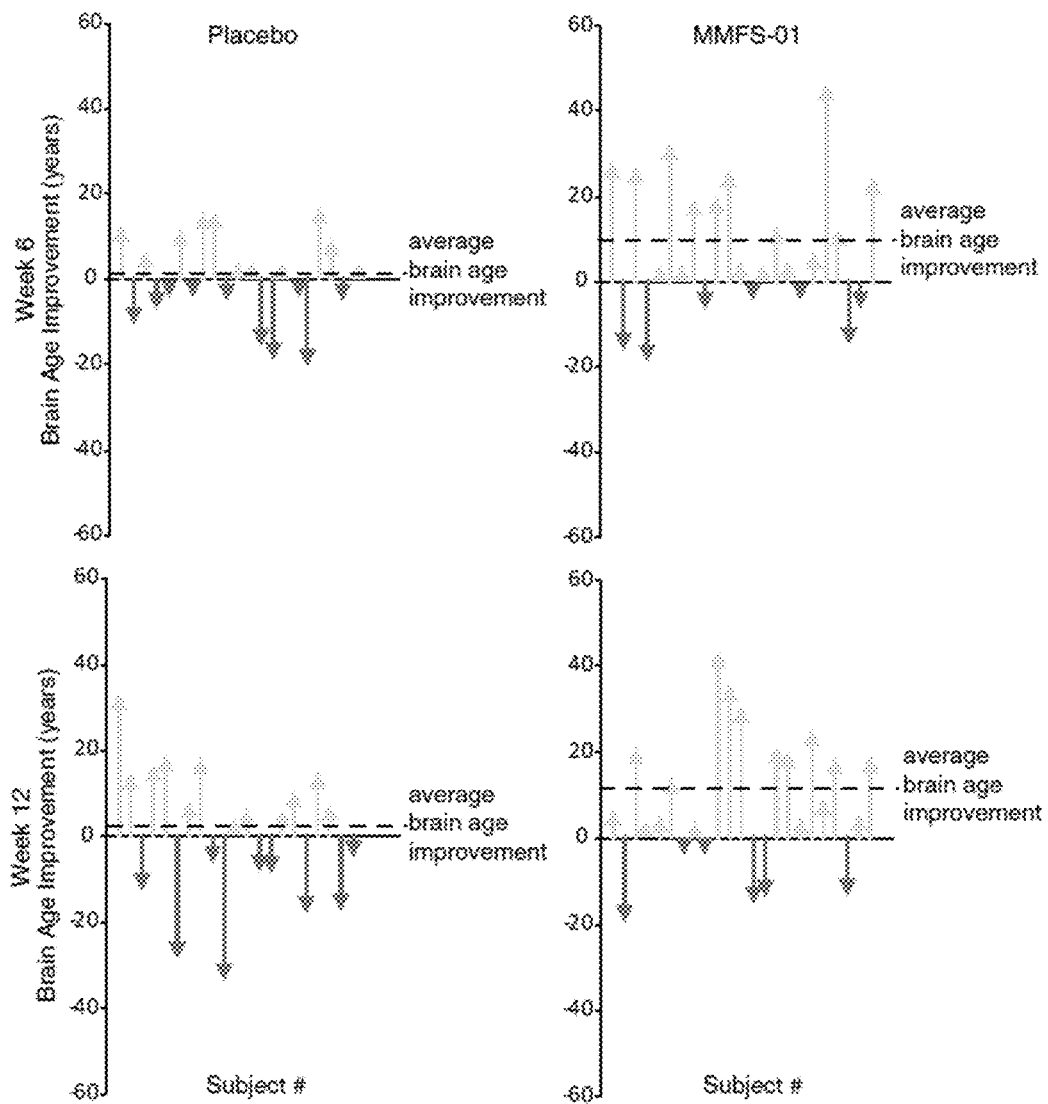

FIGS. 18A-18C. Reversal of executive function deficits in MMFS-01 treated subjects. FIG. 18A) Average TMT-B time was compared to age-matched normative data. FIG. 18B) Relationship between age and normalized TMT-B speed (percent normalized to peak speed; 100%=18-24 age group) was graphed from normative data (ages 18-89 separated in 11 different age groups). TMT-B speed declines linearly (R=−0.99, p=$10^{-8}$) at a rate of 1.04% per year. Shown on the graph are the location where TMT-B speed corresponds to the average actual age of all subjects in the study, the initial brain age of subjects in the MMFS-01 group, and the brain age of subjects following 12 weeks of MMFS-01 treatment. The average impairment in brain age of the subjects at the beginning of the trial, relative to age-matched controls from the normative data set, is depicted along the linear trendline. The area of the graph corresponding to the age range of subjects in the study (50-70 years) is enlarged in the inset. FIG. 18C) Change in brain age from baseline for each subject in the MMFS-01 group at Week 6 (top left panel) and Week 12 (top right panel) and placebo group at Week 6 (bottom left panel) and Week 12 (bottom right panel). Each arrow indicates an individual subject, ordered as subject number determined by the order in which each enrolled in the study. Arrows indicate brain age improvement and brain age decline relative to baseline. The average brain age improvement is indicated by a dashed line.

Using elevation of RBC intracellular magnesium as a biomarker to screen for responders, 15 of 22 subjects in the MMFS-01 group (68.2%) responded to MMFS-01 treatment. When the brain age of only the responders was calculated, the improvement at Week 12 was 14.6±3.9 years, indicating an even greater reduction in cognitive impairment among magnesium responders than all subjects receiving MMFS-01. On the other hand, these data also show approximately 30% of the subjects did not respond to MMFS-01 treatment.

Safety and Tolerability

Adverse Events

The safety population was composed of 25 subjects in the MMFS-01 group and 26 subjects in the placebo group. A total of 47 adverse events were observed among 28 of the 51 subjects in the safety population, experienced approximately equally among subjects in placebo and MMFS-01 groups (15 and 13 subjects, respectively; Table 5, shown in FIG. 13). Individual events were considerably more prevalent in the placebo group than in the MMFS-01 group (30 and 17 events, respectively). Most adverse events were mild, and no serious adverse events were observed during the course of the study. No significant changes in body weight, systolic blood pressure, diastolic blood pressure, or heart rate were observed. For additional tolerability and safety information see Materials and Methods section.

Figure 20:
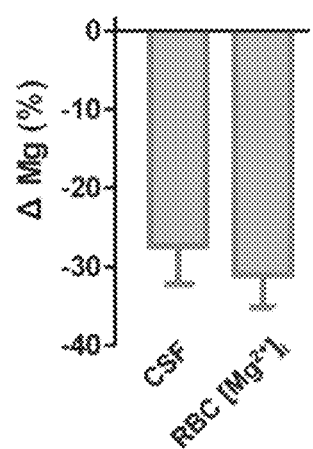
FIG. 20 is a graph showing the change in magnesium concentration upon reduction of magnesium intake, according to embodiments of the present disclosure.

Example 4: Intracellular Magnesium Concentration as a Biomarker for Improving Cognitive Ability and/or Treating a Neurological Disorder Red Blood Cell (RBC) $[Mg^{2+}]_i$ is Sensitive to Change in Magnesium Intake Using animal studies, it was found that red blood cell (RBC) $[Mg^{2+}]_i$ is sensitive to change in magnesium intake. Reduction of magnesium intake caused a significant drop in RBC $[Mg^{2+}]_i$. (FIG. 20). A similar degree of magnesium reduction was observed in cerebrospinal fluid (CSF) (FIG. 20). Thus, RBC $[Mg^{2+}]_i$ has the potential to be a biomarker for body magnesium status.

FIG. 20. 3 month old rats were given regular chow or chow with low $Mg^{2+}$ for 4 weeks. The percentage change of $Mg^{2+}$ in CSF and Red blood cells (RBC) of rats receiving low $Mg^{2+}$ chow, relative to rats receiving regular chow, is shown. n=10 for each group, p<0.001.

Correlation Between RBC Ionized $[Mg^{2+}]_i$ and Memory

Figure 21:
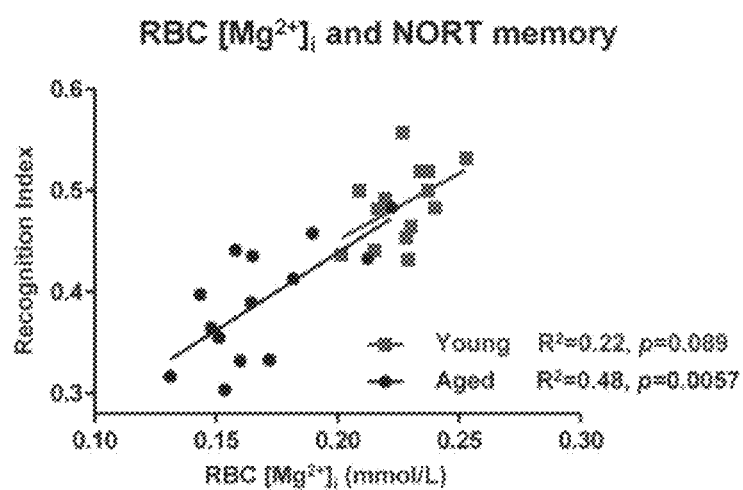
FIG. 21 is a graph showing correlation of red blood cell (RBC) intracellular magnesium concentration ($[Mg^{2+}]_i$) with learning and memory ability of animals, according to embodiments of the present disclosure.
Figure 22:
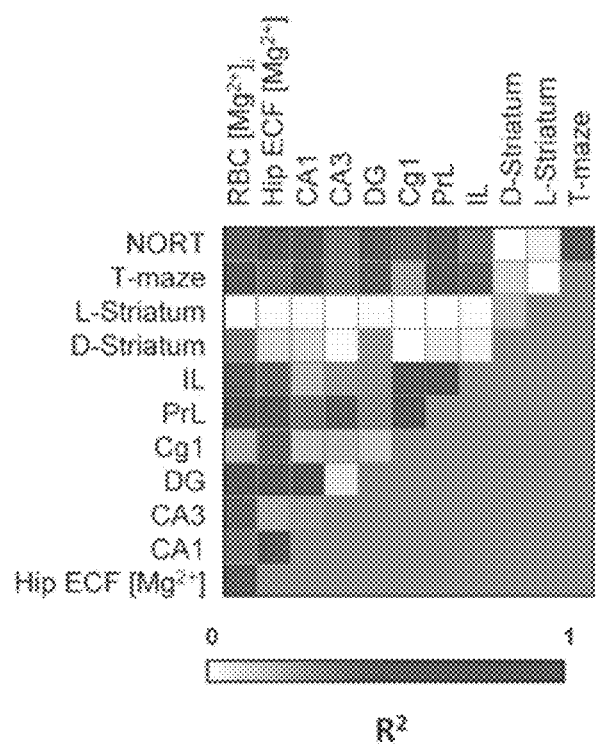
FIG. 22 is a graph showing correlation of RBC $[Mg^{2+}]_i$ with $[Mg^{2+}]_i$ levels in hippocampus and with synaptic density in specific brain regions controlling higher level cognition, according to embodiments of the present disclosure.

Further experiments showed that RBC $[Mg^{2+}]_i$ was strongly positively correlated with learning and memory ability of young and aged animals (FIG. 21). Further, RBC $[Mg^{2+}]_i$ was highly significantly correlated with $[Mg^{2+}]_i$ levels in hippocampus (hippocampus extracellular fluid; Hip ECF) and with synaptic density in specific brain regions associated with higher level cognition (executive function and memory), such as hippocampus and prefrontal cortex (FIG. 22). RBC $[Mg^{2+}]_i$ was not correlated with synaptic density of some brain regions, such as brain regions involved in voluntary movement, such as the striatum.

FIG. 21. Linear correlation between RBC ionized $[Mg^{2+}]_i$ and memory. Memory was determined by performance (recognition index) on the novel object recognition test (NORT) in aged rats (circles; p=0.0057). Trend of similar linear correlation between RBC ionized $[Mg^{2+}]_i$ and memory in young rats (squares; p=0.089). n=14 for each group.

The novel object recognition test (NORT) was used to evaluate the recognition memory of young and aged rats. The apparatus consisted of a square arena (60×60×40 cm) constructed from polyvinyl chloride, with black walls and floor. An overhead camera and a video recorder were used to monitor and record the animal's behavior for subsequent analysis.

Two days before the experiment, rats received two sessions of habituation to the arena and test room for 10 minutes/session/day. On the third day, each rat was placed in the box and exposed to 3 different objects for 5 minutes (sample phase), and then returned to its cage. The box and objects were cleaned between trials to prevent the buildup of olfactory cues. The number of times that the rats explored each object was then counted. Twenty-four hours later, the object with the maximum number of counts, which differed for each rat, was replaced with a novel object. The rat was then placed back in the box for another 5 minutes (acquisition phase). The recognition index was calculated as the percentage of counts on the novel object to the total counts during the acquisition phase. There were no differences in the motor abilities, explorative abilities and object preference (rats explore one object much more/less than the other objects in the sample phase) between young and aged rats.

FIG. 22. Correlation between RBC $[Mg^{2+}]_i$ and $Mg^{2+}$ of hippocampus and synaptic density of various brain regions. RBC $[Mg^{2+}]_i$ was strongly correlated with synaptic density of Pre-limbic (PrL) region of the Prefrontal Cortex and CA1, CA3, and dentate gyrus (DG) regions of hippocampus. Conversely, there was a weak or no correlation between RBC $[Mg^{2+}]_i$ and synaptic density of the L- and D-striatum. Linear analysis for $[Mg^{2+}]$, synaptic density, and performance on memory tests is shown in a heat map for $R^2$.

For determination of extracellular fluid (ECF) $[Mg^{2+}]$, rats were anesthetized with chloral hydrate (300 mg/kg, i.p.) and positioned onto a stereotaxic apparatus. A midline incision of the skull was executed and a small hole was made in the skull using a dental driller. A microdialysis guide cannula (CMA) was implanted into hippocampus (AP −5.2 mm, L −3.0 mm, V −4.2 mm). The guide cannula was fixed with light-solid dental cement. The rats were allowed to recover for 1 week before in vivo microdialysis sampling. During sampling, a microdialysis probe (CMA, dialysis length, 2 mm; OD, 0.5 mm) was inserted into the guide cannula in anesthetized rat. Artificial CSF solution (aCSF) was perfused at a flow rate of 0.2 µL/minute, for at least 30 minutes for equilibration. Samples were continuously collected for 2 hours on ice. The $Mg^{2+}$ level in the ECF was determined by calmagite chromometry.

Positive Correlation Between the Increase of Total Intracellular Magnesium Concentration (RBC) and the Improvement of Overall Cognitive Ability As shown in Example 3, human clinical trials showed that there was a positive correlation between the increase of total intracellular magnesium concentration (RBC) and the improvement of overall cognitive ability (Cognitive Composite Score) in subjects with mild cognitive impairment (MCI) (FIG. 17A). In addition, a positive correlation between the increase of total intracellular magnesium concentration (RBC) and the increase of speed on Trail Making Test part B (TMT-B) in subjects with MCI was observed (FIG. 17B).

Figure 23:
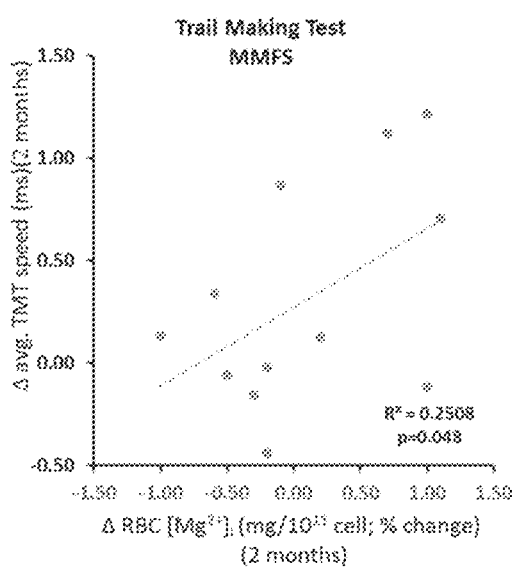
FIG. 23 is a graph showing correlation between the increase of total intracellular magnesium concentration (RBC) and the increase of speed on Trail Making Test (TMT) in human subjects with mild to moderate Alzheimer's Disease, according to embodiments of the present disclosure.
Figure 24:
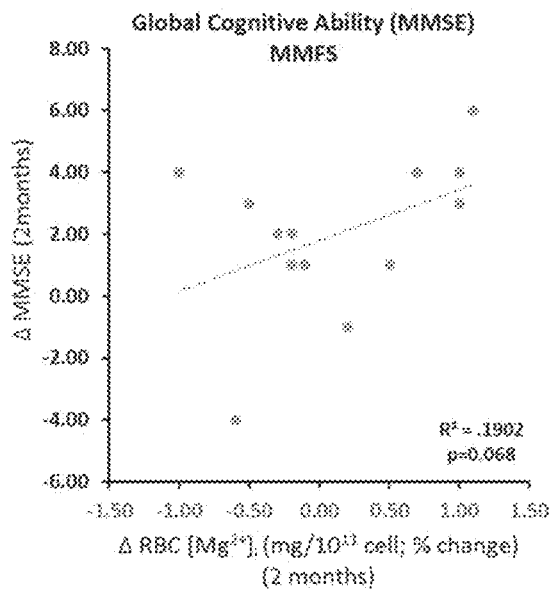
FIG. 24 is a graph showing correlation between the increase of total intracellular magnesium concentration (RBC) and the increase of overall cognitive ability in human subjects with mild to moderate Alzheimer's Disease, according to embodiments of the present disclosure.

In a separate trial, human subjects with mild to moderate Alzheimer's Disease (AD) were treated with MMFS-01. A positive correlation between the increase of total intracellular magnesium concentration (RBC) and the increase of speed on TMT-B was observed—similar to the statistically significant correlation observed in MCI patients. (r=0.501, p=0.048, n=12) (FIG. 23). A one-tailed test was used to test significance since the direction of the relationship between the percent change of RBC $[Mg^{2+}]_i$ and cognition was established in the MCI study. There was also a trend of a positive correlation between the increase of total intracellular magnesium concentration (RBC) and improvement of global cognitive ability (MMSE) in subjects with mild to moderate AD—similar to the statistically significant correlation observed in MCI patients. (r=0.436, p=0.068, n=13) (FIG. 24). Again, a one-tailed test was used to test significance since the direction of the relationship between the percent change of RBC $[Mg^{2+}]_i$ and cognition was established in the MCI study.

FIGS. 23 and 24. Correlations (R) were determined between the percent change of RBC $[Mg^{2+}]_i$ and the change from baseline in average TMT speed (milliseconds) (R=0.501 p=0.048, n=12; FIG. 23) or MMSE (R=0.436, p=0.068, n=13; FIG. 24) at Month 2 in MMFS treated subjects with mild-moderate AD. One-tailed test; see text for rationale for use of one-tailed test. Patients were treated with MMFS for 2 months, at 1800 mg/day. Dosage was set at one 600 mg 6 hour sustained release tablet in the morning, and one 600 mg 6 hour sustained release and one 600 mg instant release tablet in the evening.

Additional Embodiments

Notwithstanding the appended claims, embodiments of the present disclosure may be defined by the following clauses.

1. A method of modifying a functional property of neurons, comprising contacting one or more neurons comprising a presynaptic terminal, with a composition comprising an effective amount of an intracellular magnesium concentration ($[Mg^{2+}]_i$)-elevating agent, to modify one or more functional properties of the neurons,
  wherein the functional property comprises one or more of:
  a functional presynaptic terminal density;
  a mitochondrial function per unit dendritic area;
  a terminal abundance of one or more presynaptic $Ca^{2+}$ sensitivity-related proteins; and
  a probability of synaptic release in response to low frequency single action potential input.

2. The method of clause 1, wherein the one or more functional properties comprise the functional presynaptic terminal density, and wherein the contacting increases the functional presynaptic terminal density.

3. The method of clause 2, wherein the functional presynaptic terminal density is increased by 1.1 fold or more.

4. The method of any one of clauses 1 to 3, wherein the one or more functional properties comprise the mitochondrial function per unit dendritic area, and wherein the contacting increases the mitochondrial function per unit dendritic area.

5. The method of any one of clauses 1 to 4, wherein the mitochondrial function per unit dendritic area is increased by 20% or more.

6. The method of any one of clauses 1 to 5, wherein the one or more functional properties comprise the terminal abundance of one or more presynaptic $Ca^{2+}$ sensitivity-related proteins, and wherein the contacting increases the terminal abundance of one or more presynaptic $Ca^{2+}$ sensitivity-related proteins.

7. The method of clause 6, wherein the terminal abundance of one or more presynaptic $Ca^{2+}$ sensitivity-related proteins is increased by 20% or more.

8. The method of any one of clauses 1 to 7, wherein the functional properties comprise the probability of synaptic release in response to low frequency single action potential input, and wherein the contacting reduces the probability of synaptic release.

9. The method of clause 8, wherein the probability of synaptic release is reduced by 10% or more.

10. The method of any one of clauses 1 to 8, wherein the effective amount of the $[Mg^{2+}]_i$-elevating agent provides for an average extracellular concentration of magnesium from 0.6 mM to 1.4 mM.

11. The method of any one of clauses 1 to 10, wherein the $[Mg^{2+}]_i$-elevating agent comprises a magnesium-containing compound.

12. The method of clause 11, wherein the magnesium-containing compound comprises a magnesium salt.

13. The method of clause 12, wherein the magnesium salt comprises magnesium chloride, magnesium sulfate, magnesium threonate, magnesium oxide, magnesium citrate, magnesium gluconate, magnesium lactate, magnesium pidolate and magnesium diglycinate, magnesium acetate, magnesium ascorbate, magnesium lactate, magnesium malate, and/or magnesium taurate.

14. The method of any one of clauses 1 or 10, wherein the $[Mg^{2+}]_i$-elevating agent comprises an inhibitor of intracellular magnesium efflux or a magnesium influx promoter.

15. The method of any one of clauses 1 to 14, wherein the neurons are in vitro.

16. The method of any one of clauses 1 to 15, wherein the neurons are hippocampal neurons.

17. The method of any one of clauses 1 to 16, wherein the effective amount of the $[Mg^{2+}]_i$-elevating agent raises an intracellular concentration of magnesium in the one or more neurons by 1.1 fold or more.

18. The method of clause 17, wherein the intracellular concentration of magnesium is raised by 1.8 fold or more.

19. The method of any one of clauses 1 to 10, wherein the contacting is performed in vivo.

20. The method of clause 19, wherein the contacting comprises administering an effective amount of the $[Mg^{2+}]_i$-elevating agent, or a precursor thereof, to an individual.

21. The method of clause 21, wherein the $[Mg^{2+}]_i$-elevating agent, or a precursor thereof, is administered orally.

22. The method of any one of clauses 19 to 21, wherein the method is for treating a neurological disorder, or a symptom thereof, in the individual.

23. The method of clause 22, wherein the neurological disorder is associated with insufficient synaptic density and/or insufficient neuron number in the individual.

24. The method of clause 22 or 23, wherein the neurological disorder is associated with sustained and/or elevated spontaneous activity of neurons in the individual.

25. The method of any one of clauses 22 to 24, wherein the neurological disorder is selected from Alzheimer's disease, mild cognitive impairment (MCI), Parkinson's disease, dementia, Huntington's disease, autism, schizophrenia, cognitive decline as secondary effect of disease or medical treatment, depression, sleep disorder, anxiety, attention deficit hyperactivity disorder (ADHD), migraine, headache, stroke, neuropathy, epilepsy, cerebral palsy, chronic pain, involuntary muscular contractions and convulsive twitches, spasm, wrinkling, dystonia and tremor, anxiety and depression associated with sustained neural activity in prefrontal cortex (PFC) and amygdala, and insomnia.

26. A method of determining the amenability of an individual to treatment for a neurological disorder, comprising:
administering a $[Mg^{2+}]_i$-elevating agent to an individual having or suspected of having a neurological disorder; and
determining a first level of magnesium in blood cells of a first blood sample obtained from the individual before the administering and a second level of magnesium in blood cells of a second blood sample obtained from the individual after the administering,
wherein the level of magnesium is correlated with an intracellular level of magnesium in brain neurons and/or a level of magnesium in cerebral spinal fluid of the individual, and
wherein the individual is determined to be amenable to treatment by the $[Mg^{2+}]_i$-elevating agent for the neurological disorder when the second level of magnesium is greater than the first level of magnesium.

27. The method of clause 25, wherein the individual is determined to be amenable to treatment by the $[Mg^{2+}]_i$-elevating agent for the neurological disorder when the second level of magnesium is greater by 5% or more relative to the first level of magnesium.

28. A method comprising:
administering a magnesium-containing compound to an individual having or suspected of having a neurological disorder; and
determining a first level of magnesium in blood cells of a first blood sample obtained from the individual before the administering and a second level of magnesium in blood cells of a second blood sample obtained from the individual after the administering.

29. The method of any one of clauses 25 to 29, further comprising measuring the level of magnesium in the blood cells, before and/or after the administering, to determine the level of magnesium.

30. The method of clause 29, wherein the measuring further comprises obtaining a blood sample from the individual.

31. The method of any one of clauses 25 to 30, further comprising continuing administration of the $[Mg^{2+}]_i$-elevating agent to the individual when the second level of magnesium is greater than the first level of magnesium.

32. The method of clause 31, wherein administration of the $[Mg^{2+}]_i$-elevating agent to the individual is continued when the second level of magnesium is greater by 5% or more relative to the first level of magnesium.

33. The method of any one of clauses 25 to 32, further comprising evaluating a cognitive competency of the individual before and/or after the administering.

34. The method of clause 33, wherein the cognitive competency comprises executive function, working memory, attention and/or short-term episodic memory.

35. The method of clause 33 or 34, further comprising administering a cognitive test for evaluating the cognitive competency of the individual before and/or after administering the $[Mg^{2+}]_i$-elevating agent.

36. The method of any one of clauses 33 to 35, further comprising continuing administration of the $[Mg^{2+}]_i$-elevating agent to the individual when the cognitive competency is improved from before to after administering the $[Mg^{2+}]_i$-elevating agent, and/or when the second level of magnesium is greater than the first level of magnesium.

37. The method of any one of clauses 33 to 36, wherein the administration of the $[Mg^{2+}]_i$-elevating agent to the individual is not continued when neither the cognitive competency is improved from before to after administering the $[Mg^{2+}]_i$-elevating agent, nor the second level of magnesium is greater than the first level of magnesium.

38. The method of any one of clauses 25 to 37, wherein the neurological disorder comprises cognitive impairment.
39. The method of clause 38, wherein the cognitive impairment comprises age-related cognitive decline, mild cognitive impairment or Alzheimer's disease.
40. The method of clause 38 or 39, wherein the cognitive impairment comprises cognitive fluctuation.
41. The method of any one of clauses 25 to 40, wherein the neurological disorder comprises a magnesium deficiency-caused neurological disorder.
42. The method of any one of clauses 25 to 41, wherein the $[Mg^{2+}]_i$-elevating agent is administered orally.
43. The method of any one of clauses 25 to 42, wherein the blood cells comprise red blood cells.
44. The method of any one of clauses 25 to 43, wherein the $[Mg^{2+}]_i$-elevating agent comprises magnesium threonate.
45. The method of any one of clauses 25 to 44, wherein the $[Mg^{2+}]_i$-elevating agent is administered at a dose of from 5 mg/kg/day to 50 mg/kg/day.
46. The method of any one of clauses 25 to 45, wherein the $[Mg^{2+}]_i$-elevating agent is administered for 9 days or more.
47. The method of any one of clauses 25 to 46, wherein the individual is human.
48. The method of clause 47, wherein the individual has an age of from 45 years to 80 years.
49. A method of reducing a cognitive impairment in an individual, comprising:
   administering an effective amount of magnesium threonate, or a substantially equivalent amount of a precursor thereof, to a human individual having or suspected of having a cognitive impairment, wherein the effective amount is sufficient to reduce a functional age of a brain of the human individual.
50. The method of clause 49, wherein the effective amount comprises an amount from 20 mg/kg/day to 50 mg/kg/day.
51. The method of clause 50, wherein the amount is from 20 mg/kg/day to 30 mg/kg/day.
52. The method of any one of clauses 49 to 51, wherein the magnesium threonate, or precursor thereof is administered for 6 days or more.
53. The method of any one of clauses 49 to 52, wherein the functional age is reduced by 5 years or more.
54. The method of any one of clauses 49 to 53, wherein the cognitive impairment comprises cognitive fluctuation.
55. The method of any one of clauses 49 to 54, wherein the cognitive impairment comprises age-related cognitive decline and/or mild cognitive impairment.
56. The method of any one of clauses 49 to 55, wherein the cognitive impairment comprises a magnesium deficiency-caused neurological disorder.
57. The method of any one of clauses 49 to 56, wherein the magnesium threonate, or precursor thereof is administered orally.
58. The method of any one of clauses 49 to 57, wherein the human individual has an age of from 45 years to 80 years.
59. The method of any one of clauses 49 to 58, further comprising determining a level of intracellular concentration of magnesium in cells of a blood sample from the human individual.
60. The method of clause 59, wherein the cells comprise red blood cells.
61. The method of clause 59 or 60, further comprising determining:
   a first level of intracellular concentration of magnesium in cells of a first blood sample from the human individual before administering the magnesium threonate, or precursor thereof; and
   a second level of the intracellular concentration of magnesium in cells of a second blood sample from the human individual after administering the magnesium threonate, or precursor thereof.
62. The method of clause 61, further comprising continuing administering the magnesium threonate, or precursor thereof when the second level is higher than the first level.
63. The method of any one of clauses 59 to 62, wherein the determining comprises obtaining a blood sample from the human individual; and measuring the intracellular concentration of magnesium in the cells of the blood sample.
64. A method of identifying an active agent that modifies a functional property of a neuron, comprising:
   contacting a first population of neurons in vitro with a first medium comprising a candidate agent, wherein the neurons comprise a magnesium indicator dye; and
   measuring a level of intracellular magnesium ($[Mg^{2+}]_i$) in one or more subcellular regions of the neurons after the contacting,
   wherein the candidate agent is determined to be an active candidate agent that modifies a $[Mg^{2+}]_i$-dependent functional property of a neuron when the measured level is higher than a reference level of intracellular magnesium, and wherein the $[Mg]_i$-dependent functional property comprises one or more of:
      a functional presynaptic terminal density;
      a mitochondrial function per unit dendritic area;
      an abundance of one or more presynaptic $Ca^{2+}$ sensitivity-related proteins; and
      an average probability of synaptic release in response to low frequency single action potential input.
65. The method of clause 64, wherein the candidate agent does not comprise magnesium.
66. The method of clause 64, wherein the candidate agent comprises magnesium.
67. The method of any one of clauses 64 to 66, wherein the candidate agent is an ion channel blocker.
68. The method of any one of clauses 64 to 67, wherein the extracellular magnesium concentration is from 0.5 mM to 2 mM.
69. The method of any one of clauses 64 to 68, further comprising:
   contacting a second population of neurons in vitro with a second medium comprising the candidate agent; and
   measuring a level of mitochondrial function in one or more subcellular regions of the neurons after the contacting,
   wherein the candidate agent is determined to be an active agent for modifying a $[Mg^{2+}]_i$-dependent functional property of a neuron when the measured level of intracellular magnesium is higher than a reference level of intracellular magnesium, and when the measured level of mitochondrial function is higher than a reference level of mitochondrial function.
70. The method of clause 69, wherein the mitochondrial function is mitochondrial number and/or mitochondrial membrane potential.
71. The method of any one of clauses 64 to 70, wherein the one or more subcellular regions comprise neuronal branches.
72. The method of clause 71, wherein measuring the level of intracellular magnesium comprises:
   measuring for each branch:
      an average fluorescence level from the magnesium indicator dye; and
      a diameter of the branch; and calculating the level of intracellular magnesium based on the diameter and the average fluorescence level in each branch.

73. The method of any one of clauses 64 to 72, wherein the reference level is derived from a baseline level in the one or more neurons before the contacting.

74. The method of any one of clauses 64 to 72, wherein the reference level is a control level in one or more negative control neurons after contacting with a control medium that does not comprise the candidate agent.

75. The method of any one of clauses 64 to 74, wherein the one or more neurons are post-synaptically connected.

76. The method of clause 75, further comprising measuring the functional presynaptic density of the one or more neurons.

77. The method of any one of clauses 64 to 76, wherein the neurons are primary neurons.

78. The method of clause 77, wherein the neurons are hippocampal neurons.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method comprising:
   administering an intracellular magnesium concentration-elevating agent to an individual having or suspected of having a neurological disorder to increase the intracellular concentration of magnesium in the individual;
   determining a first level of magnesium in blood cells of a first blood sample obtained from the individual before the administering; and
   evaluating a change in cognitive competency of the individual from before to after the administering.

2. The method of claim 1, further comprising measuring the level of magnesium in the blood cells, before the administering, to determine the first level of magnesium.

3. The method of claim 1, further comprising determining a second level of magnesium in blood cells of a second blood sample obtained from the individual after the administering.

4. The method of claim 3, further comprising measuring the level of magnesium in the blood cells, after the administering, to determine the second level of magnesium.

5. The method of claim 3, further comprising continuing administration of the intracellular magnesium concentration-elevating agent to the individual when the second level of magnesium is greater than the first level of magnesium.

6. The method of claim 1, wherein the cognitive competency comprises executive function, working memory, attention and/or short-term episodic memory.

7. The method of claim 6, further comprising administering a cognitive test for evaluating the cognitive competency of the individual before and/or after administering the intracellular magnesium concentration-elevating agent.

8. The method of claim 3, further comprising continuing administration of the intracellular magnesium concentration-elevating agent to the individual when the cognitive competency is not improved or is substantially the same as from before to after administering the intracellular magnesium concentration-elevating agent, and when the second level of magnesium is greater than the first level of magnesium.

9. The method of claim 1, wherein the neurological disorder comprises cognitive impairment and/or a magnesium deficiency-caused neurological disorder.

10. The method of claim 9, wherein the cognitive impairment comprises age-related cognitive decline, mild cognitive impairment, Alzheimer's disease, or cognitive fluctuation.

11. The method of claim 1, wherein the blood cells comprise red blood cells.

12. The method of claim 1, wherein the intracellular magnesium concentration-elevating agent comprises a magnesium-containing compound.

13. The method of claim 1, wherein the magnesium is ionized magnesium.

14. The method of claim 1, wherein the magnesium is total intracellular magnesium.

* * * * *